(12) United States Patent
Goldschneider et al.

(10) Patent No.: US 7,578,998 B2
(45) Date of Patent: *Aug. 25, 2009

(54) CHIMERIC CYTOKINE OF IL-7 AND BETA-CHAIN OF HGF AND METHODS OF USE

(75) Inventors: Irving Goldschneider, Avon, CT (US); Laijun Lai, Newington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/601,059

(22) Filed: Nov. 17, 2006

(65) Prior Publication Data

US 2007/0122380 A1      May 31, 2007

Related U.S. Application Data

(60) Continuation-in-part of application No. 10/792,645, filed on Mar. 3, 2004, now abandoned, which is a division of application No. 09/823,933, filed on Mar. 30, 2001, now Pat. No. 6,749,847.

(60) Provisional application No. 60/193,273, filed on Mar. 30, 2000.

(51) Int. Cl.
     *A61K 38/19*      (2006.01)
     *A61K 38/20*      (2006.01)

(52) U.S. Cl. ..................... 424/85.1; 530/351
(58) Field of Classification Search ............... None
See application file for complete search history.

(56) References Cited

U.S. PATENT DOCUMENTS 6,749,847 B2 * 6/2004 Goldschneider et al. ... 424/85.2

OTHER PUBLICATIONS

Mikayama et al. Proc. Natl. Acad. Sci. USAvol. 90, pp. 10056-10060.*
Voet et al. Biochemistry John Wiley & Sons, Inc., pp. 126-128 and 228-234.*
Laijun Lai et al., A Recombinant Single-Chain IL-7/HGF-beta Hybrid Cytokine Induces Juxtacrine Interactions of the IL-7 and HGF (c-Met) Receptors and Stimulates the Proliferation of CFU-S12, CLPs, and Pre-Pro-B Cells. Blood (2006)107(6): 1776-1784.

* cited by examiner

*Primary Examiner*—Prema Mertz
(74) *Attorney, Agent, or Firm*—McCarter & English, LLP

(57) ABSTRACT

The present invention relates to a single-chain or chimeric polypeptide comprising a cytokine and a growth factor linked by at least one amino acid residue, and wherein the chimeric polypeptide enhances the proliferation and/or differentiation of hematopoietic precursor cells. In particular the invention relates to, a chimeric polypeptide comprising the beta-chain of hepatocyte growth factor, and IL-7 linked by at least one amino acid, and wherein the chimeric polypeptide demonstrates pre-pro-B proliferation and growth stimulating activity.

12 Claims, 36 Drawing Sheets

PPBSF cofactor:        V V N G I P T Q T N I G W M V S L

Mouse HGF β chain:     V V N G I P T Q T T V G W M V S L

Rat HGF β chain:       V V N G I P T Q T T V G W M V S L

Human HGF β chain:     V V N G I P T R T N I G W M V S L

Profile hits — PAN — KRINGLE — KRINGLE — KRINGLE — KRINGLE — TRYPSIN_DOM
Pfam hits — PAN — Kringle — Kringle — Kringle — Kringle — Trypsin

B.

| DB | Accession | Name/Description | score | E-value |
|---|---|---|---|---|
| sp | P14210 | HGF_HUMAN Hepatocyte growth factor precursor (Scatter ... | 1547 | 0.0 |
| sp_vs | P14210-3 | Isoform 3 of P14210 [HGF] [Homo sapiens (Human)] | 1531 | 0.0 |
| tr | Q76BS1 | _BOVIN Hepatocyte growth factor [hgf] [Bos taurus (Bovi... | 1459 | 0.0 |
| tr | Q867B7 | _CANFA Hepatocyte growth factor [HGF] [Canis familiaris... | 1458 | 0.0 |
| tr | Q9BH09 | _FELCA Hepatocyte growth factor HGF [HGF] [Felis silves... | 1457 | 0.0 |
| sp | Q08048 | HGF_MOUSE Hepatocyte growth factor precursor (Scatter ... | 1428 | 0.0 |
| tr | Q53WS5 | _MOUSE Hepatocyte growth factor/scatter factor (Hgf pro... | 1428 | 0.0 |
| sp | P17945 | HGF_RAT Hepatocyte growth factor precursor (Scatter fa... | 1425 | 0.0 |
| tr | Q8C9G5 | _MOUSE 3 days neonate thymus cDNA, RIKEN full-length en... | 1424 | 0.0 |
| sp_vs | Q08048-2 | Isoform Short of Q08048 [Hgf] [Mus musculus (Mouse)] | 1412 | 0.0 |
| tr | Q90978 | _CHICK Hepatocyte growth factor /scatter factor [HGF/SF... | 1198 | 0.0 |
| tr | Q91402 | _9PIPI Hepatocyte growth factor [HGF] [Xenopus] | 1075 | 0.0 |
| tr | Q5RGG3 | _BRARE Novel protein similar to vertebrate hepatocyte g... | 705 | 0.0 |
| tr | Q788Q2 | _CHICK HGF/SF protein precursor (Fragment) [HGF/SF] [Ga... | 667 | 0.0 |
| tr | Q91691 | _XENLA Growth factor Livertine [Xenopus laevis (African... | 651 | 0.0 |
| sp | P26927 | HGFL_HUMAN Hepatocyte growth factor-like protein precu... | 630 | e-179 |
| tr | Q6GTN4 | _HUMAN Macrophage stimulating 1 (Hepatocyte growth fact... | 630 | e-179 |
| tr | Q53GN8 | _HUMAN Macrophage stimulating 1 (Hepatocyte growth fact... | 630 | e-179 |
| tr | P70006 | _XENLA Hepatocyte growth factor-like protein precursor ... | 629 | e-178 |
| tr | Q7ZTN9 | _XENLA MGC54016 protein [Xenopus laevis (African clawed... | 625 | e-177 |
| tr | Q90865 | _CHICK Hepatocyte growth factor-like/macrophage stimula... | 616 | e-174 |
| tr | P70521 | _RAT Macrophage stimulating protein precursor (Macropha... | 612 | e-173 |
| sp | P26928 | HGFL_MOUSE Hepatocyte growth factor-like protein precu... | 608 | e-172 |
| tr | Q6GTL1 | _MOUSE Macrophage stimulating 1 (Hepatocyte growth fact... | 608 | e-172 |
| tr | Q91XG8 | _MOUSE Macrophage stimulating 1 (Hepatocyte growth fact... | 607 | e-172 |
| tr | Q3UZ05 | _MOUSE Adult male thymus cDNA, RIKEN full-length enrich... | 604 | e-171 |
| tr | Q5XFY1 | _BRARE Macrophage stimulating 1 (Hepatocyte growth fact... | 596 | e-169 |
| tr | Q90ZN6 | _BRARE Hepatocyte growth factor-like 1 [mst1] [Brachyda... | 596 | e-168 |
| tr | Q4SUG4 | _TETNG Chromosome undetermined SCAF13941, whole genome ... | 591 | e-167 |
| sp_vs | P14210-2 | Isoform 2 of P14210 [HGF] [Homo sapiens (Human)] | 587 | e-166 |
| sp_vs | P14210-4 | Isoform 4 of P14210 [HGF] [Homo sapiens (Human)] | 583 | e-165 |
| sp_vs | P14210-5 | Isoform 5 of P14210 [HGF] [Homo sapiens (Human)] | 571 | e-161 |
| tr | Q24K22 | _BOVIN Macrophage stimulating 1 (Hepatocyte growth fact... | 568 | e-160 |
| sp | O18783 | PLMN_MACEU Plasminogen precursor (EC 3.4.21.7) [Contai... | 526 | e-147 |
| tr | Q4RX92 | _TETNG Chromosome 11 SCAF14979, whole genome shotgun se... | 523 | e-147 |
| tr | Q13208 | _HUMAN Hepatocyte growth factor-like protein homolog [H... | 521 | e-146 |
| sp | P06867 | PLMN_PIG Plasminogen precursor (EC 3.4.21.7) [Contains... | 501 | e-140 |
| tr | Q19AZ9 | _PIG Plasminogen [Sus scrofa (Pig)] | 498 | e-139 |
| sp | P20918 | PLMN_MOUSE Plasminogen precursor (EC 3.4.21.7) [Contai... | 495 | e-138 |
| tr | Q6PBA6 | _BRARE Plasminogen [plg] [Brachydanio rerio (Zebrafish)... | 495 | e-138 |
| sp | P06868 | PLMN_BOVIN Plasminogen precursor (EC 3.4.21.7) [Contai... | 492 | e-137 |
| tr | Q3V1T9 | _MOUSE 18 days pregnant adult female placenta and extra... | 492 | e-137 |
| tr | Q5R8X6 | _PONPY Hypothetical protein DKFZp470G2422 [DKFZp470G242... | 486 | e-135 |
| sp | Q01177 | PLMN_RAT Plasminogen precursor (EC 3.4.21.7) [Contains... | 484 | e-135 |
| tr | Q5BKB6 | _RAT Plasminogen [Plg] [Rattus norvegicus (Rat)] | 484 | e-135 |
| sp | P12545 | PLMN_MACMU Plasminogen precursor (EC 3.4.21.7) [Contai... | 483 | e-135 |
| sp | Q29485 | PLMN_ERIEU Plasminogen precursor (EC 3.4.21.7) [Contai... | 483 | e-135 |
| tr | Q50LG6 | _ORYLA Plasminogen [plg] [Oryzias latipes (Medaka fish)... | 474 | e-132 |
| sp | P00747 | PLMN_HUMAN Plasminogen precursor (EC 3.4.21.7) [Contai... | 473 | e-132 |
| tr | Q5TEH4 | _HUMAN Plasminogen [PLG] [Homo sapiens (Human)] | 473 | e-132 |
| tr | Q6GP14 | _XENLA LOC397993 protein [LOC397993] [Xenopus laevis (A... | 467 | e-130 |
| tr | Q5DVP8 | _ONCMY Plasminogen precursor (EC 3.4.21.7) [plg] [Oncor... | 460 | e-127 |
| tr | Q1HP67 | _HUMAN Lipoprotein, Lp(A) [LPA] [Homo sapiens (Human)] | 451 | e-125 |
| sp | P08519 | APOA_HUMAN Apolipoprotein(a) precursor (EC 3.4.21.-) (... | 449 | e-124 |
| tr | Q5VTD7 | _HUMAN OTTHUMP00000017543 [LPA] [Homo sapiens (Human)] | 449 | e-124 |
| sp | P14417 | APOA_MACMU Apolipoprotein(a) (EC 3.4.21.-) (Apo(a)) (L... | 435 | e-120 |
| tr | Q2TV78 | _HUMAN Brain-rescue-factor-1 [Homo sapiens (Human)] | 419 | e-115 |

FIG. 37 B (cont.)

| DB | Accession | Name/Description | score | E-value |
|---|---|---|---|---|
| tr | Q4SBT4 | _TETNG Chromosome 19 SCAF14664, whole genome shotgun se... | 405 | e-111 |
| tr | O42341 | _CHICK HGF alpha-chain (Fragment) [Gallus gallus (Chick... | 404 | e-111 |
| tr | Q6TCI0 | _MOUSE Angiostatin [Plg] [Mus musculus (Mouse)] | 404 | e-111 |
| tr | Q3KRB2 | _HUMAN Hepatocyte growth factor (Hepapoietin A; scatter... | 397 | e-108 |
| tr | Q59H59 | _HUMAN Hepatocyte growth factor isoform 1 preproprotein... | 397 | e-108 |
| sp_vs | P14210-6 | Isoform 6 of P14210 [HGF] [Homo sapiens (Human)] | 397 | e-108 |
| tr | Q7TP84 | _RAT Abl-346 [Rattus norvegicus (Rat)] | 383 | e-104 |
| tr | Q8WMR1 | _CANFA Plasminogen (Fragment) [Canis familiaris (Dog)] | 374 | e-102 |
| tr | O55027 | _MOUSE Hepatocyte growth factor NK1 [Hgf] [Mus musculus... | 362 | 2e-98 |
| tr | Q28398 | _ERIEU Apolipoprotein(A) (Fragment) [Erinaceus europaeu... | 358 | 3e-97 |
| tr | Q4SUF5 | _TETNG Chromosome undetermined SCAF13953, whole genome ... | 299 | 3e-79 |
| tr | Q4SGT4 | _TETNG Chromosome 14 SCAF14590, whole genome shotgun se... | 297 | 9e-79 |
| tr | Q8AVB0 | _BRARE Plasminogen (Fragment) [plg] [Brachydanio rerio ... | 285 | 5e-75 |
| tr | Q4RF09 | _TETNG Chromosome 13 SCAF15122, whole genome shotgun se... | 276 | 2e-72 |
| tr | O46506 | _PAPHA Apolipoprotein a (Fragment) [BABAPOA] [Papio ham... | 268 | 5e-70 |
| tr | Q8C4E2 | _MOUSE 0 day neonate cerebellum cDNA, RIKEN full-length... | 255 | 5e-66 |
| tr | Q9PU78 | _CRONI Hepatocyte growth factor-like protein (Fragment)... | 251 | 1e-64 |
| tr | Q9N1B8 | _SHEEP Hepatocyte growth factor (Fragment) [HGF] [Ovis ... | 241 | 8e-62 |
| tr | Q49A61 | _HUMAN MST1 protein [MST1] [Homo sapiens (Human)] | 229 | 2e-58 |
| sp | P81286 | PLMN_SHEEP Plasminogen (EC 3.4.21.7) (Fragment) [PLG] ... | 220 | 1e-55 |
| tr | O46507 | _PAPHA Plasminogen (Fragment) [BABPEPSG] [Papio hamadry... | 212 | 5e-53 |
| tr | Q13209 | _HUMAN Hepatocyte growth factor-like protein homolog (F... | 212 | 5e-53 |
| sp | P80010 | PLMN_HORSE Plasminogen (EC 3.4.21.7) [Contains: Plasmi... | 209 | 3e-52 |
| sp | P80009 | PLMN_CANFA Plasminogen (EC 3.4.21.7) [Contains: Plasmi... | 209 | 4e-52 |
| tr | Q50LG7 | _ORYLA Tissue-type plasminogen activator [tPA] [Oryzias... | 207 | 9e-52 |
| tr | Q5BKN3 | _XENTR MGC107814 protein [MGC107814] [Xenopus tropicali... | 190 | 2e-46 |
| sp | P19637 | TPA_RAT Tissue-type plasminogen activator precursor (E... | 188 | 8e-46 |
| sp | Q28198 | TPA_BOVIN Tissue-type plasminogen activator precursor ... | 186 | 2e-45 |
| tr | Q2KJG9 | _BOVIN Plasminogen activator, tissue [PLAT] [Bos taurus... | 186 | 4e-45 |
| tr | Q5R8J0 | _PONPY Hypothetical protein DKFZp46902126 [DKFZp4690212... | 184 | 9e-45 |
| tr | Q6P7U0 | _MOUSE Plasminogen activator, tissue (In vitro fertiliz... | 184 | 1e-44 |
| sp | P11214 | TPA_MOUSE Tissue-type plasminogen activator precursor ... | 183 | 2e-44 |
| tr | Q4RF08 | _TETNG Chromosome 13 SCAF15122, whole genome shotgun se... | 181 | 1e-43 |
| tr | Q8SQ23 | _PIG T-plasminogen activator [Sus scrofa (Pig)] | 180 | 2e-43 |
| sp | P00750 | TPA_HUMAN Tissue-type plasminogen activator precursor ... | 180 | 2e-43 |
| tr | Q6PJA5 | _HUMAN PLAT protein (Fragment) [PLAT] [Homo sapiens (Hu... | 180 | 2e-43 |
| sp_vs | P00750-3 | Isoform 3 of P00750 [PLAT] [Homo sapiens (Human)] | 180 | 2e-43 |
| tr | Q6P7I9 | _XENLA T-pa protein [t-pa] [Xenopus laevis (African cla... | 179 | 3e-43 |
| tr | Q5FVW1 | _XENTR MGC108417 protein [MGC108417] [Xenopus tropicali... | 178 | 8e-43 |
| tr | Q503B0 | _HUMAN Plasminogen activator, tissue [PLAT] [Homo sapie... | 178 | 8e-43 |
| tr | Q6DFJ5 | _XENLA Lpa-prov protein [lpa-prov] [Xenopus laevis (Afr... | 177 | 1e-42 |
| tr | Q9BGN9 | _BOVIN Hepatocyte growth factor (Fragment) [HGF] [Bos t... | 173 | 2e-41 |
| sp | P00735 | THRB_BOVIN Prothrombin precursor (EC 3.4.21.5) (Coagul... | 172 | 4e-41 |

Profile hits
Pfam hits                    IL7

B.

```
DB Accession       Name/Description                                    score  E-value
sp P13232  IL7_HUMAN Interleukin-7 precursor (IL-7) [IL7] [Homo s...    335   5e-91
tr Q8HZN1  _9PRIM Interleukin-7 [Papio cynocephalus x Papio anubis]    324   7e-88
tr Q95J83  _MACMU Interleukin 7 [Macaca mulatta (Rhesus macaque)]      324   7e-88
sp Q28540  IL7_SHEEP Interleukin-7 precursor (IL-7) [IL7] [Ovis a...   241   6e-63
sp P26895  IL7_BOVIN Interleukin-7 precursor (IL-7) [IL7] [Bos ta...   241   1e-62
tr Q8HYR8  _BOVIN IL-7 [Bos taurus (Bovine)]                           238   5e-62
tr Q9N2G6  _PIG Interleukin-7 [IL-7] [Sus scrofa (Pig)]                235   4e-61
tr Q5FBY9  _HUMAN IL7 nirs variant 2 [IL7] [Homo sapiens (Human)]      227   2e-58
tr Q0MUT2  _CANFA Interleukin 7 [Canis familiaris (Dog)]               191   1e-47
sp P10168  IL7_MOUSE Interleukin-7 precursor (IL-7) [Il7] [Mus mu...   182   6e-45
tr Q544C8  _MOUSE Adult male aorta and vein cDNA, RIKEN full-lengt...  182   6e-45
sp P56478  IL7_RAT Interleukin-7 precursor (IL-7) [Il7] [Rattus n...   179   5e-44
tr Q91Y32  _RAT Interleukin-7 [IL-7] [Rattus norvegicus (Rat)]         176   2e-43
tr Q8C9S3  _MOUSE 3 days neonate thymus cDNA, RIKEN full-length en...  162   6e-39
tr Q3UT18  _MOUSE 2 cells egg cDNA, RIKEN full-length enriched lib...  138   7e-32
tr Q5FBX5  _HUMAN IL7 nirs variant 1 [IL7] [Homo sapiens (Human)]      137   2e-31
tr Q5FBY5  _HUMAN IL7 nirs variant 4 [IL7] [Homo sapiens (Human)]       85   1e-15
tr Q5FBY3  _HUMAN IL7 nirs variant 6 [IL7] [Homo sapiens (Human)]       76   5e-13
tr Q5FBY6  _HUMAN IL7 nirs variant 3 [IL7] [Homo sapiens (Human)]       43   0.004
tr Q5FBY8  _HUMAN IL7 nirs variant 5 [IL7] [Homo sapiens (Human)]       42   0.007
tr Q3CBP8  _9CLOT Hypothetical protein [AmetDRAFT_2800] [Alkaliphi...    36   0.52
sp Q05766  CYAA_PASMU Adenylate cyclase (EC 4.6.1.1) (ATP pyropho...     34   2.6
tr Q23ZE2  _TETTH Hypothetical protein [TTHERM_00787210] [Tetrahym...    34   2.6
tr Q0UTJ3  _PHANO Hypothetical protein [SNOG_04921] [Phaeosphaeria...    33   4.4
tr Q5EJ04  _9HIV1 Envelope glycoprotein (Fragment) [env] [Human im...    33   5.7
tr Q22K19  _TETTH SNF2 family N-terminal domain containing protein...    33   5.7
tr Q8I5A3  _PLAF7 Asparagine-rich protein, putative [PFL1530w] [Pl...    33   5.7
tr Q9LPD9  _ARATH T12C22.19 protein [T12C22.19] [Arabidopsis thali...    32   7.5
tr Q6BY30  _DEBHA Debaryomyces hansenii chromosome A of strain CBS...    32   9.8
```

CHIMERIC CYTOKINE OF IL-7 AND BETA-CHAIN OF HGF AND METHODS OF USE

CROSS-REFERENCE TO RELATED APPLICATIONS

This application is a continuation-in-part of U.S. patent application Ser. No. 10/792,645 (Public. No.: 2004/0167317), filed Mar. 3, 2004, now abandoned, which is a divisional application of U.S. patent application Ser. No. 09/823,933, filed Mar. 30, 2001, now U.S. Pat. No. 6,749,847; which claims priority under 35 U.S.C. § 119(e) to U.S. Provisional Patent Application No. 60/193,273, filed on Mar. 30, 2000, the disclosures of which are incorporated by reference in their entirety for all purposes.

STATEMENT REGARDING FEDERALLY SPONSORED RESEARCH

The U.S. Government has certain rights in this invention pursuant to Grant No.: R01-AI32752, awarded by the National Institutes of Health (NIH).

INCORPORATION BY REFERENCE

The present application hereby incorporates by reference, in its entirety, the Sequence Listing, and identical CRF of the Sequence Listing filed herewith. The CRF contains nucleotide and amino acid sequences, SEQ. ID NO. 1-14, in file: "98121.00130SEQLIST.ST25.txt"; created: Nov. 13, 2006; OS: MS Windows XP; Software: PatentIn v3.3; size: 27 KB. The information contained in the Sequence Listing submitted, herewith, in the instant application is identical to the sequence information contained in the computer readable form.

FIELD OF THE INVENTION

The present invention relates to the discovery of a novel chimeric polypeptide comprising IL-7 and HGF-beta referred to herein as a pre-pro-B Cell Growth Stimulating Factor, or PPBSF, and methods for its production from recombinant IL-7 (rIL-7) and HGF-beta (rHGF-beta).

BACKGROUND

Hepatocyte growth factor (HGF), also called scatter factor SF, is a heparin-binding glycoprotein that is secreted as a biologically inert single chain (pro-HGF) and is converted to its bioactive form by targeted protease digestion to an active disulfide-linked heterodimer. HGF is a natural ligand for the c-MET proto-oncogene product of a novel family of heterodimeric receptor tyrosine kinases that include Ron, Sea and Sex. It is a pleiotropic factor derived from the mesenchyme that regulates epithelial, neural, endothelial, muscle and hemopoietic cell growth, motility, morphogenesis and regeneration in many tissues and organs. The importance of HGF is seen in transgenic mice homozygous for a null mutation in the HGF gene. Such mice do not survive beyond fifteen days of embryonic development.

Mature bioactive HFG is a heterodimer consisting of a 60 kD alpha and 30 kD beta chain held together by a single disulfide bond. Structure function analysis indicates that the beta chain of HGF is required for mitogenic activity, whereas the receptor-binding domain is located in the alpha chain. Its primary structure is highly conserved among mouse, rat, human and other species. The alpha chain contains a hairpin loop at its amino terminus and four unique domains known as "kringles", while its beta chain contains a serine protease-like structure. Hence, HGF is closely homologous to plasminogen, but has no known protease activity due to mutation of the catalytic site.

HGF has been reported to be sequestered in the extracellular matrix (ECM) in vitro as well as in vivo, where it is bound to cell surface heparin sulfate glycosoaminoglycans. In general, HGF mRNA is expressed in stromal cells, whereas HGF receptor expression is mainly detected in epithelial and other parenchymal cells. This pattern suggests that HGF is an important paracrine mediator of the interaction between the parenchymal and stromal components of various tissues both during fetal development and in the maintenance of homeostasis in adult tissues.

Although a great deal is known about the actions of HGF in nonhemopoietic tissues, the role of HGF in the regulation of hematopoiesis, particularly lymphopoiesis, is fragmentary. HGF has been proposed to regulate hematopoiesis in mouse fetal liver and adult bone marrow in vivo, where it apparently can substitute for the stem cell factor (SCF) and c-kit system. HGF is produced by bone marrow (BM) stromal cells and synergizes with IL-3 or GMCSF to support the growth of hemopoietic progenitor cells (HPCs) and myeloid tumor cell lines, all of which express the HGF receptor, c-MET. In the presence of erythropoietin, HGF induces the formation of colonies along the erythroid lineage, whereas in the presence of erythropoietin plus SCF, HGF supports the growth of multipotent colonies. Similarly, upregulation of the HGF receptor on primitive hematopoietic cells may be induced by IL-11; and the synergistic interaction of these two cytokines may result in in vitro colony formation by hemopoietic stem cells (HSCs). However, HGF alone does not appear to stimulate proliferation of hemopoietic precursors. The latter may be attributed to enhancement by HGF of signal transduction by lineage-specific cytokines.

HGF has been found to promote adhesion of HPCs to fibronectin in vitro, and may be involved in a novel paracrine signaling pathway regulating integrin-mediated adhesion and migration of B cells in germinal centers. Messenger-RNA for c-MET has been identified in thymocytes as well as in early B-lineage cells in bone marrow. It is hypothesized that HGF may be involved in a novel paracrine signaling pathway that regulates integrin-mediated adhesion and migration of B-cells in germinal centers. Thus, HGF may be one of the long sought mediators of paracrine interactions between stromal and lymphohematopoietic cells. Furthermore, HGF seems to preferentially affect hematopoietic cells in a window of differentiation between multipotent progenitors and committed precursors. For example, the addition of HGF to fetal thymus organ cultures is known to increase the generation of mature T cells.

Interleukins are a class of proteins that induce growth and differentiation of lymphocytes and hematopoetic stem cells. One interleukin in particular, IL-7, has been demonstrated over the past decade to have an essential role in the development and differentiation of murine pre-B cells.

The nature of IL-7 involvement (if any) at earlier stages of B cell development remains controversial. While it has been proposed that IL-7 is capable of acting on primitive B220⁻ B cell progenitors in the presence of stem cell factor (SCF), most investigators have concluded that the principle B-lineage targets for IL-7 are pro-B cells and pre-B cells. The pre-B cells that do appear in IL-7 KO mice are abnormal as evidenced by their failure to up-regulate or express IL-7R-alpha, TdT and cµ. However, some redundancy may exist between the activities of IL-3, TSLP, and IL-7. Additionally, it has been suggested that the short-term maintenance of pre-pro-B cells, but not pro-B cells, depends on contact-mediated signals from BM stromal cells. Thus, in vivo treatment of mice with anti-IL-7 antibodies eliminates B-lineage subsets as early as the pro-B, but not the pre-pro-B, cell stage; a similar maturational arrest has been observed in mice having disrupted IL-7R-alpha chain genes (IL-7R-alpha −/−); and the Tyr449 to Phe-alpha chain point mutation suggests that the IL-7R transmits distinct signals for cell proliferation and IgH gene rearrangement. In contrast, von Freeden-Jeffry et al. (*D. Exp. Med.* 181: 1519 (1995)) found that both pre-pro-B cells and pro-B cells are well represented in BM of IL-7 gene-deleted mice; and Pribyl and LeBien (*Proc. Nat. Acad. Sci. USA* 93: 10348 (1996)) have reported that human B-lineage cells can be generated from fetal precursors in an IL-7-independent manner.

It must be cautioned that the presence of pre-pro-B cells in IL-7R-alpha chain (−/−) mice does not necessarily preclude the involvement of IL-7 at this developmental stage in normal animals. An alternative explanation is that the immediate precursors of pre-pro-B cells do not require an IL-7R-mediated signal to generate pre-pro-B cells. It must also be cautioned that the presence of pro-B cells in IL-7 gene-deleted mice does not exclude a physiological role for IL-7 in early B-lineage development; neither does it preclude the possibility that cytokines other than IL-7 use the IL-7R to stimulate proliferation and differentiation of early B-lineage precursors. Indeed, our recent studies in IL-7 KO mice have demonstrated that IL-7 is essential for upregulation of TdT and IL-7R-alpha chain expression among early pro-B cells and for initiation of cμ expression in late pro-B cells. Therefore, while pro-B cell development occurs in IL-7 KO mice, such development is abnormal. Similar explanations may apply to conflicting reports regarding the need for IL-7 in normal human B cell ontogeny, although important species-specific differences may exist.

In prior studies, the present inventors have demonstrated that serum-free BM stromal cell conditioned medium (CM), as described in Nakumra et al., *Nature* 342: 440-443 (1989); Rubin et al., *Biophysica Acta* 1155: 357-371 (1993); and Zarnegar et al., *J. Cell Biol.* 129: 1177-1180 (1995), selectively stimulates the proliferation of early (TdT⁻) and late (TdT⁺) pre-pro-B cells from freshly-harvested rat BM and supports the generation (but not the proliferation) of pro-B cells. Furthermore, adsorption of CM with anti-IL-7 mAb removes this activity, whereas rIL-7 restores this activity to medium conditioned by BM stromal cells from IL-7 gene-deleted mice (−/− CM). Nonetheless, anti-IL-7 mAb is unable to neutralize the pre-pro-B cell growth-stimulating activity in IL-7 (+/+) CM or in rIL-7-supplemented (−/−) CM; and rIL-7, is unable to restore PPBSF activity to IL-7 (+/+) CM that has been adsorbed with anti-IL-7 mAb. The reason for these finding are not explained by the prior art discussed above.

SUMMARY OF THE INVENTION

The present invention relates to the inventors' discovery that the unique lymphopoietic properties of BM lymphoid cells is due to the presence of a self-assembling molecular complex of IL-7 (SEQ ID NO:7 and 8) and a second stromal cell-derived factor; a molecular complex previously unrecognized in the art. Biological properties of the self-assembling molecular complex, designated pre-pro-B cell growth stimulating factor, suggest widespread medical applications.

Western blot analysis under reducing and nonreducing conditions directly demonstrates that PPBSF is a covalently-bound, 55 kDa, heterodimer. The heterodimer comprises a non-IL-7 co-factor (coF) of about 30 kDa (determined using monoclonal antibodies derived from PPBSF-immunized IL-7 KO mice). PPBSF-coF is constitutively produced by BM stromal cells from IL-7 K/O mice cultured under pro-B cell but not pre-B cell (i.e. Whitlock/Witte-type culture conditions), and "primes" pre-pro-B cells to proliferate in response to monomeric IL-7 in an anchorage-independent fashion by upregulating the expression of the IL-7R-alpha chain.

By both amino acid sequence analysis and reciprocal Western immunoblotting, it was discovered that the PPBSF-coF of PPBSF is the beta-chain of HGF (also described herein as "HGF-beta"; SEQ ID NOs: 3, 4, 13). In confirmation of the same, the bioactivity of native PPBSF has been found to be neutralized by antibodies to the HGF-beta chain (i.e., Val 496 to the end of the full length HGF protein; SEQ ID NO:14). Although cDNA for pro-HGF had previously been cloned prior to the present invention, the beta-chain cDNA had not been isolated and cloned into appropriate expression vectors.

PCR amplification of the coding sequence of HGF (SEQ ID NO:11) in stromal cells from IL-7 KO mice resulted in the application of two transcripts of 2230 and 840 bp. The smaller product showing complete homology with the published mouse HGF-beta gene was subcloned into the mammalian expression vector pcDNA3.1 (+) and transfected into Chinese hamster ovary (CHO) cells. The HGF-beta gene was also subcloned into the prokaryotic fusion protein expression vector pCAL-n and transformed into *E. coli* BL21 (DE3).

The rHGF-beta DNA was purified by calmodulin affinity resin. Unexpectedly, rIL-7 (SEQ ID NO:8) spontaneously complexed with rHGF-beta (SEQ ID NOs:3, and 4) in the presence of low molecular weight heparin sulfate (HS)-derived oligosaccharides (below about 3000 Dalton) to form a heterodimer having the functional activity of native PPBSF. However, because several naturally occurring variants of HGF-beta produced by alternative splicing of the HGF gene have been identified, the precise form of HGF-beta represented in PPBSF may vary. Therefore, in certain embodiments the chimera of the invention comprises a cytokine portion comprising 70%, 75%, 80%, 85%, or 95% homology to a peptide having a amino acid sequence of at least one of SEQ ID NOs: 3, 4, 13, or 14.

This is the first demonstration of a naturally occurring hybrid cytokine (i.e. a biomolecular or unimolecular complex of the bioactive portions of two or more disparate cytokines or growth factors). It also is the first demonstration of a bioactive form of IL-7 (SEQ ID NO:7, 8) and HGF-beta (SEQ ID NO:3, 4, 13, and 14) that selectively supports the proliferation and subsequent differentiation of pre-pro-B cells. Although IL-7 plays an essential role in the development of early B lymphocytes, IL-7 alone doesn't support the proliferation of pre-pro-B cells, and while HGF can synergize with IL-3, GM-CSF or erythropoietin to support the growth of HPCs, myeloid cell lines, and erythroid cells, respectively, it has not been reported to play a direct role in the early B-cell development.

Hence, the discovery of the IL-7/HGF-beta complex not only provides a reagent that regulates the earliest stages of B-lymphocyte development in bone marrow, but it may presage the existence of a series of other naturally occurring hybrid cytokines as well as the artificial creation of hybrid cytokines with unique pharmacological properties. In addition, the existence/creation of hybrid cytokines may render pleiotropic growth factors lineage-specific, thereby directing the commitment of hemopoietic and other pluripotent stem cells to development along selective pathways.

"IL-7/HGF-beta complex," as used herein, refers both to a bimolecular protein complex which features both the IL-7 (Interleukin-7) and HGF-beta polypeptides, and biologically-active variants thereof, as well as and a unimolecular protein which includes the bioactive portions of IL-7 and HGF-beta connected within a single, contiguous polypeptide chain (i.e., chimeric IL-7/HGF-beta). In any of the embodiments described herein the term "linker" relates to linkers of any kind, which are suitable for the binding of polypeptides. Examples of such linkers include but are not limited to a disulfide-bridge connecting amino acids from both polypeptides; heparin or heparan sulfate-derived oligosaccharides (glycosoaminoglycans) connecting both polypeptides; bifunctional or chemical cross-linkers; and a peptide or polypeptide linker. The unimolecular protein can also be a chimera or fusion polypeptide. For example, a polypeptide featuring the bioactive portions of IL-7 and HGF-beta can be fused with each other, either directly or through a linker. In certain aspects the chimeric IL-7/HGF-beta polypeptide comprises an amino acid linker sequence of from 1 to about 100 amino acids. In other aspects the linker introduces flexibility into the chimeric polypeptide in order to relieve steric hindrance.

PPBSF has been found to selectively stimulate the proliferation of pre-pro-B cells and to support the generation of pro-B cells (the next recognized stage in early B-lymphocyte development). PPBSF "primes" pre-pro-B cells to proliferate in response to monomeric IL-7 (SEQ ID NO:7, 8) in an anchorage-independent fashion by upregulating the expression of the IL-7R-alpha chain. PPBSF also upregulates the expression of terminal deoxynucleotidyl transferase (TdT) and initiates the expression of cytoplasmic immunoglobulin m1 heavy chain (cμ). PPBSF also stimulates the proliferation of thymocytes.

The IL-7/HGF-beta complex can be isolated from natural sources, e.g., mammalian tissues or cell lines which are known to be a source of cytokines or growth factors. It may also be formed from recombinant and/or natural components as shown herein. PPBSF was shown to be expressed by bone marrow stromal cells in our pro-B cell culture system. Alternatively, PPBSF can be reconstituted from products of prokaryotic or eukaryotic expression of exogenous DNA sequences i.e., derived by recombinant means.

The present invention also includes biologically-active variants of the IL-7 or HGF-beta complex. Such variants include any homologs, orthologs, paralogs, and homologous peptides to either IL-7 (SEQ ID NO:7, 8) or HGF-beta (SEQ ID NO:3, 4, 13, and 14; See FIGS. 37 and 38), for example including substitution analogs wherein one or more amino acids have been substituted with different amino acids, deletion analogs wherein one or more amino acids have been deleted, and addition analogs wherein one or more amino acids have been added. Deletions and additions of one or more amino acids are made either within an internal region of the polypeptide or at the amino or carboxyl terminal ends. Additional potential variations include other heterodimeric (or multimeric) cytokine complexes containing IL-7 and/or HGF (alpha and/or beta chains), and other hybrid cytokines unrelated to either IL-7 or HGF, whether naturally occurring or artificially created, including those that bind to the receptors for HGF, IL-7, and/or γc.

Western immunoblotting showed that PPBSF was a covalently-linked heterodimer of IL-7 (SEQ ID NO:8) and an 30 kDa cofactor. Partial amino-terminal amino acid sequence analysis of purified PPBSF cofactor showed the first 15 of 17 amino acid residues were identical to the published sequence of mouse HGF-beta chain (SEQ ID NO:3, 4). Western blot analysis confirmed the identity of PPBSF cofactor as the beta chain of HGF.

In conjunction with the invention, the present inventors have: (1) established a pro-B cell culture system that selectively generates large number of pre-pro-B cells and pro-B cells from rat, mouse and human bone marrow; (2) demonstrated that medium conditioned by BM stromal cells in our pro-B cell culture system selectively supports the development of pre-pro-B cells and pro-B cells in vitro; (3) demonstrated the existence in conditioned medium of a non-IL-7 component of PPBSF by anti-IL-7 antibody neutralization and adsorption experiments; (4) demonstrated that PPBSF is a covalently-linked heterodimer of IL-7 and a 30 kDa cofactor by Western immunoblot analysis under reducing and non-reducing conditions; (5) demonstrated that PPBSF is a self-aggregating complex of IL-7 and a 30 kDa cofactor by addition of IL-7 to conditioned medium from IL-7 gene-deleted mice; (6) demonstrated that PPBSF, but not IL-7 or PPBSF cofactor alone, upregulates the expression of IL-7R-alpha, TdT and cμ on/in pro-B cells from IL-7 gene-deleted mice and "primes" then to proliferate in response to monomeric IL-7; (7) developed neutralizing monoclonal antibodies specific for the PPBSF cofactor; (8) identified the PPBSF cofactor as the beta chain of HGF/SF by amino acid analyses and reciprocal Western blotting; (9) cloned the HGF-beta cDNA into mammalian and prokaryotic expression vectors and expressed the protein in mammalian (CHO) and prokaryotic *E. coli* BL21 (DE3) cells; (10) demonstrated that rIL-7 spontaneously complexes with rHGF-beta in the presence of low molecular weight heparin sulfate (HS)-derived oligosaccharides to form a heterodimer having the functional activity of native PPBSF; and (11) created a chimeric IL-7/HGF-beta nucleic acid fusion construct, expressed it as a single-chain protein, and demonstrated its efficacy and stability.

In a further aspect, the present invention is based on the observation that complexes of recombinant IL-7 (SEQ ID NO:7, 8) and HGF-beta (SEQ ID NO:3, 4, 13, and 14) formed in the presence of heparan sulfate-derived oligosaccharides are less stable then native IL-7/HGF-beta complexes. Without being limited to any particular theory, the inventors believe that the instability observed with the recombinant IL-7/HGF-beta complex is due to incomplete glycosylation. The instability of the recombinant IL-7/HGF-beta complex also makes it difficult to purify sufficient IL-7/HGF-beta for large-scale in vitro or in vivo use. As such, the present invention relates to a chimeric or single-chain polypeptide version of the IL-7/HGF-beta hybrid molecule. The chimeric IL-7/HGF-beta polypeptide, methods of its creation, and efficacy have been demonstrated by Lai et al. (A recombinant single-chain IL-7/HGF-beta hybrid cytokine induces juxtacrine interactions of the IL-7 and HGF (c-Met) receptors and stimulates the proliferation of CFU-$S_{12}$, CLPs, and pre-pro-B cells. *Blood.* 2006; 107:1776-1784), which is incorporated herein by reference in its entirety for all purposes.

Unlike recombinant IL-7 (SEQ ID NO:7, 8), which stimulated pro-B cells and pre-B cells only, the chimeric or single-chain (sc) IL-7/HGF-beta stimulated the proliferation of pre-pro-B cells, common lymphoid progenitors (CLPs), and colony-forming unit (CFU)-$S_{12}$ in cultures of IL-7 (−/−) mouse bone marrow (BM) cells. When injected in vivo, 3- to 4-fold more splenic B-lineage cells appeared in recipients of BM cells from the scIL-7/HGF-beta-stimulated cultures than from rIL-7-stimulated cultures. Moreover, on a per-cell basis, scIL-7/HGF-beta culture-generated cells produced 16- to 20-fold more BM and splenic B-lineage cells than did normal BM cells. Antibody blocking, receptor phosphorylation, and confocal microscopy demonstrated that scIL-7/HGF-beta signals though both the IL-7 and HGF (c-Met) receptors, which form IL-7R/c-Met complexes on the surface of CLPs and pre-pro-B cells. In addition, the IL-7R-alpha chain, γC chain, and c-Met were coisolated from purified CLPs and pre-pro-B cells on scIL-7/HGF-beta affinity gels, indicating that they are major components of the IL-7/HGF-beta receptor. Hence, the present results demonstrate that the IL-7/HGF-beta chimeric cytokine efficiently and selectively stimulates the most primitive B-lineage precursors in BM by inducing juxtacrine interactions between the IL-7 and c-Met receptors.

In certain aspects, the invention relates to a nucleic acid encoding, within a single open-reading frame, an IL-7 (SEQ ID NO:7, 8, 10, and 12) polypeptide or active portion thereof contiguous with an HGF-beta polypeptide (SEQ ID NO:3, 4, 13, and 14) or active portion thereof. In another aspect, the chimeric IL-7/HGF-beta nucleic acid further comprises a polynucleotide linker sequence encoding from 1 to 100 amino acids, which is disposed between the IL-7 encoding polynucleotide (SEQ ID NO:10, 12) and the HGF-beta encoding polynucleotide (See SEQ ID NO:11, 12). In any of the embodiments of the chimeric nucleic acid of the invention, the polynucleotide encoding IL-7 can be positioned 5' of the HGF-beta polynucleotide, and/or the linker polynucleotide. In an alternative embodiment, the HGF-beta polynucleotide is positioned 5' of the IL-7 polynucleotide, and/or the linker polynucleotide.

In other aspects the chimeric IL-7/HGF-beta nucleic acid of the invention is disposed in a vector, plasmid, or artificial chromosome nucleic acid for its convenient cloning, amplification, transcription, and/or translation. In still other aspects the chimeric IL-7/HGF-beta nucleic acid of the invention is operably linked to one or more transcription regulatory nucleic acid sequences. The vector or plasmid nucleic acids can also be stably integrated into the host cell's genome or maintained episomally.

In a another aspect, the vector, plasmid or artificial chromosome is suitable for expression in a prokaryotic or eukaryotic cell; for example, an insect cell, a mammalian cell, a plant cell, or a bacterial cell. In certain embodiments, the invention relates to a host cell comprising the chimeric IL-7/HGF-beta nucleic acid sequence of the invention. In certain aspects, the host cell further comprises a vector or plasmid nucleic acid containing one or more transcription regulatory nucleic acid sequences operably linked with the chimeric IL-7/HGF-beta nucleic acid sequence of the invention. In another aspect, the invention comprises a host cell that has been modified to overexpress IL-7, HGF or both. In other aspects a nucleic acid vector or plasmid containing a chimeric IL-7/HGF-beta nucleic acid is transformed or transfected into the host cell allowing for transient, stable or inducible expression of the chimeric IL-7/HGF-beta polypeptide. In another aspect, the invention relates to a host cell overexpressing IL-7 and/or HGF-beta protein, in which an exogenous promoter or enhancer has been inserted via homologous recombination into the target gene operon to result in increased, or inducible protein expression. In other aspects, the endogenous, i.e., naturally occurring, target gene promoter or enhancer is modified or mutated to result in enhanced or inducible expression of chimeric IL-7/HGF-beta polypeptide.

In another aspect, the invention relates to an antibody which binds specifically to an epitope of a chimeric IL-7/HGF-beta polypeptide. In certain embodiments, the invention also relates to an anti-idiotypic antibody to the heterocomplex receptor that can be used to mimic the activity of the protein complex that can be used as a therapeutic alone or in combination with the chimeric protein of the invention.

In a related aspect, the invention includes a method for producing a chimeric IL-7/HGF-beta protein. In certain embodiments, the process includes providing an IL-7 encoding polynucleotide (SEQ ID NO:10, 12), and an HGF-beta encoding polynucleotide; linking, in a single contiguous polynucleotide chain; the IL-7 and HGF-beta nucleic acids being in a single continuous open-reading frame; inserting the chimeric nucleic acid construct into a vector or plasmid; transforming the vector or plasmid into a suitable host cell capable of expressing the chimeric polypeptide. In certain embodiments, the method also includes the addition of at least one other polynucleotide contiguous and in a single continuous open-reading frame with the chimeric IL-7/HGF-beta nucleic acid, which results in the expression of a fusion protein. The additional polynucleotide can be linked on the 5' or 3' end of the chimeric cytokine or in between the IL-7 and HGF-beta encoding polynucleotides. Fusion protein constructs contemplated by the present invention include, for example, peptide moieties useful for protein isolation and purification such as GST, fluorescent proteins, multiple histidine residues, antibody epitope tags, a cell sorting signal sequence, and the like. Other fusion constructs may include nucleic acid sequences encoding one or more amino acids that links the two polypeptides and reduces steric or allosteric hindrance.

In certain aspects, the chimeric IL-7/HGF-beta polypeptide comprises at least one modified amino acid. Amino acid modifications contemplated by the present invention include, for example, phosphorylation, acetylation, methylation; indolizidinone amino acids, D-amino acids, amino acid mimetics, amino acid analogs, etc.

In other aspects the invention relates to methods of inducing the proliferation or differentiation of hematopoietic precursor cells comprising administration of an effective amount of a chimeric IL-7/HGF-beta polypeptide to a B cell precursor, for example, a pre-pro-B cell.

In other aspects, the invention relates to methods for treating and/or preventing a disease or condition in an individual related to the detrimental effects of improper B cell proliferation and/or differentiation. In certain embodiments, the methods of the invention comprise administering an effective amount of a chimeric IL-7/HGF-beta polypeptide in a pharmaceutically acceptable form to an individual in need thereof. In certain embodiments, the chimeric IL-7/HGF-beta polypeptide of the invention is administered together with a pharmaceutically acceptable carrier, excipient, adjuvant, amino acid, peptide, polypeptide, chemical compound, drug, biologically active agent or a combination thereof. As such, in another aspect the invention relates to therapeutic compositions comprising the chimeric IL-7/HGF-beta polypeptide of the invention in a pharmaceutically acceptable form together with at least one pharmaceutically acceptable carrier, excipient, adjuvant, amino acid, peptide, polypeptide, chemical compound, drug, biologically active agent or a combination thereof.

In certain embodiments the therapeutic chimeric IL-7/HGF-beta polypeptide of the invention is complexed, bound, or conjugated to one or more chemical moieties to improve and/or modify, for example, bioavailability, half-life, efficacy, and/or targeting. In certain aspects of this embodiment, the chimeric IL-7/HGF-beta polypeptide may be complexed or bound, either covalently or non-covalently with, for example, cationic molecules, salts or ions, lipids, glycerides, carbohydrates, amino acids, peptides, proteins, other chemical compounds, for example, phenolic compounds, and combinations thereof. In certain aspects the invention relates to a chimeric IL-7/HGF-beta polypeptide of the invention conjugated to a polypeptide, for example, an antibody. In certain embodiments the antibody is specific for a protein target at or near the receptor complex for the IL-7/HGF-beta hybrid molecule.

The therapeutic chimeric IL-7/HGF-beta polypeptide of the invention can be administered by any suitable route recognized by those of skill in the art, for example, enteral, intravenous, intra-arterial, parenteral, topical, transdermal, nasal, and the like. In addition, the therapeutic may be in any pharmaceutically acceptable form such as, for example, a liquid, lyophilized powder, gel, pill, controlled release capsule, and the like, which is now known or becomes known to those of skill in the art.

Additional advantageous features and functionalities associated with the compositions, methods, and processes of the present invention will be apparent from the drawings presented herein, as well as the detailed description which follows. The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The accompanying figures, which are incorporated in and constitute part of the specification, illustrate presently preferred embodiments of the invention, and together with the general description given above and the detailed description of the preferred embodiments given below, serve to explain the principles of the invention.

FIG. 13 is a partial NH2-terminal amino acid sequence identity of purified mouse PPBSF cofactor, and its comparison with the published sequence for the HGF-beta chain in mouse (SEQ ID NO:3, 4).

FIG. 37 Homologs of Human Hepatocyte Growth Factor (SEQ ID NO:5) Identified by BLASTP. Queried sequence contained the full length human hepatocyte growth factor (HGF) polypeptide; i.e., contains both alpha and beta chains (full length: V495 to S728 (SEQ ID NO:14); active peptide: V495-L511 (SEQ ID NO:13) (NCBI Accession: BAA14348; 728 aa). A. indicates homologous domain structure between human HGF and homologous proteins; B. list of HGF homologs including accession number, annotated name/description, and homology score.

FIG. 38 Homologs of Human IL-7 (SEQ ID NO:7) Identified by BLASTP. Queried sequence contained the full length human IL-7 polypeptide; (NCBI Accession: NP_000871; 177aa). A. indicates homologous domain structure between human IL-7 and homologous proteins; B. list of IL-7 homologs including accession number, annotated name/description, and homology score.

DETAILED DESCRIPTION OF THE INVENTION

Figures 1A, 1B, 1C, 1D:
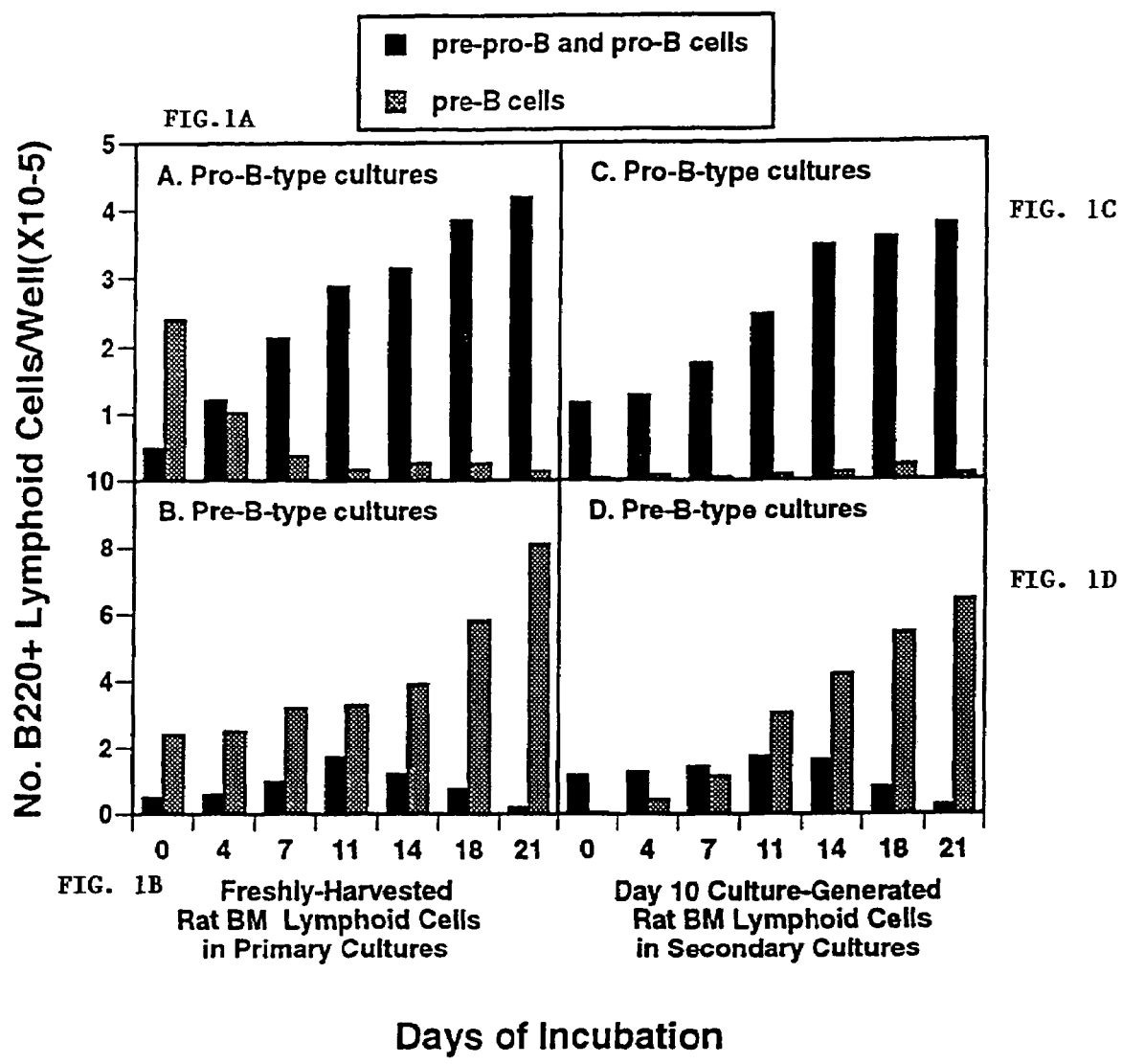
FIG. 1A-FIG. 1D are bar graphs of the number of pre-pro-B and pro-B cells versus pre-B cells derived from rat bone marrow lymphoid cells grown in a pro-B type culture as described (FIGS. 1A and 1C) and pre-B type culture (Whitlock/Witte) (FIGS. 1B and 1D) over a twenty-one day period emanating from either freshly-harvested cells in primary culture (FIGS. 1A and 1B) or emanating from day 10 culture-generated rat bone marrow lymphoid cells in secondary culture (FIGS. 1C and 1D).

The present invention relates to the discovery that certain stromal cell-derived cytokines form hybrid molecules that regulate pro-B and pre-B cell development in bone marrow.

As used herein, the term "cytokine" is used generally to refer to a broad class of biologically active peptides or polypeptides including cytokines, lymphokines, chemokines, growth factors, interleukins, interferons, and the like. Cytokines are characterized by considerable "redundancy", in that many cytokines can share similar functions. In a comparable manner, cytokines are also pleiotropic (acting on many different cell types). As such, a given cell type may express receptors for more than one cytokine, and/or different tissues can express receptors for the same cytokine. The biological actions of cytokines can be characterized generally as either autocrine (the cytokine acts on the cell that secretes it); paracrine (the action is restricted to the immediate vicinity of a cytokine's secretion); endocrine (the cytokine diffuses to distant regions of the body (carried by blood or plasma) to affect different tissues); or exocrine (if the cytokine is secreted or stored in a duct for delivery to a specific site of action).

In addition, as used herein, "cytokine polypeptides," encompasses recombinant full length or pre-pro-polypeptide forms, pro-polypeptide forms, the mature or processed polypeptide forms, as well as the biologically active forms, including naturally occurring or recombinantly made truncations or portions derived from the full length polypeptides. Furthermore, polypeptides of the invention may include amino acid mimetics, and analogs. Recombinant forms of the chimeric polypeptides can be produced according to standard methods and protocols which are well known to those of skill in the art, including for example, expression of recombinant proteins in prokaryotic and/or eukaryotic cells followed by one or more isolation and purification steps, and/or chemically synthesizing cytokine polypeptides or portions thereof using a peptide synthesizer.

As used herein, "biologically active" refers to the ability of a cytokine to effectuate a physiological change or response. The response may be detected, for example, at the cellular level, for example, as a change in gene expression, protein quantity, protein modification, protein activity, or combination thereof; at the tissue level; at the systemic level; or at the organism level. Techniques used to monitor these phenotypic changes include, for example, measuring: the binding of a ligand to its receptor in or on a cell, activation of cell signaling pathways, stimulation or activation of a cellular response, secretion or release of bioactive molecules from the cell, cellular proliferation and/or differentiation, or a combination thereof.

Using a long-term lymphoid BM culture system (LTBMC) (as described in Nakumra et al., Nature 342: 440-443 (1989), Rubin et al., Biophysica Acta 1155: 357-371 (1993) and Zarnegar et al., J. Cell Biol. 129: 1177-1180 (1995)) that selectively supports the proliferation, self-replication and differentiation of pre-pro-B cells from rat, mouse and human BM, monoclonal antibodies were raised to a novel IL-7-associated growth factor that selectively stimulates proliferation of pre-pro-B cells and supports their differentiation to pro-B cells. As revealed by Western blot analysis, amino acid sequencing and molecular cloning, this naturally occurring pre-pro-B cell growth stimulating factor, is a covalently-bound heterodimer of IL-7 (SEQ ID NO:7, 8) and the beta-chain of hepatocyte growth factor (HGF) (SEQ ID NO:3, 4, 13, and 14).

This is the first demonstration of any hybrid cytokine (possibly aside from IL-12, which is structurally analogous to a disulfide-linked secreted complex of a cytokine with a cytokine receptor), and suggests a new paradigm by which pleiotropic cytokines (in this case HGF) can be rendered organ, tissue, lineage or stage-specific; and by which the functions of organ, tissue, lineage or stage-specific cytokines (in this case, IL-7) can be enhanced or altered. It also suggests a paradigm by which commitment of hemopoietic stem cells to development along a particular cell lineage may be regulated by such hybrid cytokines.

The 30 kDa, non-IL-7 component of the PPBSF heterodimer (PPBSF-coF) is disclosed herein as the beta-chain of the hepatocytic growth factor/scatter factor (HGF/SF). In addition, it is demonstrated herein that active artificially-derived PPBSF can be produced by expressing a chimeric polypeptide comprising HGF-beta and IL-7, made by the cloning of the coding sequence of HGF-beta with rIL-7 in a contiguous, single polynucleotide chain. This is a remarkable and wholly unexpected finding, inasmuch as HGF (of which the beta-chain is the mitogenic component) is one of the most important cytokines involved in the regulation of organogenesis in embryonic life and of tissue regeneration and repair in adult life.

Further insights into the probable actions of PPBSF in regulating normal pre-pro-B cell and pro-B cell development in vivo and in vitro have been gained by the present invention. Thus, PPBSF, but not monomeric IL-7, appears to induce pre-pro-B cells and/or pro-B cells to upregulate TdT and IL-7R-alpha and to initiate synthesis of cμ. Subsequently, monomeric IL-7 can stimulate these "primed" pro-B cells to proliferate and generate pre-B cells.

Much of what is known about the microenvironmental regulation of early B cell development stems from the use of long-term in vitro bone marrow culture systems. As discussed above, the present inventors have previously described a long-term lymphoid cell culture system that selectively generates large numbers of pre-pro-B cells and pro-B cells from rat, mouse, and human BM in the presence of mouse BM adherent cells (Nakamura et al., Nature 342: 440-443, 1989; Rubin J S et al. Biophysica Acta 1155: 357-371, 1993; Zarnegar R et al. 1995; J Cell Biol 129: 1177-1180; and Liu et al. Biophysica Acta 1216: 299-303; incorporated herein by reference) referenced herein as the pro-B cell culture. Approximately 50% of the lymphoid cells show partial D-J heavy chain Ig gene rearrangements; whereas the remaining lymphoid cells have a germline configuration, and are themselves derived from even more primitive, B220⁻, precursors. Unlike more traditional LTBMC systems, the pro-B cell culture system, so described, selectively generates pre-pro-B cells and early pro-B cells from adult BM, even when the lymphoid progenitors are separated from the adherent cell layer by a microporous membrane culture insert or cultured in stromal cell conditioned medium (CM). However, under optimal conditions, the "early" (TdT⁻) pre-pro-B cells, adhere tightly to BM stromal cells, and self-replication occurs indefinitely upon serial transfer to new adherent cell layers in vitro. In addition, these pre-pro-B cells produce non-adherent pro-B cells in vitro and rapidly generate sIgM⁺B cells after in vivo transfer. Yet, neither cμ⁺ pre-B cells nor sIgM⁺B cells are produced in significant numbers in vitro, even in the presence of 2-ME.

Although there is no evidence of progressive clonal restriction or leukemic transformation under normal circumstances, the pro-B cell culture system is also able to generate leukemic pre-pro-B cells and pro-B cells in vitro, when seeded with BM cells from rats that have been infected neonatally with the Gross leukemia virus or from human patients with acute lymphoblastic leukemia (ALL). Like their normal counterparts, these B-cell lineage leukemias are dependent upon the presence of a BM adherent cell layer (or conditioned medium therefrom). Moreover, the cells that undergo leukemic transformation co-isolate on the FACS with the precursors that generate normal pro-B cells. They therefore have proved useful as target cells in bioassays for stage specific lymphoid growth-stimulating factors.

The demonstration herein that PPBSF is a heterodimer of IL-7 (SEQ ID NO:7, 8) and the HFG-beta chain (SEQ ID NO:3, 4, 13, and 14) may provide key insights into the mechanisms by which the earliest stages of lymphoid commitment and/or expansion from HSCs in BM are regulated.

It is unclear as to why a hybrid cytokine, in which IL-7 substitutes for the alpha-chain of HFG, selectively supports the proliferation and differentiation of pre-pro-B cells in vitro. The present inventors have hypothesized, but the invention is not limited by such hypothesis, that evolutionarily such activity occurred to address: 1) the need for cognate interactions between pre-pro-B cells and BM stromal cells for optimal lymphopoiesis; 2) the need for self-replication of pre-pro-B cells to maintain the precursor cell pool; 3) the expression of only low levels of high affinity IL-7R. PPBSF can satisfy all of these requirements by stimulating the self-replication of pre-pro-B cells, by functioning primarily as a cell surface (or ECM)-bound molecular complex; and by upregulating IL-7R-alpha-chain expression. Such a role for PPBSF in normal BM provides additional insights into the nature of the cognitive interactions between pre-pro-B cells, BM stromal cells and associated ECM.

Inasmuch as both IL-7 (SEQ ID NO:7, 8) and HGF (SEQ ID NO:5, 6) are avidly-bound by heparin, and are functionally cross-linked by low molecular weight (below about 3000 kD) heparin-sulfate-derived oligosaccharides, it is possible that PPBSF is a component of the stromal cell-associated extracellular matrix that characterizes the culture system. Despite the inability to detect PPBSF activity in extracellular matrix extracted from BM adherent cell layers with hypertonic saline, continued efforts are warranted based on recent reports of the regulation of growth factor signaling by ECM proteins, and especially the description by Oritani and Kincade (J. Cell. Biol. 134: 771-782) of a series of ECM glycoproteins that selectively increase the IL-7-dependent proliferation of pre-B cells.

The sequential expression of low and high concentrations of high affinity IL-7R during early B-lineage development is analogous to events observed during early thymocyte development. Given that pro-B cells from γc gene-deleted mice express only low levels of IL-7R -alpha-chain, IL-7R-alpha KO mice apparently fail to generate pro-B cells, and excess IL-7 fails to increase pre-pro-B cell generation in vivo, it is possible that signal transduction through high affinity IL-7R (alpha/γc) is required to transmit a proliferative signal for pre-pro-B as well as pro-B cells. This is further supported by the inventors' recent observation that, although the IL-7R-alpha is not upregulated on pro-B cells from IL-7 (−/−) mice, its expression can be induced on such cells in vitro by purified PPBSF, but not rIL-7. Hence, PPBSF may favor the association of IL-7R-alpha and γc chains under conditions of low IL-7R-alpha expression, whereas monomeric IL-7 may require high concentrations of IL-7R-alpha.

There appears to be a "priming" effect of PPBSF for monomeric IL-7 (SEQ ID NO:7, 8), wherein PPBSF selectively regulates the $G_1/S$ transition of pre-pro-B cells, and monomeric IL-7 selectively regulates the $G_1/S$ transition of pro-B cells. Such sequential actions of PPBSF and monomeric IL-7 would correlate nicely with the demonstration of separate microanatomical niches, differential adhesion mechanisms, decreasing need for cognitive interactions, and increasing dependency on IL-7 during early B cell development. Compatible conclusions have been reached by Billips et al (Blood 79: 1185 (1992)) using the S17 stromal cell line; and Hayashi et al. (J. Exp. Med. 171: 1683 (1990)), using the PA6 stromal cell line. Even more intriguing is the possibility that PPBSF may be involved in regulating the commitment of HSC to development along the B (and possibly T) lymphoid pathways. Hence, differences in molecular form and, possibly, site of expression may render IL-7 pre-pro-B cell stage-specific; and differences in the receptor-binding domain (IL-7 for HGF-alpha) may render HGF-beta (SEQ ID NO:3, 4, 13, and 14) lymphoid lineage-specific.

Despite the occurrence of early B-lineage development in IL-7 K/O and IL-7R K/O mice, the present inventors postulate that IL-7 (SEQ ID NO:7, 8), in the form of PPBSF, is the preferred ligand under physiological conditions. Furthermore, the present inventors suspect that those compensatory mechanisms that do exist may be suboptimal, given that pro-B cells in IL-7 (−/−) mice do not upregulate TdT or IL-7R-alpha during IgH gene rearrangement, do not initiate cµ expression, and do not proliferate in response to monomeric IL-7. However, once stimulated with PPBSF, TdT and IL-7R-alpha are upregulated, cell proliferation is stimulated by monomeric IL-7, and cµ is expressed, at least in vitro. These results may help to explain why the in vivo administration of anti-IL-7 mAb prevents the development of pro-B cells in normal mice, namely by causing the coordinate elimination of IL-7 and PPBSF.

The present inventors have: 1) defined the microenvironmental anatomy for the contact-dependent phase of pre-pro-B cell and pro-B cell development; 2) traced the parent-progeny relationships of "early" and "late" pre-pro B cells and pro-B cells; and 3) identified a novel 55 kD IL-7-associated heterodimer that appears to regulate the proliferation of pre-pro-B cells, their differentiation to pro-B cells, and their ability to respond to monomeric IL-7 in a contact-independent manner. In addition, they have utilized the IL-7 KO mouse to isolate, purify, and raise monoclonal antibodies to a 30 kD cofactor that spontaneously complexes with IL-7 to form the claimed pre-pro-B cell growth-stimulating factor (PPBSF). The PPBSF-coF is identified by the present inventors as the HGF-beta chain. The present inventors have generated the PPBSF in recombinant form.

Applications

As would be understood by one of ordinary skill in the art, PPBSF could be used alone or in conjunction with other factors to treat a number of hematopoietic disorders in human beings and/or domesticated animals that result from disease or injury to B-lineage (and other) cells in bone marrow. These include the following: pancytopenia, myelodysplastic syndrome, leukemias and lymphomas, hereditary or acquired immunodeficiency disorders, and myelosuppression resulting from radiation treatment, chemotherapy, drug allergies, or environmental toxins. PPBSF may also be useful in expanding and/or enhancing engraftment of B-lineage progenitor cells in vivo syngeneic, allogeneic or autologous bone marrow transplantation, or ex vivo in marrow or HSC cultures prior to transplantation. Further, it would be expected that such treatment will reduce the period of depressed immunity due to delayed B cell regeneration that frequently is experienced by patients after transplantation. Also, PPBSF may enhance the engraftment of genomically modified B-cell precursors in the treatment of selected immunodeficiency and leukemic disorders. In addition, PPBSF may be used to enhance the growth of leukemic B-lineage cells in vitro to permit customized screening profiles of chemotherapeutic and immunotherapeutic sensitivity to be developed for individual patients, or to permit individualized tumor vaccines to be produced. Furthermore, a deficiency or abnormality of PPBSF itself may prove to be a cause of immunodeficiency in some patients, making screening assays for PPBSF useful.

In bone marrow transplantation, the PPBSF may be used to pretreat the marrow prior to transplantation and/or may be administered in vivo after transplantation. The PPBSF may be used as a pharmacological agent itself or introduced by way of a transformed cell, viral vector, etc. PPBSF proffers significant therapeutic advantages to the bone marrow recipients in that it substantially increases lymphocyte precursors. Bone marrow recipients usually take months to approach normal levels of B and T-lymphocytes after transplantation. PPBSF has been seen not only to stimulate parental cells to generate large numbers of mature progeny, but to produce more parental cells (self-replication), leading to long-term engraftment.

Animal studies suggest that the chimeric cytokine of the present invention may have particularly usefulness in the treatment of acute lymphoblastic leukemia in that it has been found to proliferate leukemic as well as normal cells. By administering PPBSF to leukemic patients the malignant cells can be activated to proliferate. As most chemotherapeutic agents today are designed to selectively kill dividing cells, such chemotherapeutic agents in conjunction with PPBSF provide a better "kill rate" of the malignant cells (a certain portion of the population of malignant cells usually are non-dividing at time of chemotherapy and therefore are protected from the cytotoxic effect of the chemotherapeutic agents).

Inasmuch as well as PPBSF also stimulates proliferation of immature thymocytes, it may prove to be equally useful in treating disorders of T lymphocytes as well as B lymphocytes. Indeed, should PPBSF induce commitment of HSC to bipotential lymphoid differentiation, it could be used to correct severe combined immunodeficiency disorders, possibly including AIDS.

PPBSF can also be used in vitro to screen the blood and other tissues of patients treated with chemotherapy to determine whether malignant lymphocytes still exist, that is, by increasing the pool of malignant lymphocytes in a sample allowing for easier detection of the same. PPBSF may also be used to establish cultures of leukemic cells from individuals which may be used in screening assays for panels of chemotherapeutic agents. An additional potential use of hybrid cytokines, containing HGF-beta or other pleiotropic growth factors complexed with organ, tissue, lineage or stage-specific cytokines, is to direct the differentiation of embryonic stem cells along specific pathways in vitro for organ, tissue or cell transplantation purposes and/or to induce regeneration of damaged organs, tissues or cell lineages in vivo.

The ability of the pro-B cell culture previously described by the present inventors' (see above) to sustain leukemic pre-pro-B cells and pro-B cells from the BM of human patients with acute lymphoblastic leukemia suggests that the growth of these cells may also be regulated, at least in part, by PPBSF. Abnormalities in pro-B cell development can also be reproduced in cultures of BM cells from several murine models of autoimmunity and immunodeficiency. The ability to selectively generate pre-pro-B cells in vitro provides a unique opportunity to determine the nature of the microenvironmental cells and factors that regulate normal and abnormal lymphopoiesis at this critical stage of development.

Chimeric and Fusion Proteins

As described supra, the invention also provides chimeric or fusion proteins. As used herein, a "chimeric protein" or "fusion protein" comprises a polypeptide operatively-linked to another polypeptide, for example, one or more of the polypeptides chosen from SEQ ID NOs: 3-8, 13, or 14, or portions thereof. Whereas the polypeptides chosen from SEQ ID NOs: 3-8, 13, or 14 include polypeptides having an amino acid sequence with at least 30% homology. Within the fusion protein the polypeptide can correspond to all or a portion of a polypeptide chosen from SEQ ID NOs: 3-8, 13, or 14. In one embodiment, the fusion protein comprises at least one biologically active portion of the protein chosen from SEQ ID NOs: 3-8, 13, or 14. Within the fusion protein, the discrete polypeptides are fused in-frame with one another at the N-terminus or C-terminus.

In more than one embodiment of the above assay methods, it may be desirable to immobilize the chimeric polypeptides of the invention to facilitate separation of the proteins. In one embodiment, a fusion protein can be provided which adds a domain that allows the proteins to be bound to a matrix. For example, glutathione-S-transferase fusion proteins or conjugation of biotin and streptavidin. In one embodiment, the fusion protein is a GST-fusion protein in which the polypeptide sequences are fused to the C-terminus or N-terminus of the GST (glutathione S-transferase) sequences. In another embodiment, the fusion protein contains a heterologous signal sequence at its N-terminus. In certain host cells (e.g., mammalian host cells), expression and/or secretion can be increased through use of a heterologous signal sequence. In yet another embodiment, the fusion protein is immunoglobulin fusion protein in which the polypeptides or polypeptide complex of the invention is fused to sequences derived from a member of the immunoglobulin protein family. In one embodiment, the immunoglobulin fusion proteins of the invention can be incorporated into pharmaceutical compositions and administered to a subject to modulate an interaction between a ligand and a protein on the surface of a cell. The immunoglobulin fusion proteins can be used to affect the bioavailability of a cognate ligand. Inhibition of the ligand interaction may be useful therapeutically for both the treatment of proliferative and differentiative disorders, as well as modulating (e.g. promoting or inhibiting) cell survival. Moreover, the immunoglobulin fusion proteins of the invention can be used as immunogens to produce antibodies in a subject, to purify ligands, and in screening assays to identify molecules that inhibit the interaction.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). One or more of SEQ ID NOs: 9-12, or portions thereof, can be cloned into such an expression vector such that the fusion moiety is linked in-frame to the desired polypeptide.

Antibodies

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')2 fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids of SEQ ID NOs: 3-8, 13, or 14. In certain embodiments, the present invention comprises antibodies that recognize and are specific for one or more epitopes of any of SEQ ID NOs: 3-8, 13, or 14, variants, portions and/or combinations thereof. In other embodiments, the antibodies of the invention may be specific for the cytokine receptor complex itself. In still other embodiments an antibody specific for the chimeric cytokine of the invention may function as the "receptor"—i.e., functioning in a transpresentation mechanism. In alternative embodiments antibodies of the invention may target and interfere with the chimeric cytokine/receptor interaction to inhibit signaling.

The preparation of polyclonal antibodies is well known in the molecular biology art; see for example, Production of Polyclonal Antisera in Immunochemical Processes (Manson, ed.), pages 1-5 (Humana Press 1992) and Coligan et al., Production of Polyclonal Antisera in Rabbits, Rats, Mice and Hamsters in Current Protocols in Immunology, section 2.4.1 (1992). The preparation of monoclonal antibodies is also well known in the art; see for example, Harlow et al., Antibodies: A Laboratory Manual, page 726 (Cold Spring Harbor Pub. 1988).

Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind to SEQ ID NOs: 5-12 or fragments thereof (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J. 12:725-734; Hawkins et al. (1992) J Mol Biol 226:889-896; Clackson et al. (1991) Nature 352: 624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982).

Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368: 856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

A therapeutically useful antibody to the components of the complex of the invention or the complex itself may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., Nature 321: 522, 1986 and Singer et al., J. Immunol. 150: 2844, 1993. The antibodies can also be derived from human antibody fragments isolated from a combinatorial immunoglobulin library; see, for example, Barbas et al., Methods: A Companion to Methods in Enzymology 2, 119, 1991.

In addition, chimeric antibodies can be obtained by splicing the genes from a mouse antibody molecule with appropriate antigen specificity together with genes from a human antibody molecule of appropriate biological specificity; see, for example, Takeda et al., Nature 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of SEQ ID NOs: 3-8, 13, or 14 that is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol. 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10:779-783 (1992)); Lonberg et al. (Nature 368: 856-859 (1994)); Morrison (Nature 368:812-13 (1994)); Fishwild et al, (Nature Biotechnology 14:845-51 (1996)); Neuberger (Nature Biotechnology 14:826 (1996)); and Lonberg and Huszar (Intern. Rev. Immunol. 13:65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121-210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')2 bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcgammaR), such as FcgammaRI (CD64), FcgammaRII (CD32) and FcgammaRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate). Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" for utilization in tumor pretargeting wherein the antibody-receptor conjugate is administered to the patient, followed by removal of unbound conjugate from the circulation using a clearing agent and then administration of a "ligand" that is in turn conjugated to a cytotoxic agent.

Immunoliposomes

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide-interchange reaction. A chemotherapeutic agent (such as Doxorubicin) is optionally contained within the liposome. See Gabizon et al., J. National Cancer Inst., 81(19): 1484 (1989).

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., Fab or F(ab)$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques intracavity, or transdermally, alone or with effector cells.

The nucleic acids and proteins of the invention are useful in potential prophylactic and therapeutic applications implicated in a variety of disorders including, but not limited to: metabolic disorders, diabetes, obesity, infectious disease, anorexia, cancer, neurodegenerative disorders, Alzheimer's Disease, Parkinson's Disorder, immune disorders, hematopoictic disorders, and the various dyslipidemias, metabolic disturbances associated with obesity, the metabolic syndrome X and wasting disorders associated with chronic diseases and various cancers, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, lupus erythematosus, obesity, transplantation, adrenoleukodystrophy, congenital adrenal hyperplasia, prostate cancer, neoplasm; adenocarcinoma, lymphoma, uterus cancer, fertility, leukemia, hemophilia, hypercoagulation, idiopathic thrombocytopenic purpura, immunodeficiencies, graft versus host disease, AIDS, bronchial asthma, rheumatoid and osteoarthritis, Crohn's disease; multiple sclerosis, treatment of Albright Hereditary Ostoeodystrophy, and other diseases, disorders and conditions of the like.

Preparations for administration of the therapeutic complex of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the therapeutic complex of the invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

A therapeutically effective dose refers to that amount of the therapeutic complex sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, intravenous, intraperitoneal, parenteral or rectal administration.

Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

In an additional aspect, the present invention provides kits embodying the complex and methods of using disclosed herein. Kits of the invention optionally include one or more of the following: (1) polypeptide or nucleic acid components described herein; (2) instructions for practicing the methods described herein, and/or for operating the selection procedure herein; (3) one or more detection assay components; (4) a container for holding nucleic acids or polypeptides, other nucleic acids, transgenic plants, animals, cells, or the like and, (5) packaging materials.

Now turning to the figures, there is shown particular compositions and methods within the scope of the present invention. Such figures, and examples associated therewith, are presented in order to make certain aspects of the present invention more clearly understood and are not intended to limit the scope of the invention described herein in any manner.

EXAMPLE 1

Growth of Pre-Pro-B, Pro-B and Pre-B Cell Compartments on Different Culture Media. As illustrated in FIGS. 1A and 1B, after inoculation with freshly-harvested BM cells the pre-pro-B cell and pro-B cell compartments in the pro-B cell culture previously described by the inventors (Hayashi, et al., J. Exp. Med. 160: 1622-1639 (1984)) progressively expands with time, whereas the pre-B cell compartment progressively contracts. In contrast, under Whitlock/Witte-type culture conditions, the pre-B cell compartment progressively expands with time (FIGS. 1C and 1D) whereas the pre-pro-B cell and pro-B cell compartments progressively contract (after a brief period of expansion). Furthermore, pre-pro-B cells and pro-B cells from the lymphoid culture system generate pre-B cells when placed in Whitlock/Witte cultures or CM therefrom.

EXAMPLE 2

Recreation of Bone Marrow Microenvironment for Early Lymphopoiesis In Vitro. The nature of the interactions between BM lymphoid precursor cells and BM adherent microenvironmental cells was investigated by a combination of immunophenotyping and scanning and transmission electron microscopy of primary cultures.

The results of such studies show that two distinct microenvironmental regions are represented within the BM adherent cell layer: (a) paucilayer (PL) regions, composed of two or three horizontally oriented layers of stromal cells; and (b) multilayer (ML) regions, containing 4 to 8 layers of stromal cells. In both regions, proliferating lymphoid cells expressing the B220, and/or heat stable antigen (HSA) early B-lineage antigens, are "sandwiched" between adjacent layers of stromal cells and enveloped by cytoplasmic processes from interdigitating mouse macrophages (pseudoemperipolesis). Small clusters containing 5 to 50 lymphoid cells, preferentially develop in the PL regions are comprised primarily of TdT cells that can generate TdT.sup.+ cells upon transfer onto fresh adherent cells layers.

Under ideal conditions, individual clusters are clonally derived and the seeding efficiency of the culture system approaches 100%. Large clusters, containing up to 1,000 lymphoid cells, preferentially develop in the ML regions and are comprised primarily of TdT.sup.+ cells. The ML regions bear a close resemblance to the recently described pro-B cell-enriched, multi-cellular aggregate fraction of freshly harvested mouse BM. Hence, this system appears to structurally recreate in vitro the in vivo microenvironment for the development of pre-pro-B cells and pro-B cells.

EXAMPLE 3

Figure 2:
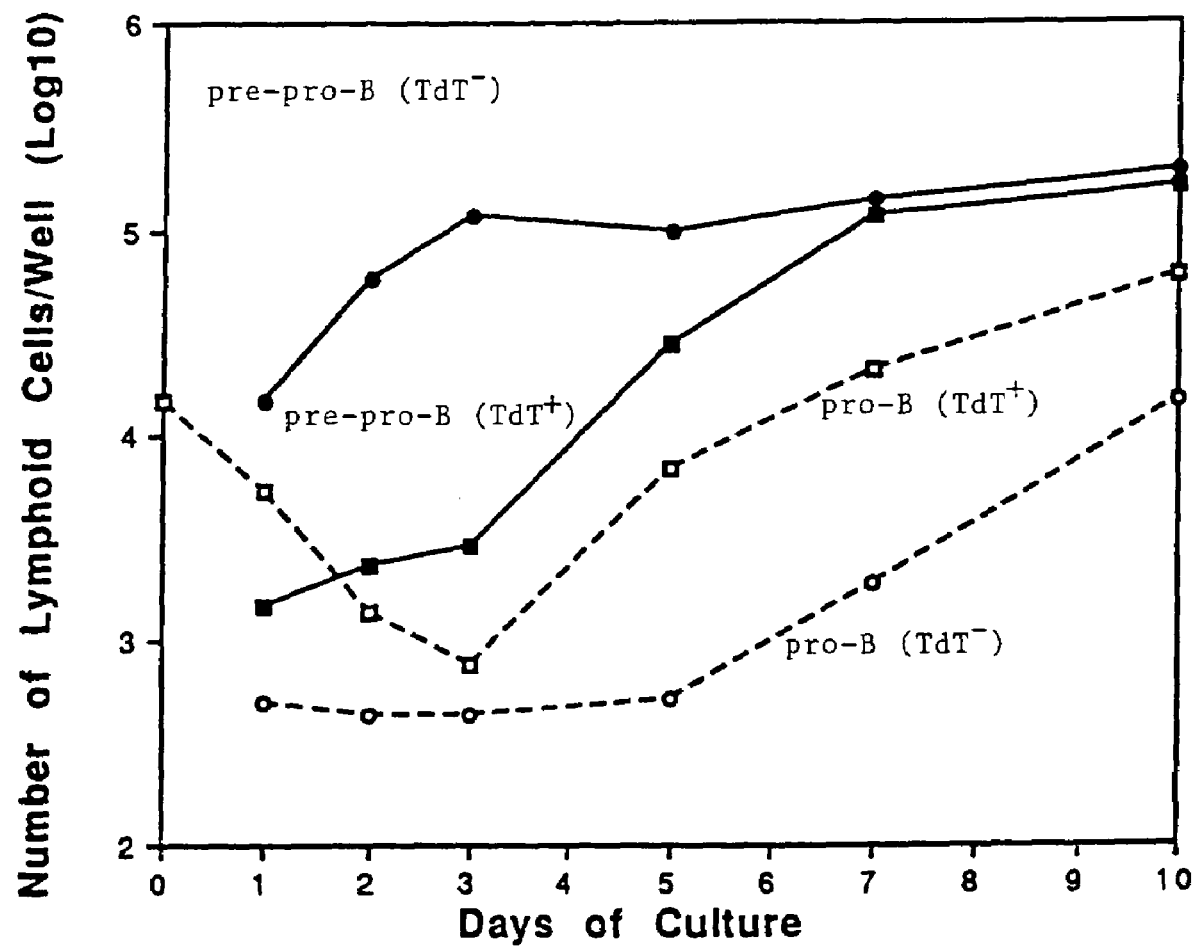
FIG. 2 is a graph of the sequential proliferation and differentiation of four subsets of B-cell progenitors, pre-pro-B (TdT$^-$), pre-pro-B (TdT$^+$), pro-B (TdT$^+$) and pro-B (TdT$^-$), cultured in the pro-B culture system as described, over ten (10) days of culture.

Properties and Developmental Relationships of the Lymphoid Cells in the Adherent and Nonadherent Compartments of the Pro-B Culture System. Turning to FIG. 2, four sequentially appearing subsets of B-cell progenitors in the inventors' pro-B culture system were characterized. The first lymphoid subset consists of adherent TdT.sup.−; (early) pre-pro-B cells that reach plateau numbers on day 3; and the second subset consists of adherent TdT+/− (late) pre-pro-B cells that plateau on day 7. This is closely followed by a parallel increase in the number of TdT+ (early) and TdT− (late) pro-B cells in the non-adherent phase.

Figure 3:
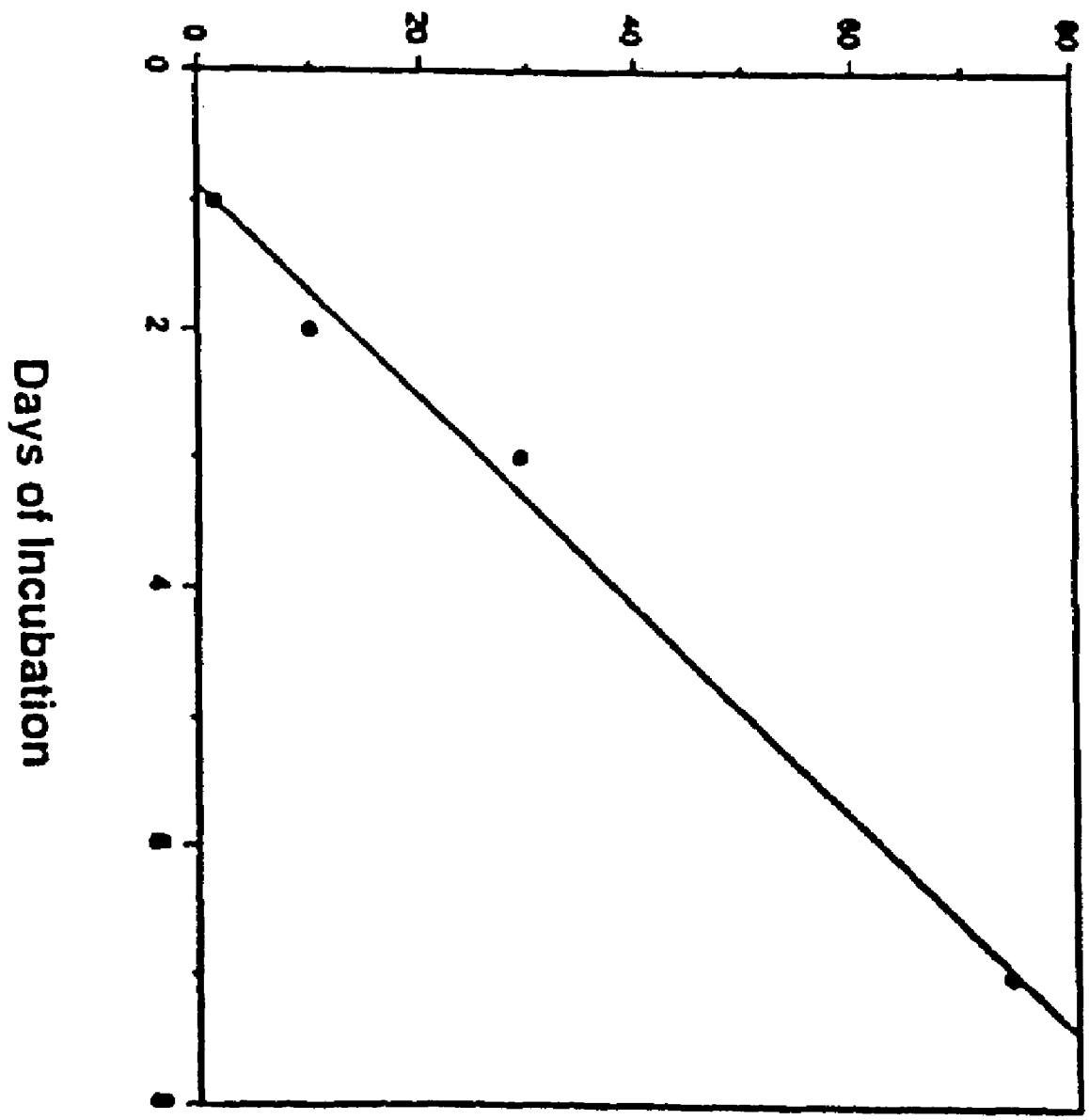
FIG. 3 is a graph illustrating the relative increase in total pre-pro-B cells freshly harvested from rat bone marrow cultured over an eight (8) day period.

In vitro transfer experiments demonstrated that virtually all of the early pre-pro-B cells in freshly harvested rat BM adhere to the mouse BM stromal cells during the first 24 hrs of culture; and by day 7 of culture, these cells had increased more than 20-fold on a per cell basis and more than 70-fold on a per well basis (FIG. 3). It was also observed that a decrease in the concentration of fetal bovine serum in the culture medium resulted in the selective release of late, but not early, pre-pro-B cells into the non-adherent compartment. These studies indicate that a stepwise progression of the earliest detectable stages in lymphoid development was associated with changes in stromal/lymphoid cell interactions partly regulated by serum-dependent adhesion mechanisms.

EXAMPLE 4

Figure 4:
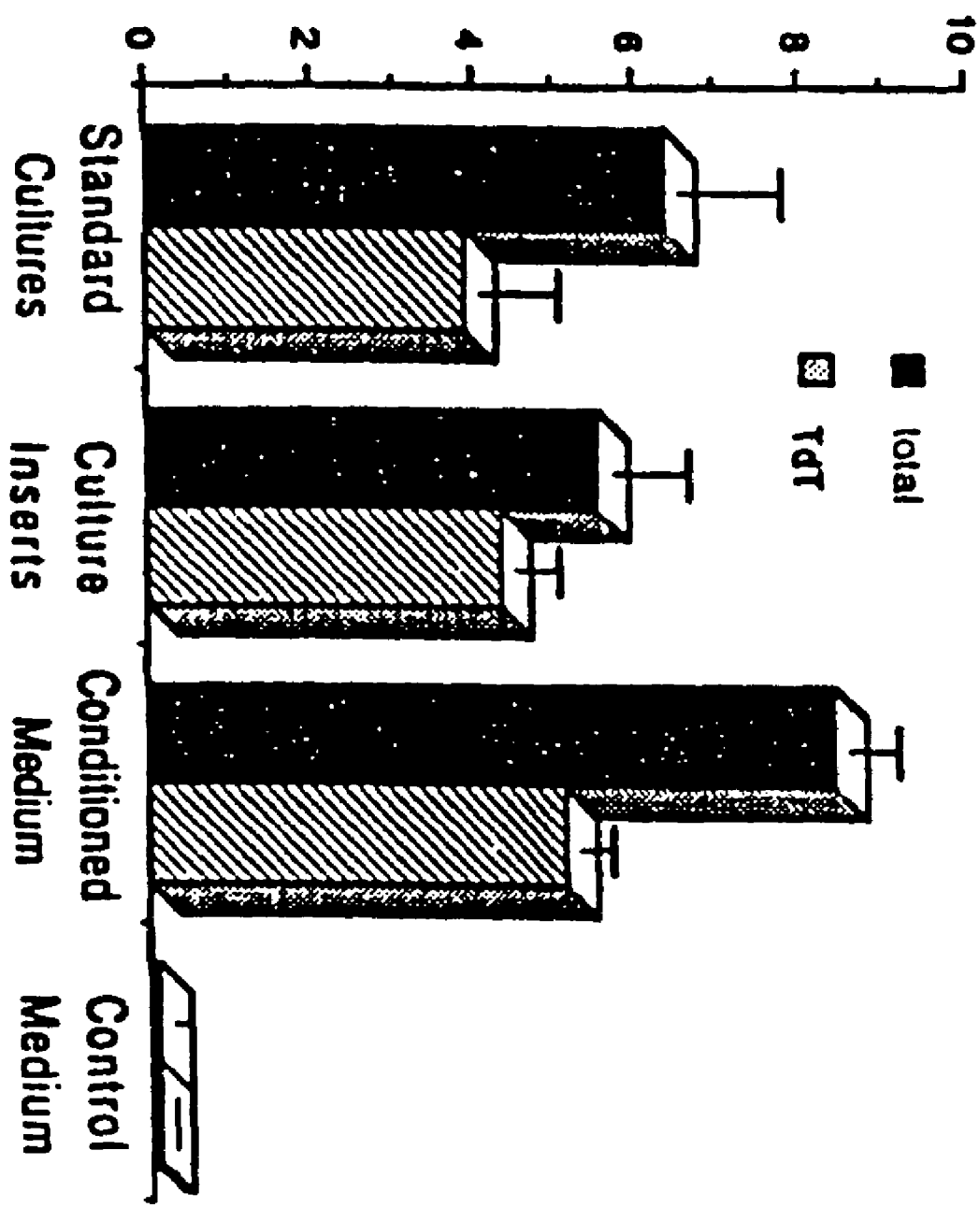
FIG. 4 is a bar graph of growth of rat bone marrow lymphoid cells in different media, total as well as those displaying the TdT marker.

Ability of Medium Conditioned by BM Stromal Cells to Selectively Support the Development of Pre-Pro-B Cells and Pro-B Cells in Vitro. Although the pro-B culture system is characterized by physical interaction-between developing lymphocytes, BM stromal cells and macrophages, experiments using microporous membrane culture inserts demonstrate that these cognitive recognition events, albeit more efficient, are not essential (FIG. 4). Similarly, medium conditioned (CM) with mouse BM adherent cells supported the proliferation of lymphoid precursor cells in a dose-dependent manner. Upon ultrafiltration, all of the lymphostimulatory activity in the CM was recovered in the 50-100 kD apparent MW fraction; and double immunofluorescence for incorporated bromodeoxyuridine (BrdU) and early B-lineage markers indicated that the lymphoproliferative response selectively involved early (TdT−) and late (TdT+) pre-pro-B cells, but not pro-B cells.

EXAMPLE 5

Figures 5A, 5B:
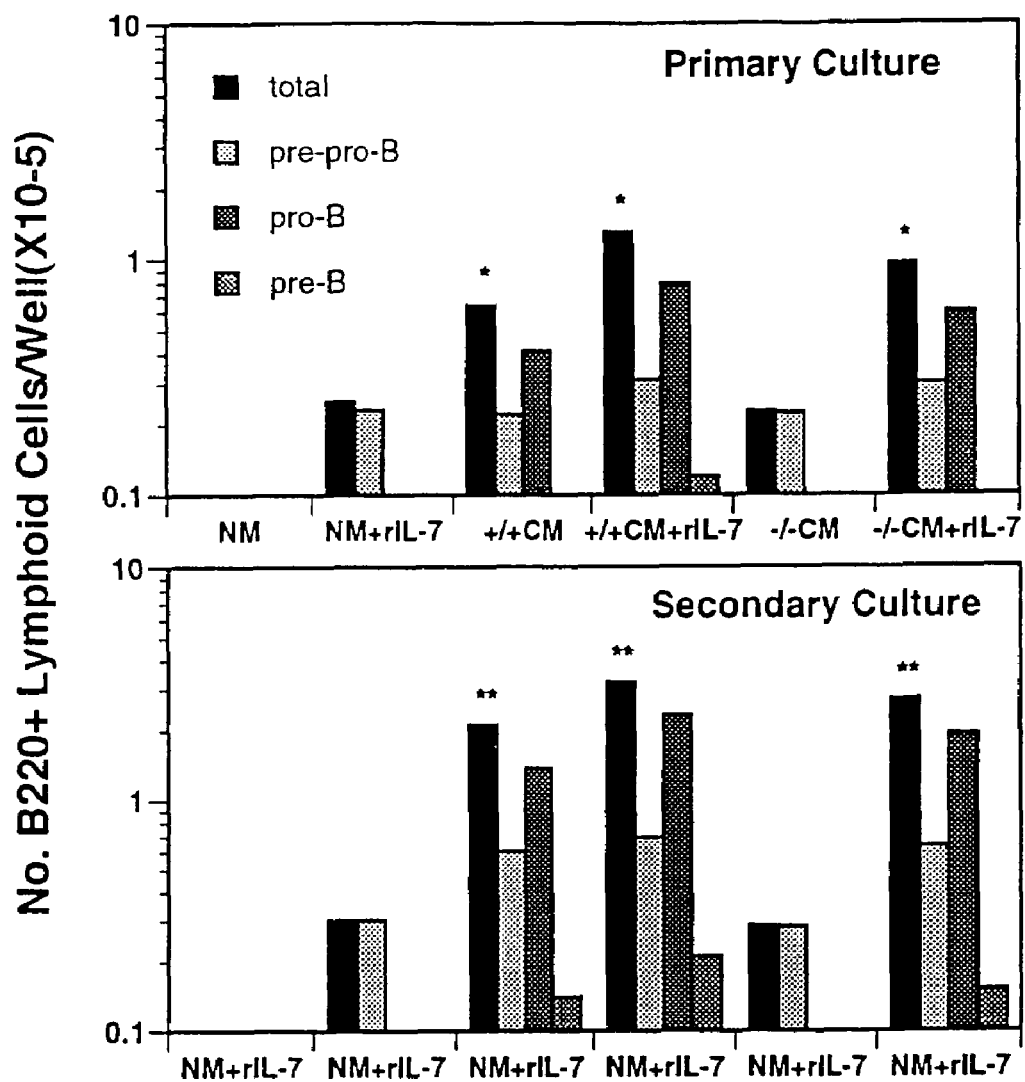
FIGS. 5A and 5B are bar graphs of the number of cells (total, pre-pro-B, pro-B, and pre-B) found in primary culture (FIG. 5A) and secondary culture (FIG. 5B) given different combinations of normal medium (NM), bone marrow stromal conditioned medium (CM), and/or rIL-7.
Figure 6:
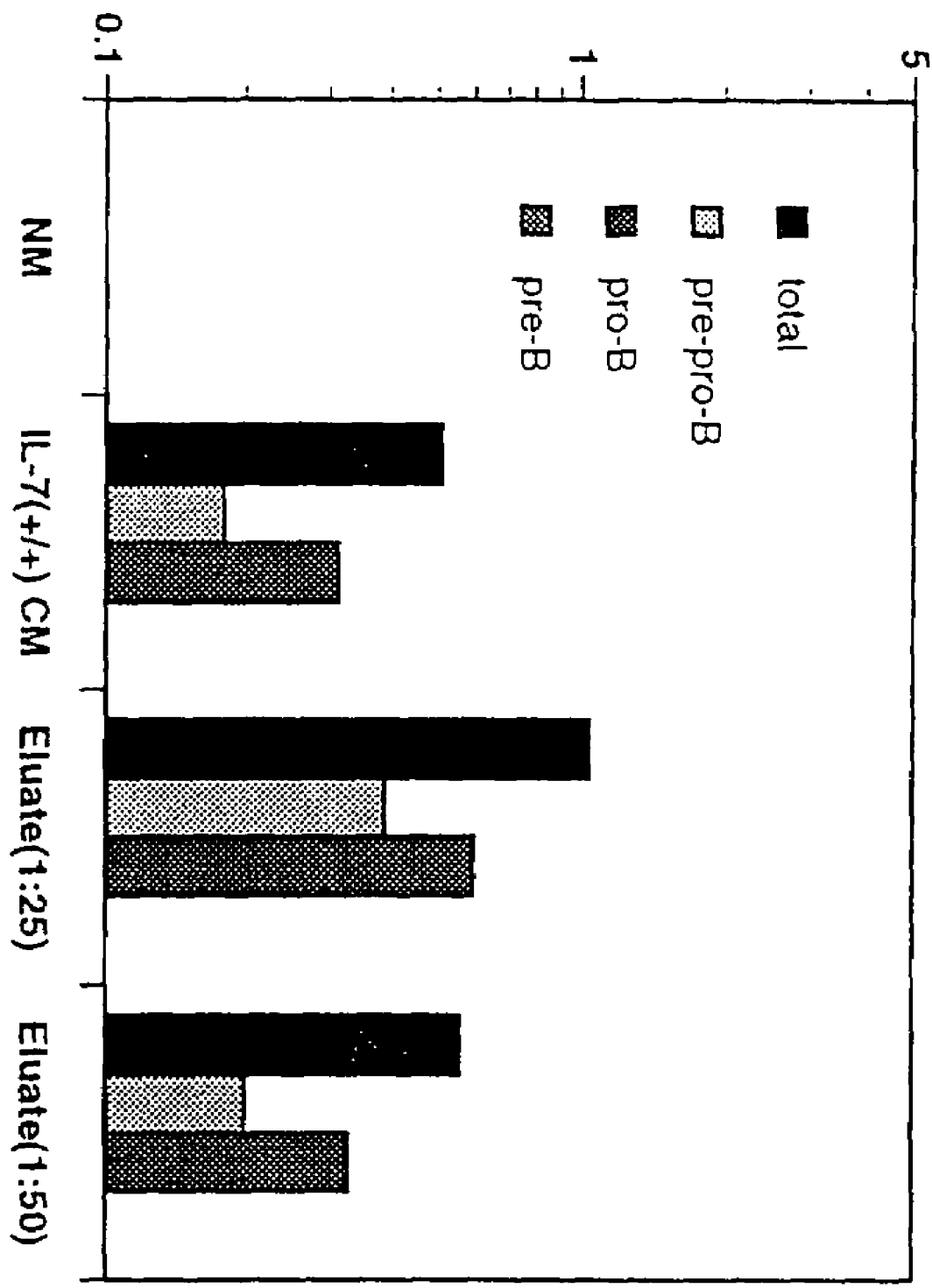
FIG. 6 is a bar graph of the number of cells (total, pre-pro-B, pro-B, and pre-B) found in a IL-7 (+/+) conditioned medium (CM) versus eluate.

The Pre-pro-B Cell Growth-Stimulating Factor (PPBSF), Detection of IL-7 (SEQ ID NO:7, 8) and a Non-IL-7 Component of PPBSF. Inasmuch as IL-7 (SEQ ID NO:7, 8) is one of the cytokines most closely associated with early B-lineage development, BM adherent cells and stromal cell lines from wild-type and IL-7 gene-deleted (−/−) mice were utilized to investigate its possible regulatory role in the pro-B culture system. The results show that both rIL-7 and IL-7 (−/−) CM maintain the viability of pre-pro-B cells from freshly harvested rat BM, but that neither induces them to proliferate and/or differentiate, even in the presence of IL-3, rSCF and/or rIGF. However, as seen in FIG. 5A (primary culture) when added to IL-7 (−/−) CM, rIL-7 efficiently stimulates proliferation and differentiation of freshly harvested pre-pro-B cells. Conversely, anti-IL-7 mAb inhibits the expansion of pre-pro-B cells in culture, and adsorbs the pre-pro-B cell growth-stimulating activity from both IL-7 (+/+) CM and rIL-7-supplemented IL-7 (−/−) CM. Yet, anti-IL-7 mAb does not neutralize the pre-pro-B cell growth-stimulating activity of these CM; and rIL-7 does not restore this activity to anti-IL-7 mAb-adsorbed CM. These results suggest that the pre-pro-B cell growth-stimulating activity in the pro-B culture system is the property of a self-aggregating molecular complex of IL-7 and a second BM stromal cell-derived co-factor (See FIG. 6). The results also suggest that this pre-pro-B cell growth-stimulating factor (PPBSF) not only selectively stimulates proliferation of pre-pro-B cells, but "primes" them and/or their immediate descendants to respond directly to monomeric IL-7 (FIG. 5B, secondary culture).

Figure 7:
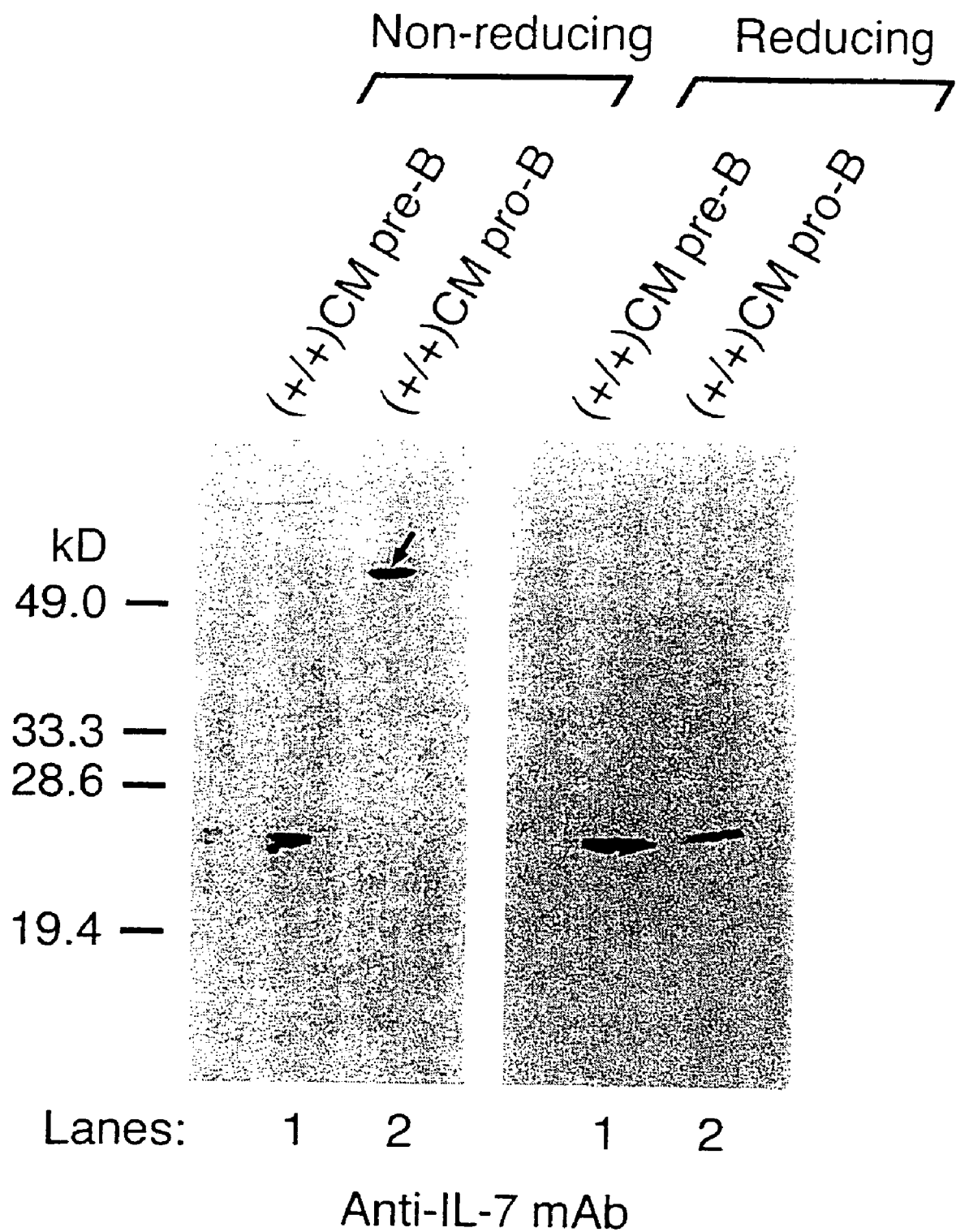
FIG. 7 is a western immunoblot of PPBSF developed with anti-IL-7 monoclonal antibody in pre-B and pro-B cell conditioned medium under reducing and non-reducing conditions.
Figure 8:
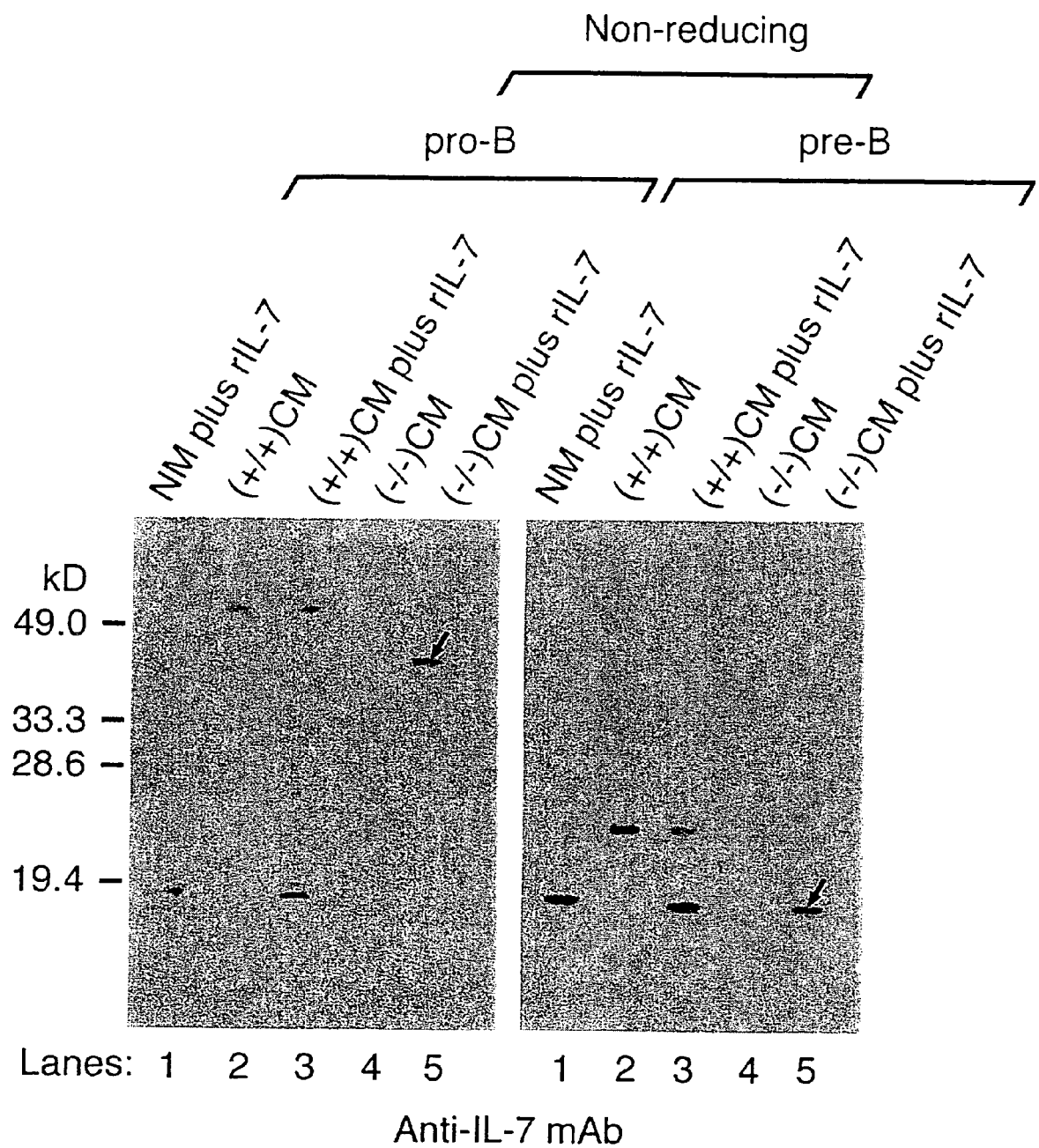
FIG. 8 is a western immunoblot of PPBSF developed with anti-IL-7 monoclonal antibody in designated cell medium with and without rIL-7 (SEQ ID NO:7, 8).
Figure 9:
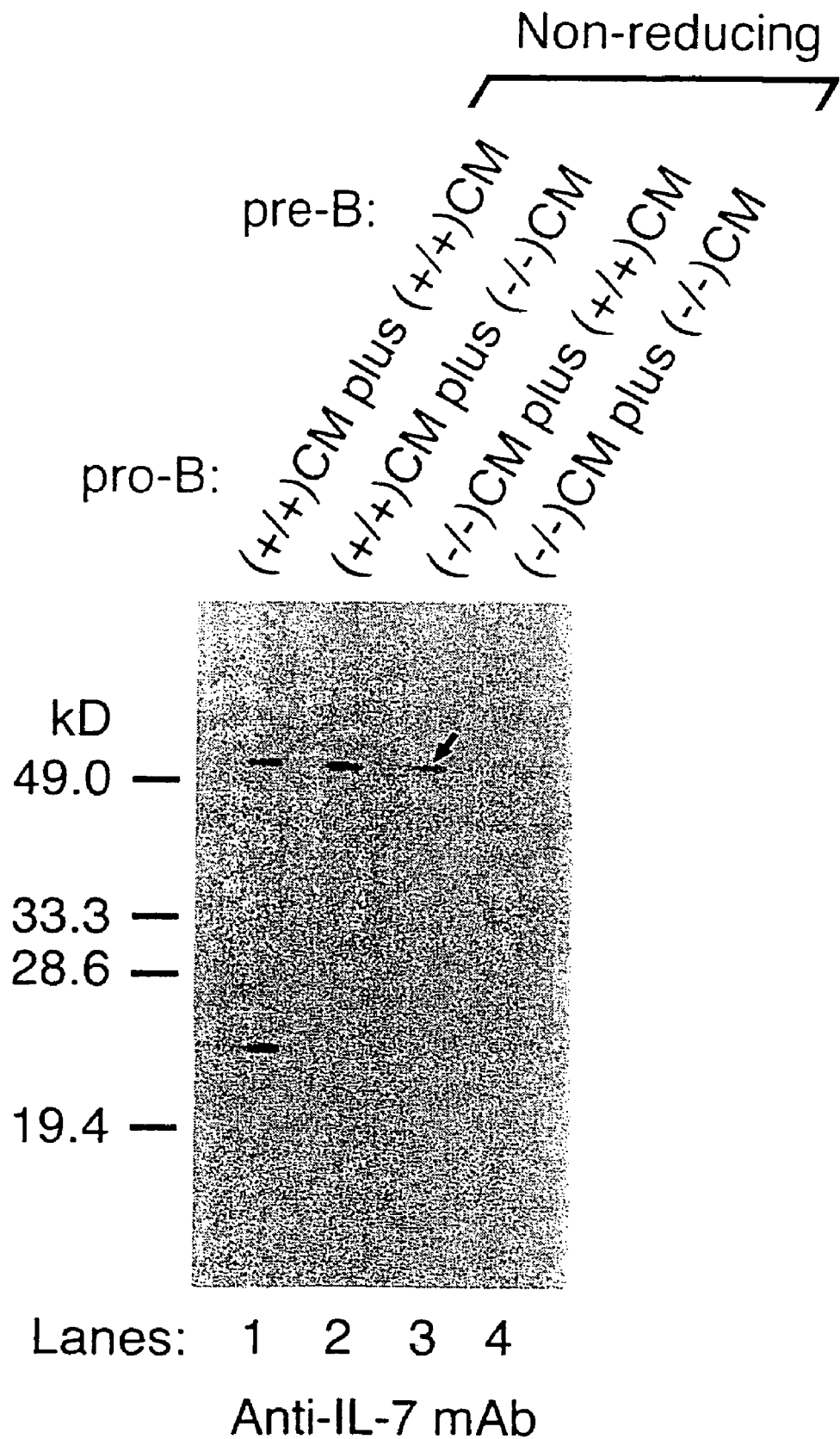
FIG. 9 is a western immunoblot of PPBSF developed with anti-IL-7 monoclonal antibody in designated combinations of conditioned medium.

PPBSF is a Covalently-linked Heterodimer of IL-7 (SEQ ID NO:7, 8) and an $M_r$ 30,000 Dalton Co-factor. Direct evidence for the existence of PPBSF in CM generated under pro-B cell, but not pre-B cell, culture conditions is provided by Western immunoblot analysis (FIG. 7). The results demonstrate that, when developed with anti-IL-7 mAb, PPBSF migrates electrophoretically as an apparent 55 kD molecule under non-reducing conditions, whereas the IL-7 (SEQ ID NO:7, 8) component migrates as an apparent 25 kD molecule under reducing conditions. Furthermore, IL-7 exists almost entirely as an heterodimer (i.e. PPBSF) in pro-B-type cultures, and as a monomer in pre-B-type cultures. However, addition of rIL-7 or native IL-7 (from pre-B CM) to CM from IL-7 KO mice results in the rapid formation of apparent 45 kD (FIG. 8, lane 5) and 55 kD (FIG. 9, lane 3) molecular complexes, respectively, both of which have the functional properties of PPBSF.

Figure 10:
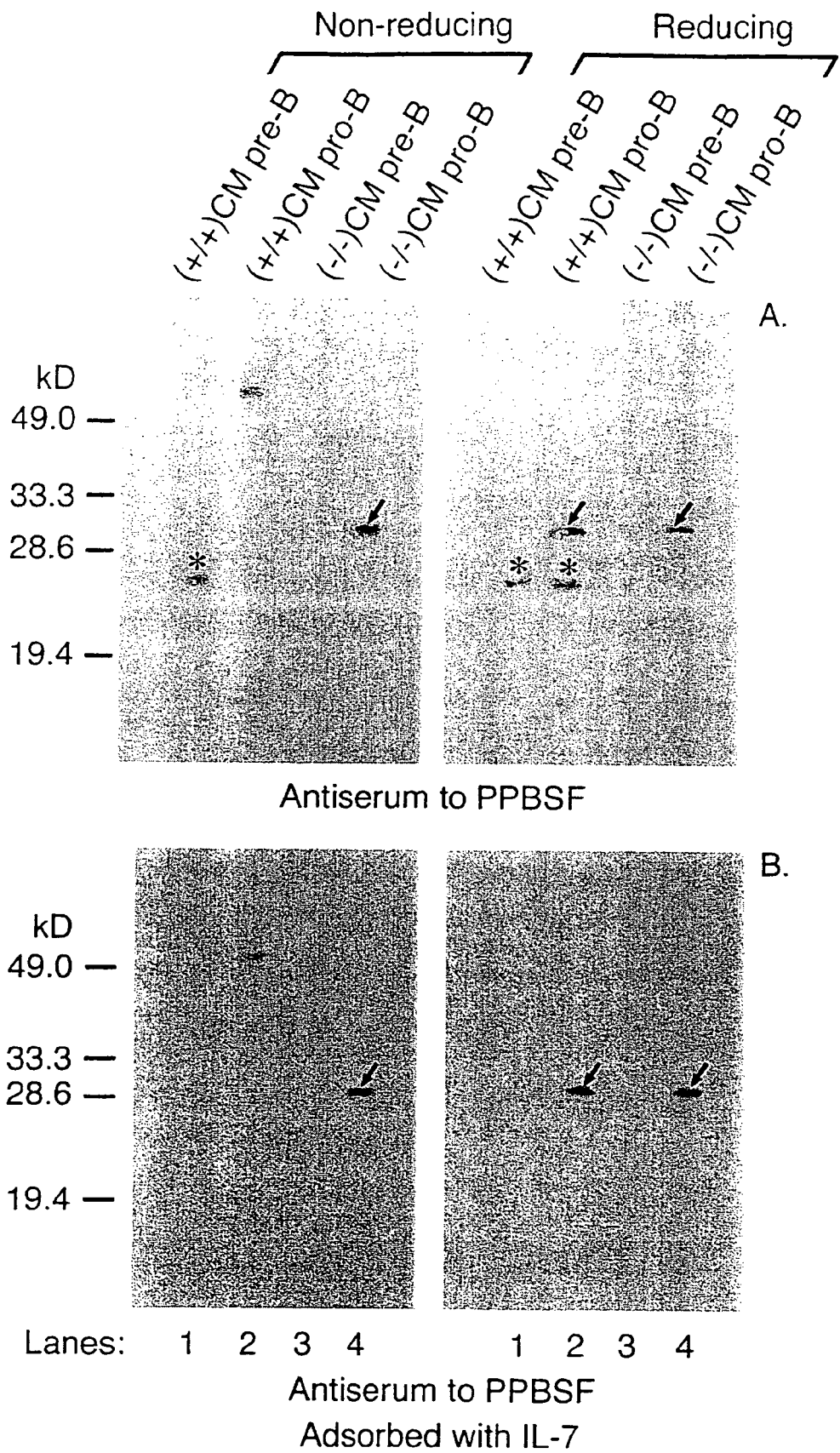
FIG. 10 is a western immunoblot of PPBSF developed with antiserum to PPBSF and adsorbed with IL-7 (SEQ ID NO:7, 8) for designated conditioned medium, under reducing and non-reducing conditions.
Figure 11:
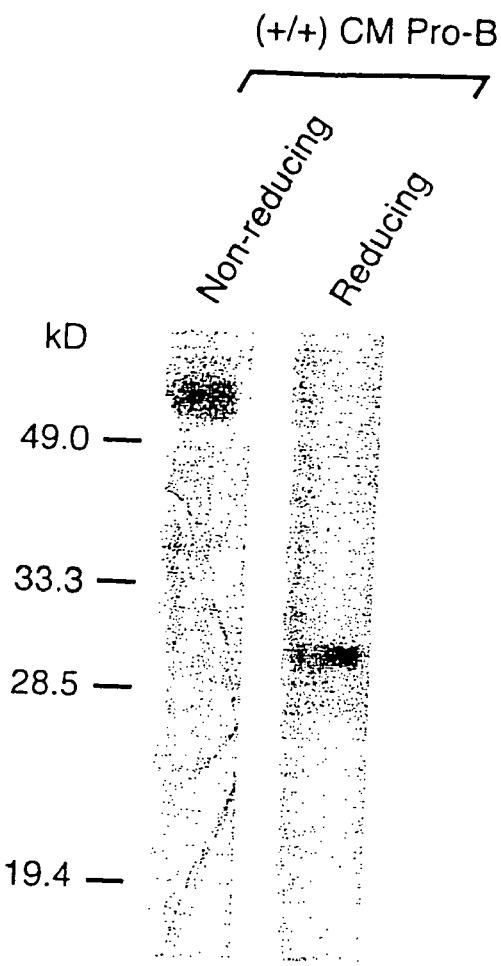
FIG. 11 is a western immunoblot electrophoresed under reducing and non-reducing conditions demonstrating a 30 kD molecule as the non-IL-7 component of PPBSF in (+/+) CM Pro-B.
Figure 12:
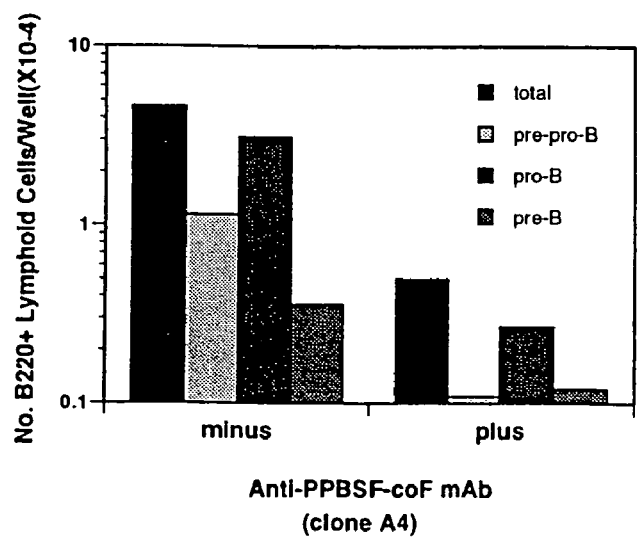
FIG. 12 is a bar graph of the number of B220+ lymphoid cells (total, pre-pro-B, pre-B, pro-B) plus and minus anti-PPBSF-coF monoclonal antibody.

Using a neutralizing antiserum prepared in IL-7 (−/−) mice against IL-7 (+/+) CM (and subsequently monoclonal antibody (IgG2a; clone A4) against affinity-purified PPBSF), the non-IL-7 component of PPBSF was identified by Western analysis as an apparent 30 kD molecule (FIG. 10, lanes 2 and 4; and FIG. 11). These Abs react with PPBSF-coF in both its heterodimeric and monomeric forms, and neutralize the PPBSF activity in CM (FIG. 12). PPBSF-coF is able to maintain the viability of pre-pro-B cells, but does not stimulate their proliferation unless complexed with IL-7 (SEQ ID NO:7, 8). It is constitutively produced by lines of IL-7 (−/−) BM stromal cells under pro-B, but not pre-B-type culture conditions. It does not appear to be SCF, IGF-1, TSLP, Fet3, SDF-I or the soluble form of the IL-7R.

EXAMPLE 6

Determination that PPBSF is a Hybrid Cytokine of IL-7 (SEQ ID NO:7, 8) and the beta-chain of Hepatocyte Growth Factor/scatter Factor (HGF/SF) (SEQ ID NO:3, 4, 13, and 14); Identity of PPBSF-coF. To identify the PPBSF-coF, affinity purified native PPBSF was electrophoresed under reducing conditions and the 30 kDa band was subjected to amino acid analysis. The results demonstrated that the first 15 of 17 amino acid residues were identical to the published sequence of mouse HGF-beta chain (SEQ ID NO:3, 4) (FIG. 13), as was the overall molecular mass of the peptide. The identity of PPBSF-coF as the HFG-beta chain was confirmed by reciprocal Western blot analyses, in which antibodies to HGF-beta-chain reacted with purified native PPBSF-coF, and mAbs to PPBSF-coF reacted with rHGF. In addition, both anti-HGF and anti-HGF-beta antibodies neutralized the PPBSF activity in IL-7 (+/+) CM.

Figure 16:
FIG. 16 is gel electrophoresis illustrating RT-PCT analysis of the HGF mRNA (SEQ ID NO:11) transcripts from mouse BM stromal cells. First-stand cDNA from cultured IL-7 (−/−) mouse BM stromal cells subjected to PCR with primers designed to amplify the entire coding sequence of mouse HGF. The blot demonstrates both the 2230 bp product corresponding to the full-length HGF and a novel 840-bp product, corresponding to HGF-beta chain.

Identification and Cloning of a Variant of HGF mRNA. Total RNA was isolated with TRI$_{zoltm}$ Reagent (Total RNA Isolation Reagent, Life Technologies, Gaithersburg, Md.) from IL-7 (−/−) BM stromal cells. Random-primed first-strand cDNA was generated from this RNA using MMLV reverse transcriptase (RETRO Script™, Amibion, Austin, Tex.). PCR reactions were performed with the cDNA, Taq polymerase (Life Technologies, Gaithersburg, Md.), and primers designed to amplify the entire coding sequence of mouse HGF: 5'-CAGTCTGCTCGAACTGCA-3' (SEQ ID NO:1) (in 5' flanking region) 5'-TGGCCTCTTCTATG-GCTA-3' (SEQ ID NO:2) (in 3' flanking region). Two RT-PCR products were obtained when the amplified fragments were separated on 1% agarose gel and visualized by ethidium bromide (FIG. 16). One of these products corresponded to the full-length HGF cDNA (2230 bp). However, the second product was 840 bp long, the same as the coding sequence of HGF-beta. The cDNA of the shorter PT-PCR product was cloned, and the nucleotide sequence was found to concur precisely with the published mouse HGF-beta cDNA sequence (See SEQ ID NO:11). Furthermore, although the HGF-alpha chain cDNA was completely absent, the signal sequence was identical to that in full-length HGF cDNA.

EXAMPLE 7

Figure 14:
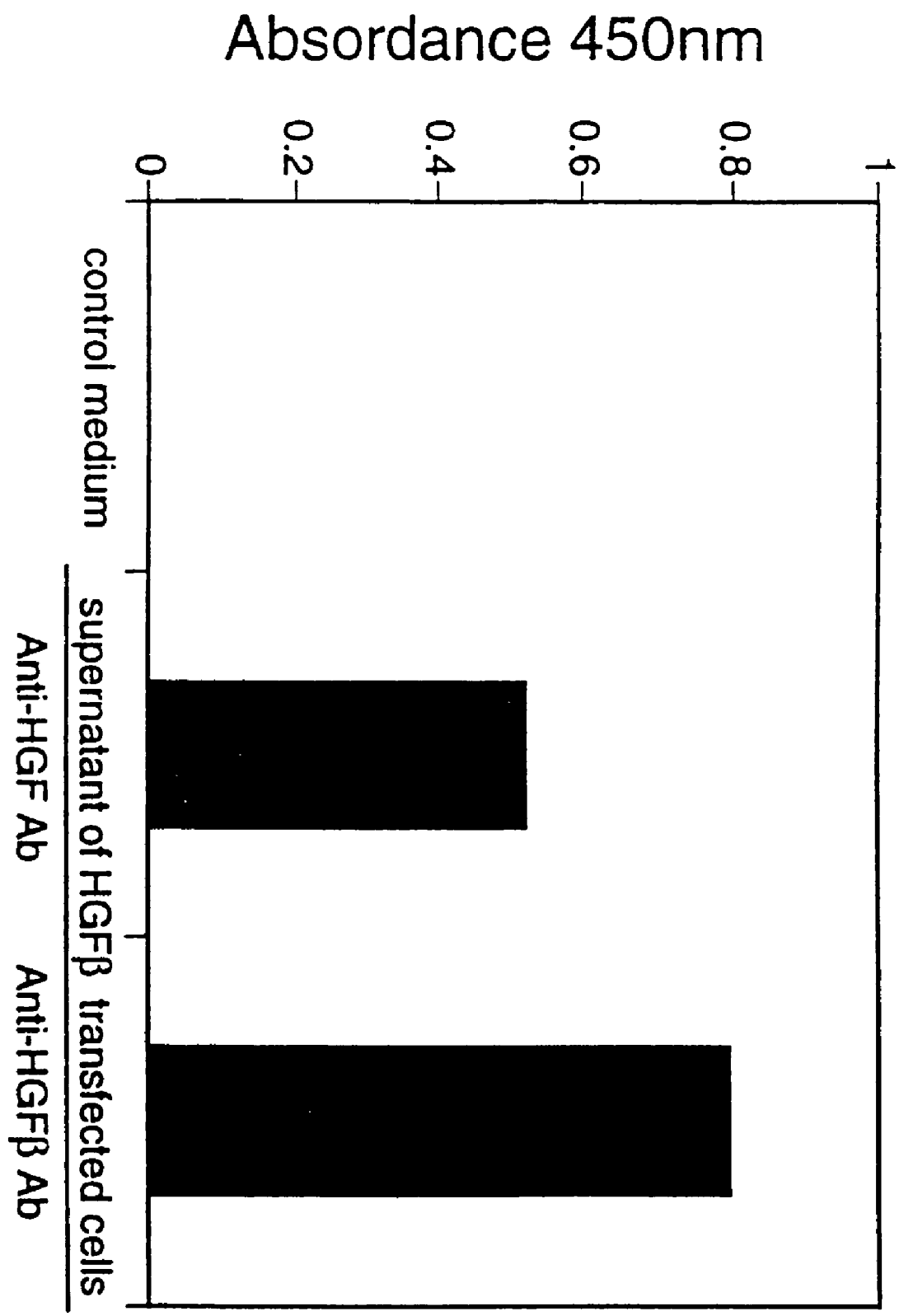
FIG. 14 is a bar graph of HGF-beta (SEQ ID NO:3, 4) expression in CHO cells transfected with a mammalian expression vector into which the HGF-beta was cloned versus control medium.

Formation and Biological Activity of Heterodimes of rIL-7 (SEQ ID NO:7, 8) and rHGF-beta (SEQ ID NO:3, 4, 13, and 14), Production of Recombinant HGF-beta Proteins. The PCR-amplified splice variant was subcloned into the mammalian expression vector pcDNA3.1 (+) (Invitrogen). The plasmid was transfected into Chinese hamster ovary (CHO) cells (LIPOFECTAMINE Plus™ Reagent, Life Technologies). The serum-free supernatant from the transfected CHO cells was collected, concentrated 10 times and filtered to remove any cells and evaluated for the production of HGF-beta protein (SEQ ID NO:3, 4, 13, and 14) by ELISA using anti-HGF-beta antibodies. The supernatant of transfected cells with vector but without HGF-beta gene was used as control medium. HGF-beta protein was detected in the supernatant of HGF-beta-transfected cells, but not in that of the empty vector-transfected cells (FIG. 14). The HGF-beta gene (See SEQ ID NO:9) was also subcloned into prokaryotic fusion protein expression vector pCAL-n (Stratagene, La Jolla, Calif.) and transformed into *E. coli* BL21(DE3). The fusion protein was purified by calmodulin affinity, and rHGF-beta, released by thrombin, was detected as a single band by SDS-PAGE and Western blotting.

EXAMPLE 8

Figure 17:
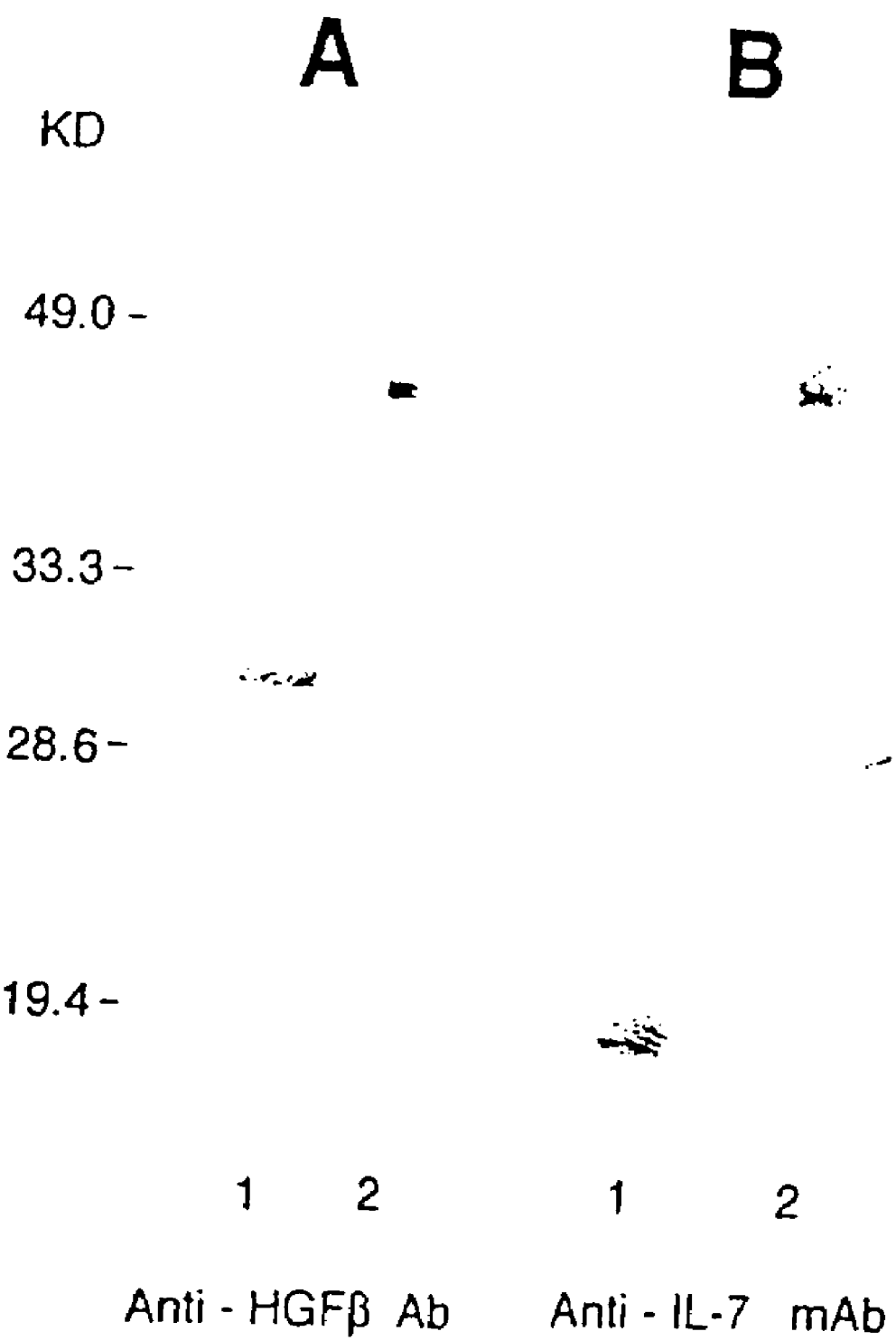
FIG. 17 is a western blot illustrating that recombinant IL-7 (SEQ ID NO:8) forms a heterodimer with rHGF-beta (SEQ ID NO:3, 4) in the presence of low molecular weight heparan-sulfate derived oligosaccharides. Equimolar concentrations of rIL-7 and rHGF-beta were mixed in the presence and absence of low molecular weight heparan sulfate-derived oligosaccharides. One hour later the mixtures were electrophoresed and developed with (A) anti-HFG-beta Ab or (B) anti-IL-7 mAb. In each instance as shown, a 45 kD heterodimer was observed in the presence (lane 2), but not the absence (lane 1) of, heparan sulfate.

Formation of a Biological Activive of Heterodimer of rIL-7 (SEQ ID NO:7, 8) and rHGF-beta (SEQ ID NO:3, 4, 13, and 14) Using Low Molecular Weight Heparin Sulfate Oligosaccharides. As both IL-7 (SEQ ID NO:7, 8) and HGF (SEQ ID NO:5, 6) are heparin-binding molecules, the present inventors tested the ability of rIL-7 and rHGF-beta (SEQ ID NO:3, 4, 13, and 14) to from a heterodimer when equimolar ratios were mixed in serum-free medium in the presence or absence of low molecular weight heparin sulfate (HS)-derived oligosaccharides. The reactants were electrophoresed under nonreducing conditions and subjected to Western blot analysis. The results in FIG. 17 show that rHGF-beta migrated at 30 kD when added to rIL-7 in the absence of the HS-derived oligosaccharides, and at 45 kD in their presence. Similarly, rIL-7 migrated at 14.5 kD when added to rHGF-beta in absence of HS-derived oligosaccharides, and at 45 kD in their presence. Hence, rIL-7 and HGF-beta form an heterodimer in the presence of low molecular weight HS-derived oligosaccharides. Comparable results were obtained when FBS, rather than HS-derived oligosaccharides, was added to the medium.

Figure 15:
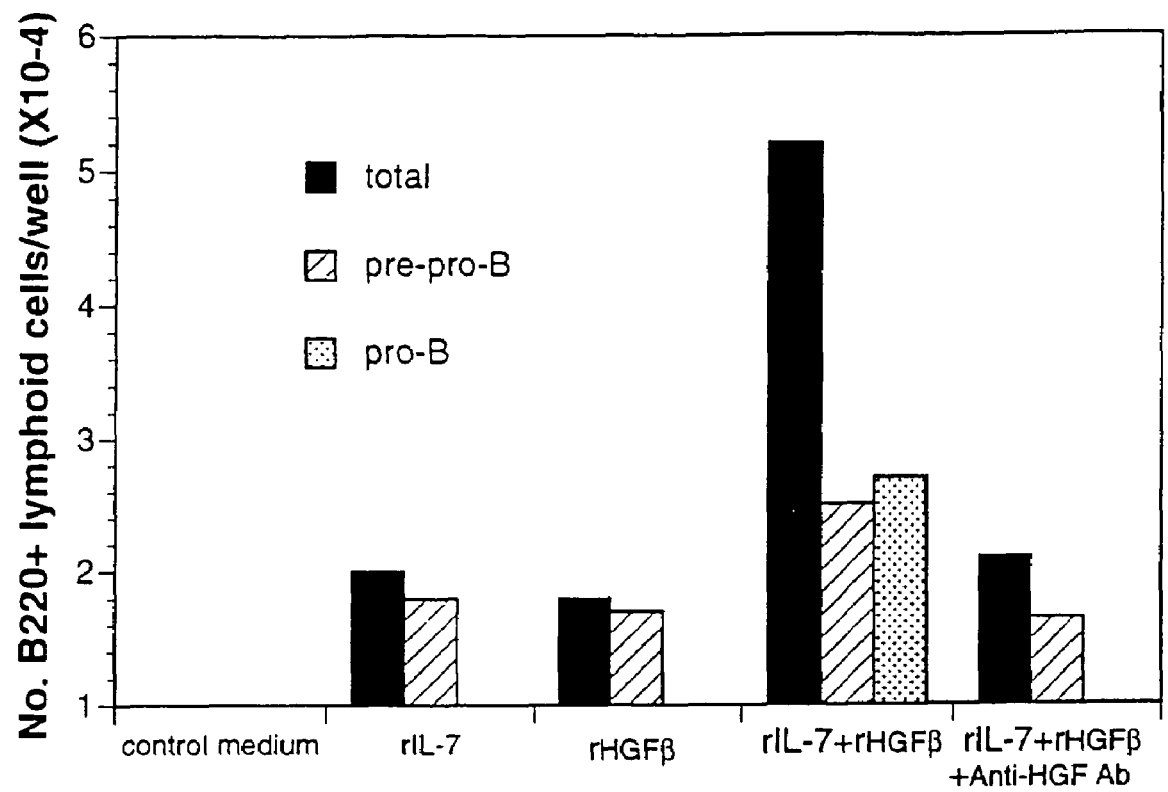
FIG. 15 is a bar graph of pre-pro-B cell growth stimulating activity of the combination of rIL-7 (SEQ ID NO: 8) and rHGF-beta (SEQ ID NO:3, 4).

To determine if the IL-7/HGF-beta heterodimer had biological activity, freshly harvested rat BM cells were incubated in culture medium containing 20% FBS plus rIL-7 and/or 2 times supernatant of HGF-beta transfected cells in the absence of anti-HGF-beta Ab. Lymphoid cells were harvested and phenotyped on day 10. Both rIL-7 and the supernatant of HGF-beta-gene transfected cells (or purified rHGF.beta. therefrom) were able to maintain the viability of pre-pro-B cells, but neither was able to stimulate their proliferation or to induce their differentiation to pro-B cells. However, when added concurrently, these reagents stimulated a significant increase in the generation of both pre-pro-B cells and pro-B cells (FIG. 15). Furthermore, this activity could be neutralized by anti-HGF-beta antibody. Similar results were obtained when the purified heterodimer of rIL-7 and rHGF-beta performed in the presence of HS-derived oligosaccharides, was used.

EXAMPLE 9

Figure 18:
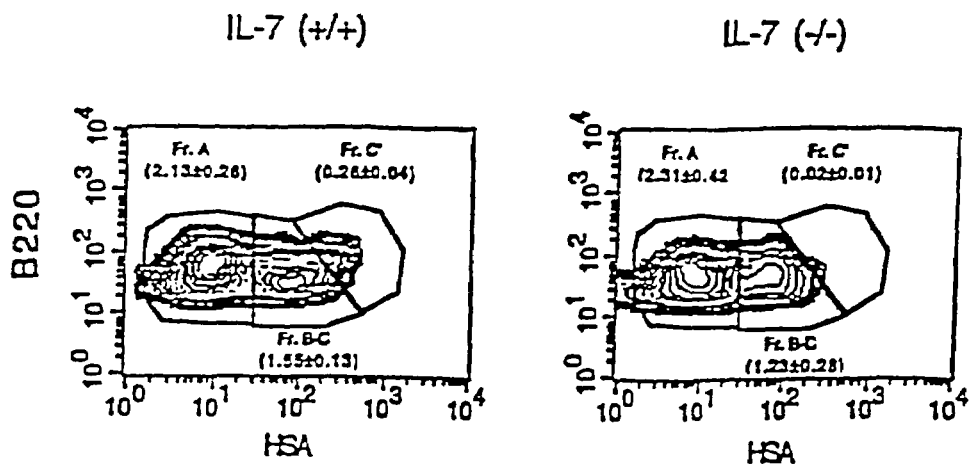
FIGS. 18-21 are flow cytometry histograms of B-cell populations (pre-pro-B, (Fr.A), pro-B (Fr.B-C), and pre-B (Fr.C')) (FIG. 18) in IL-7 knock-out (K/O) mice with population fractions demonstrating expression of IL-7R-alpha (FIG. 19), TdT (FIG. 20), and Cµ (FIG. 21).
Figure 19:
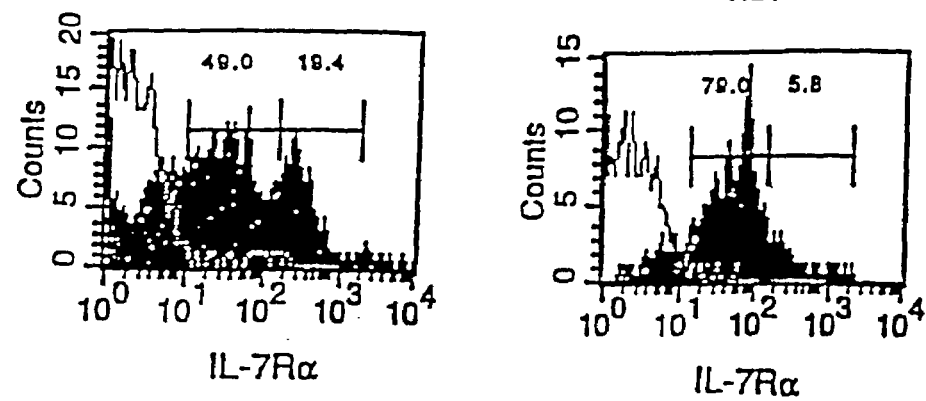
Figure 20:
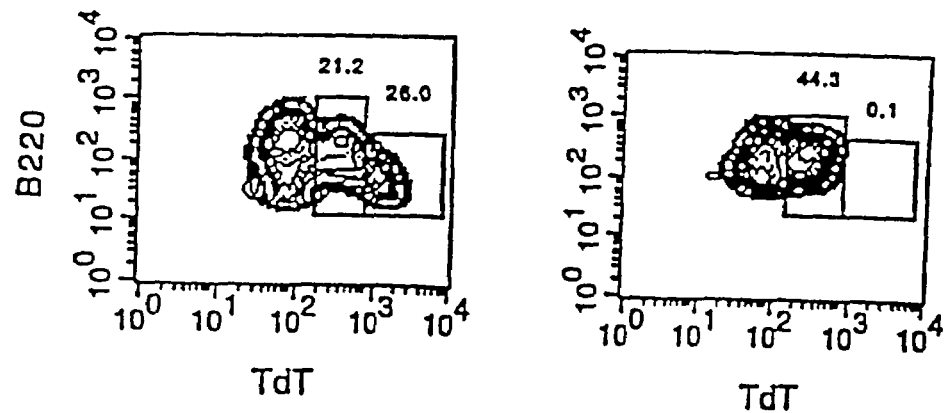
Figure 21:
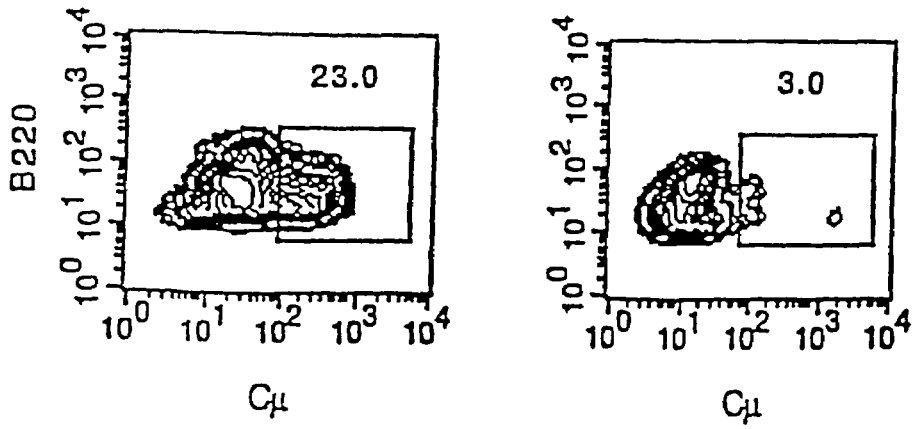

Analysis of B-Cell Development in Interleukin (IL)-7 Gene-deleted Mice, Maturation Arrest Occurs at the Late pro-B Cell Stage. Bone marrow cells from IL-7 K/O mice were stained for the expression of B220, CD43, HSA and/or BP-1, as analyzed by FCM according to the scheme of Hardy et al., J. Exp. Med. 173: 1213-1225 (1991). The data in FIG. 18 indicate that: (a) the number of Fr A (pre-pro-B) cells is normal; (b) Fr B and C (pro-B) cells are slightly reduced; and (c) Fr C', which is the transitional stage from pro-B to pre-B cells is missing. Furthermore, the expression of CD25, which has been suggested to distinguish cells undergoing VDJ from those undergoing DJ gene rearrangement was severely reduced. In addition, up-regulation of IL-7R-alpha and TdT, normally observed during pre-pro-B to pro-B cell differentiation, did not occur (FIGS. 19 and 20); neither did cμ expression of the late pro-B cell (transitional) stage (FIG. 21). Hence, although IL-7 (SEQ ID NO:7, 8) is not essential for the development of pro-B cells in BM, it is necessary for several key aspects of their differentiation.

Similar Defects Occur in γc K/O and Jak3 K/O Mice. Like their counterparts in IL-7 K/O mice, pro-B cells from gamma-c K/O and Jak3 K/O mice arrest at Fr C'and express abnormally low levels of TdT, IL-7R-alpha and cμ. Conversely, despite also arresting at Fr C', pro-B cells from lambda5 K/O mice and RAG-1 K/O mice upregulate TdT and IL-7R-alpha, and the former express normal levels of cμ. Taken together, these results suggest that signaling through the IL-7R-alpha/gamma-c/Jak3 complex is essential for upregulation of TdT and IL-7R-alpha, for expression of cμ, and for the efficient development of cells beyond the pro-B cell stage.

EXAMPLE 10

Effect of PPBSF and rIL-7 in IL-7 K/O Mice. Because rIL-7 (SEQ ID NO:7, 8) supported the proliferation and differentiation of pro-B cells from IL-7 K/O mice in the presence of IL-7 (−/−) BM stromal cells, and IL-7-depleted CM from IL-7+/+ stromal cells was not functionally reconstituted by rIL-7, it was suspected that PPBSF, the heterodimeric form of IL-7, was the responsible factor in the pro-B culture system. This was confirmed by demonstrating that pretreatment with purified PPBSF enabled pro-B cells from IL-7 K/O mice to respond to rIL-7. The in vivo administration of rIL-7 to IL-7 K/O mice may correct the abnormalities in pro-B cell development by forming PPBSF in BM with the stromal cell derived PPBSF cofactor. It may be postulated that the in vivo administration of anti-IL-7 mAb prevents the production or survival of pro-B cells in IL-7 competent mice by simultaneously eliminating monomeric IL-7 and PPBSF. However, some level of redundancy by other cytokines, such as IL-3 and TSLP, may partially compensate for the role of PPBSF. The fact that both components of the PPBSF heterodimer are avidly bound by heparin sulfate oligosaccharides, as disclosed, may suggest that PPBSF may function as a cell surface and/or ECM-bound molecular complex.

A more specific answer to the above question appears to reside in the ability of PPBSF to selectively regulate the proliferation and differentiation of pre-pro-B cells, which normally express low levels of the IL-7R-alpha; and of monomeric IL-7 to regulate the G1/S transition and differentiation of pro-B cells, which normally express high levels of the IL-7R-alpha. As PPBSF does not stimulate proliferation of pro-B cells and IL-7 does not stimulate proliferation of pre-pro-B cells, it would appear that PPBSF induces pre-pro-B cells to become IL-7-responsive pro-B cells by up-regulating the expression of IL-7R-alpha.

PPBSF, but not rIL-7 (SEQ ID NO:7, 8), Upregulates TdT and IL-7R-alpha on pro-B Cells From IL-K/O Mice In Vitro. rIL-7 (SEQ ID NO:7, 8) stimulated marked in vitro proliferation of pro-B cells from IL-7 (+/+) and RAG-1 (−/−) mice, but not from IL-7 (−/−) mice. Conversely, native PPBSF (but not rIL-7 or PPBSF-coF alone) not only upregulated the expression of IL-7R-alpha, TdT, and cμ in pro-B cells from IL-7 (−/−) mice, but "primed" them to proliferate in response to rIL-7. These results strongly support our working hypothesis that, in addition to stimulating the proliferation and differentiation of pre-pro-B cells, PPBSF up-regulates the expression of high affinity IL-7R, thereby enabling pro-B cells to respond to monomeric IL-7. Significantly, PPBSF also "primed" pro-B cells from IL-7 K/O mice to proliferate to rIL-3 in the absence of IL-7.

Figures 22A, 22B, 22C:
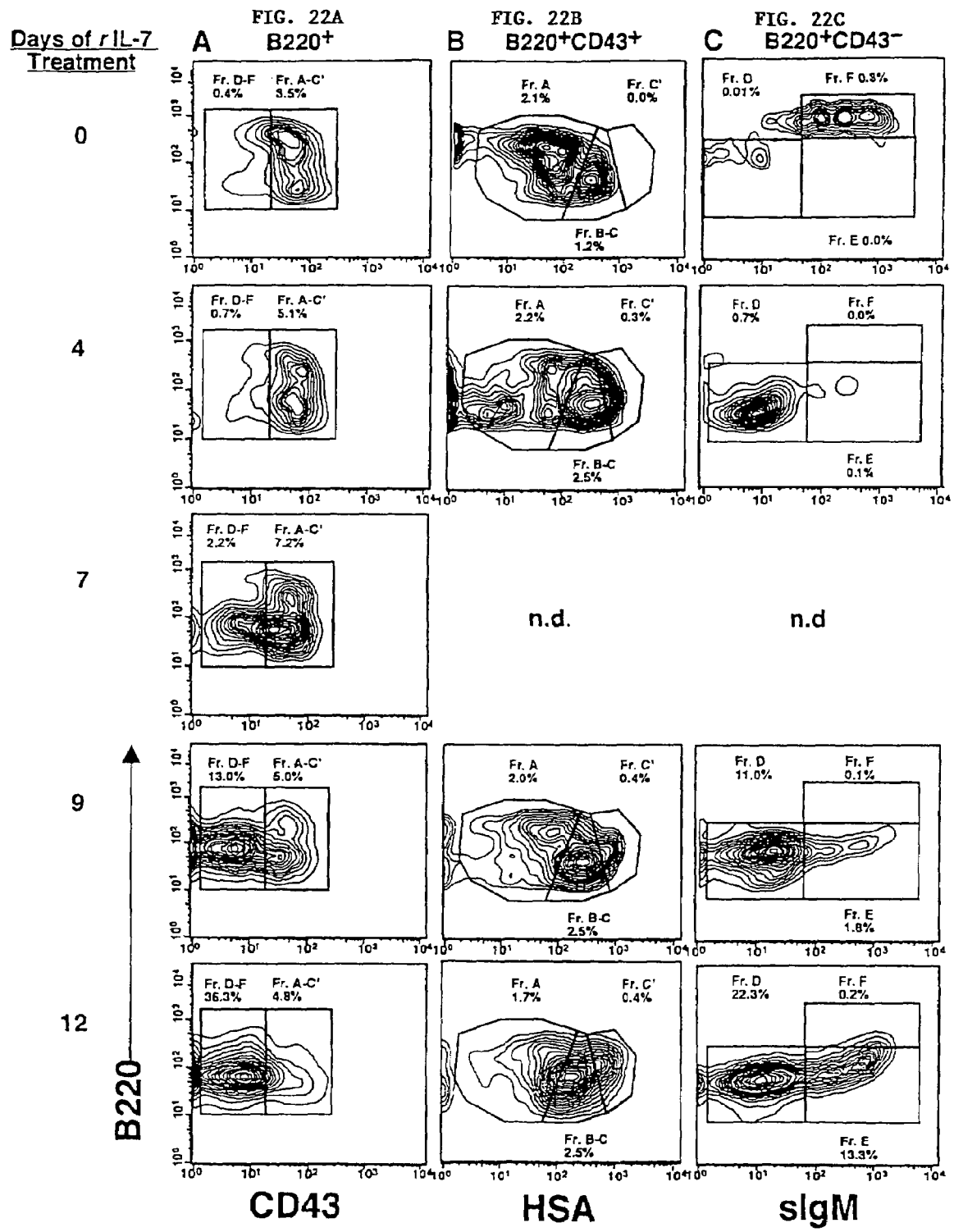
FIG. 22 are a series of flow cytometry histograms of B-cell populations demonstrating the effect of in vivo injection of rIL-7 into IL-7 KO mice on the development of B-lineage cells in BM. IL-7 K/O mice were injected i.p. with 40 ng rIL-7 (SEQ ID NO:8) daily for 4, 7, 9, or 12 days. BM cells were harvested on day 0 or 1 day after the end of each series of injections, and were subjected to FCM analysis. (A) The B220+ population was subdivided into CD43+ (Fr. A-C') and CD43− (Fr. D-F) cells according to relative fluorescence intensity. (B) The B220+CD43+ population was subdivided into Fr. A, B-C and C' according to relative fluorescence intensity for HSA. (C) The B220+CD43− population was separated into Fr. D, E and F according to relative fluorescence intensity for sIgM. The relative numbers of cells in each of these fractions is expressed as the percentage of total nucleated BM cells per femur. (n.d.=not determined).

In Vivo Treatment with rIL-7 (SEQ ID NO:7, 8) Restores B Cell Development in IL-7 K/O Mice. IL-7 K/O mice were injected i.p. daily with rIL-7 to confirm the essential role of IL-7 on early B cell development in vivo. As shown in FIG. 22A, the proportion of B220+CD43+ (Fr. A-C') cells among total BM cells progressively increased during the first 7 days of treatment, and that of B220+CD43− (Fr. D-F) cells between days 7 and 12. Subset analysis with HSA (FIG. 22B) and sIgM (FIG. 22C) showed sequentially overlapping increases in pro-B cells (Fr. B-C), transitional cells (Fr. C'), pre-B cells (Fr. D) and immature B cells (Fr. E) between days 4 and 12. However, at day 12, the proportion of mature B cells (Fr. F) did not exceed that at day 0 (i.e. 10% of normal).

Other studies have shown that within 4 days of i.p. administration of rIL-7 (SEQ ID NO:7, 8), the expression of IL-7R-alpha, TdT and cμ. by pro-B cells and transitional pre-B cells was restored to normal levels in BM of IL-7 K/O mice; and these cells were responsive to further stimulation with rIL-7 in vitro. Pre-B cell development was detected in vivo by day 7 of rIL-7 treatment, and sIgM+ B-cell development by day nine. It remains to be determined if the effects of IL-7 reconstitution in IL-7 K/O mice (especially at the pre-pro-B and pro-B cell stages) is due to the formation of PPBSF in vivo.

In Vivo Treatment with rIL-7 (SEQ ID NO:7, 8) enables B220+CD43+B-lineage Cells From IL-7 K/O Mice to Respond to rIL-7 In Vitro. The present inventors have previously demonstrated that pro-B cells in IL-7 K/O mice express abnormally low levels of IL-7R-alpha, TdT and cμ, and that expression of these proteins increases to normal levels after in vivo reconstitution with rIL-7 (SEQ ID NO:7, 8).

Figures 23A, 23B:
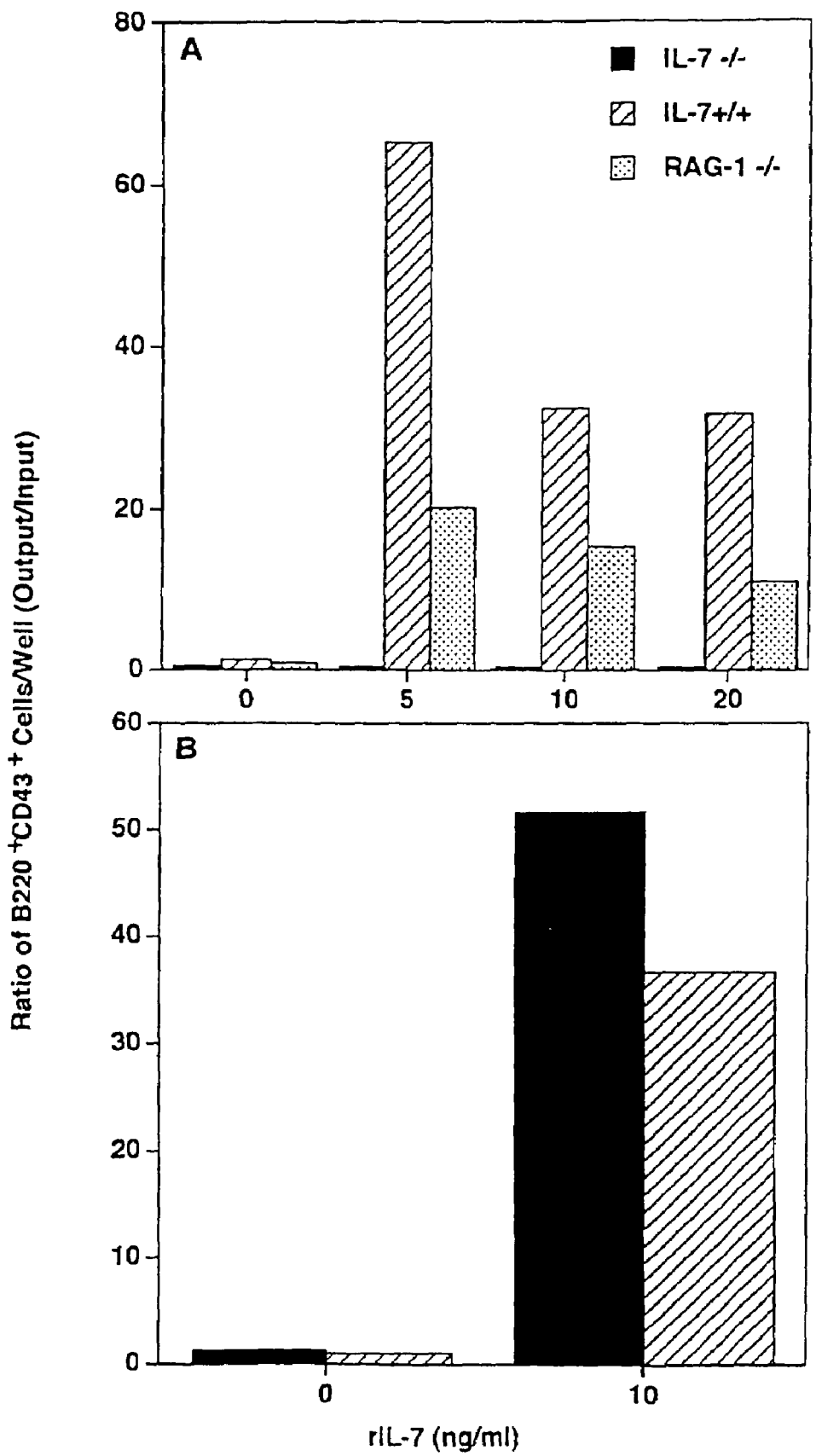
FIGS. 23A and 23B are bar graphs demonstrating the ability of rIL-7 (SEQ ID NO:8) to support the generation of B220+CD43+ cells from IL-7 K/O mice in vitro. $1\times10^6$ BM cells from IL-7 K/O (−/−) mice, obtained (A) before or (B) 4 days after the onset of in vivo treatment with rIL-7, were incubated with medium (RPMI 1640 supplemented with 5% FBS and $5\times10^{-5}$ M 2 ME) containing the indicated concentrations of rIL-7. BM cells from untreated IL-7 competent (+/+) and RAG-1 K/O (−/−) mice were incubated under the same culture conditions. Cells were harvested 4 days later and the results were expressed as the ratio of the input and output numbers of B220+CD43+ cells/well.

As illustrated in FIG. 23A that BM cells from IL-7 K/O mice, unlike those from WT and RAG-1 K/O mice, fail to generate B220+CD43+pre-pro-B/pro-B cells in vitro when stimulated with graded concentrations of rIL-7 (SEQ ID NO:7, 8). In contrast, BM cells from day 4 mL-7-reconstituted IL-7 K/O mice were as efficient as were those from IL-7 competent mice in generating B220+CD43+ cells when stimulated in vitro with rIL-7 (FIG. 23B). The RAG-1 K/O mice, whose pro-B cells express normal levels of IL-7R-alpha and TdT, were included to control for the absence of c, expression, pre-BCR formation and Fr C'cells in IL-7 K/O mice. Although these defects substantially reduced the maximal level of responsiveness to rIL-7 (FIG. 23A), a 20-fold increase in the number of B220+CD43+ cell/well above input levels was still observed.

Figure 24:
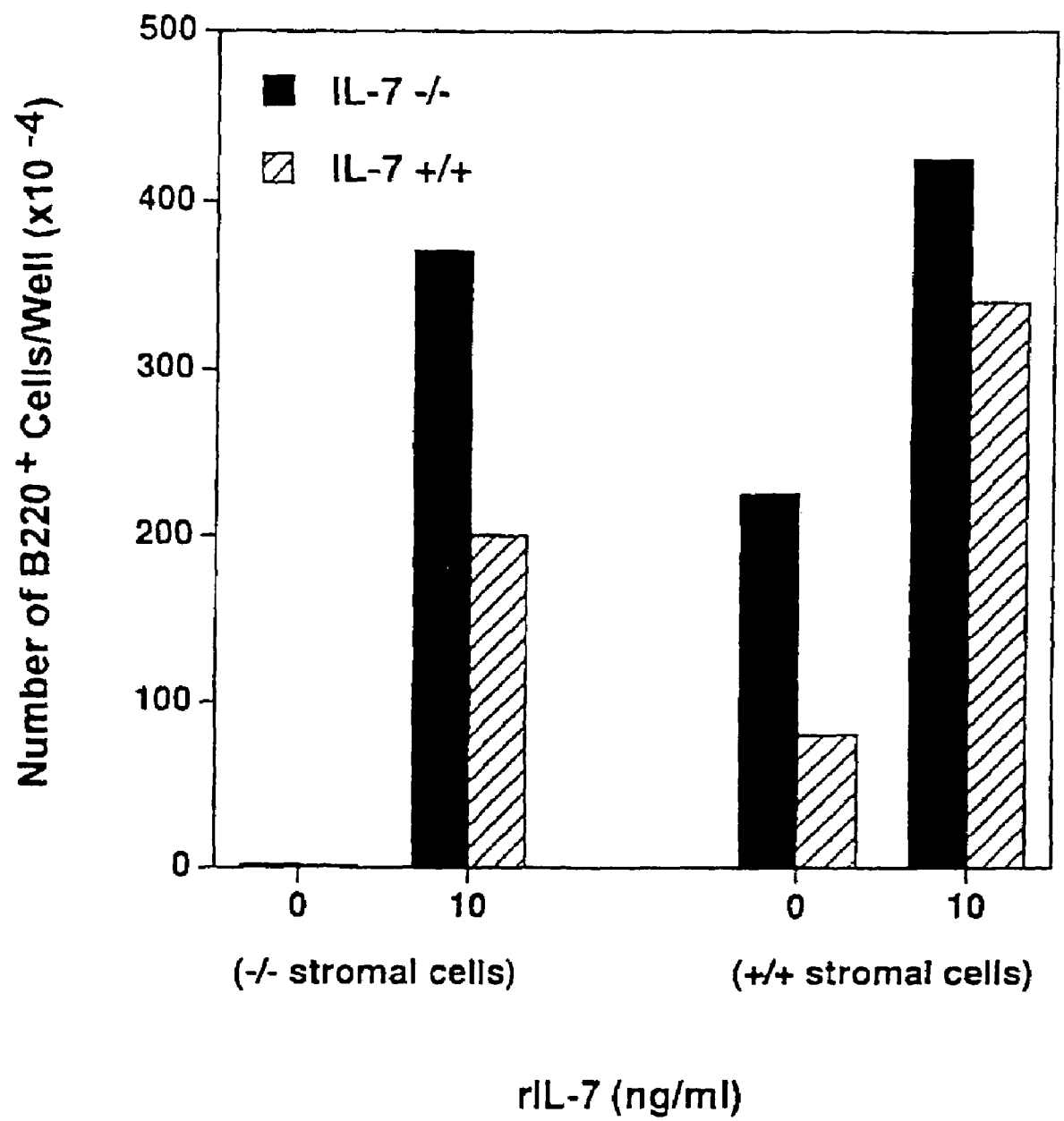
FIG. 24 is a bar graph demonstrating the ability of BM stromal cells from IL-7 (+/+) or IL-7 (−/−) mice to support the in vitro generation of B-lineage cells from IL-7 K/O mice in the presence or absence of rIL-7. $1\times10^6$ BM cells from IL-7 (+/+) and IL-7 (−/−) mice were incubated in the presence or absence of 10 ng/ml rIL-7 (SEQ ID NO:8) on stromal cell layers established from either IL-7 (+/+) or IL-7 (−/−) mice. Cells were harvested on day 10 and the number of B220+ cells per well were calculated.

Both rIL-7 (SEQ ID NO:7, 8) and BM Stromal Cell-derived Signals are Required to Stimulate B220+CD43+ Cells from IL-7 K/O Mice In Vitro. Since rIL-7 (SEQ ID NO:7, 8) was not sufficient to stimulate B220+CD43+ BM cells from untreated IL-7 K/O mice to proliferate in vitro, it was determined whether BM stromal cell layers could provide the necessary additional signals. As shown in FIG. 24, IL-7 (−/−) as well as IL-7 (+/+) BM stromal cell layers enabled rIL-7 to support the growth of B-lineage cells in vitro. Although, IL-7 (+/+) BM stromal cells were sufficient by themselves, additional growth occurred in the presence of rIL-7.

Figure 25A:
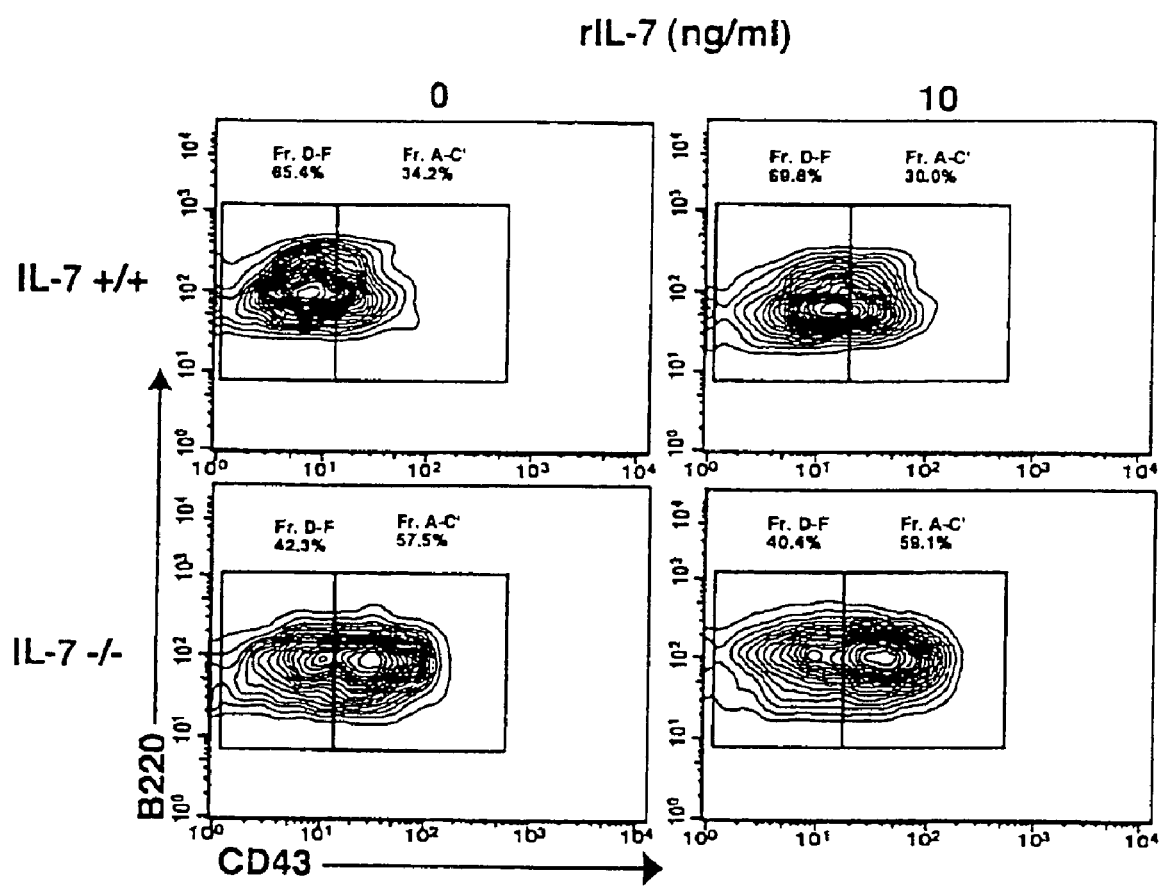
FIGS. 25A and 25B are flow cytometry histograms demonstrating phenotypic analysis of B-lineage cells generated in vitro on IL-7 (+/+) BM stromal cells in the presence or absence of rIL-7 (SEQ ID NO:8). Day 10 culture-generated B-lineage cells from IL-7 (+/+) and IL-7 (−/−) mice (see FIG. 23, +/+ stromal cells) were analyzed for the expression of B220, CD43 and IL-7R-alpha. (A) Proportions of CD43+ (Fr. A-C') and CD43− (Fr. D-F) cells among the B220+ population. (B) Proportions of IL-7R-alpha$^{lo}$ and IL-7R-alpha$^{hi}$ cells among the B220+CD43+ population. Fewer than 10% Fr. D-F and 5% IL-7R-alpha$^{hi}$ cells were present in the input population (day 0)
Figure 25B:
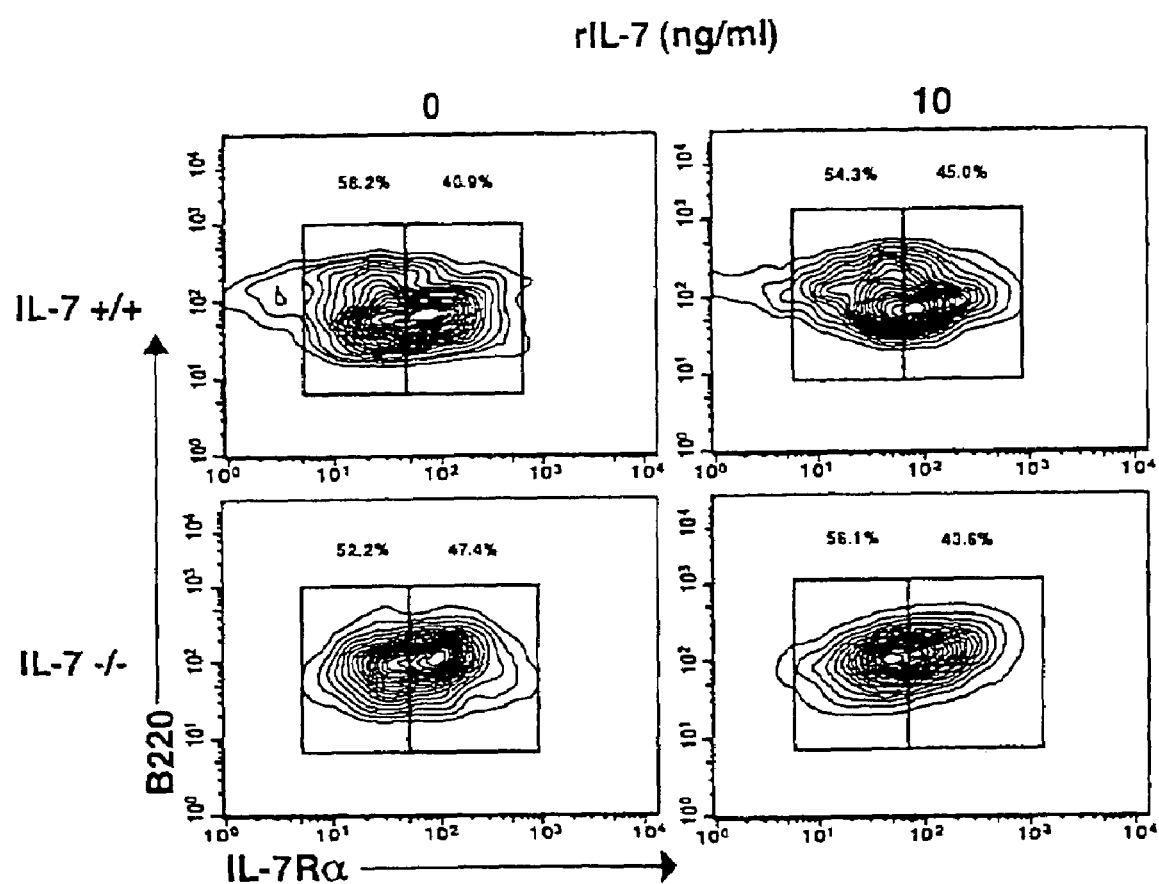
Figure 26:
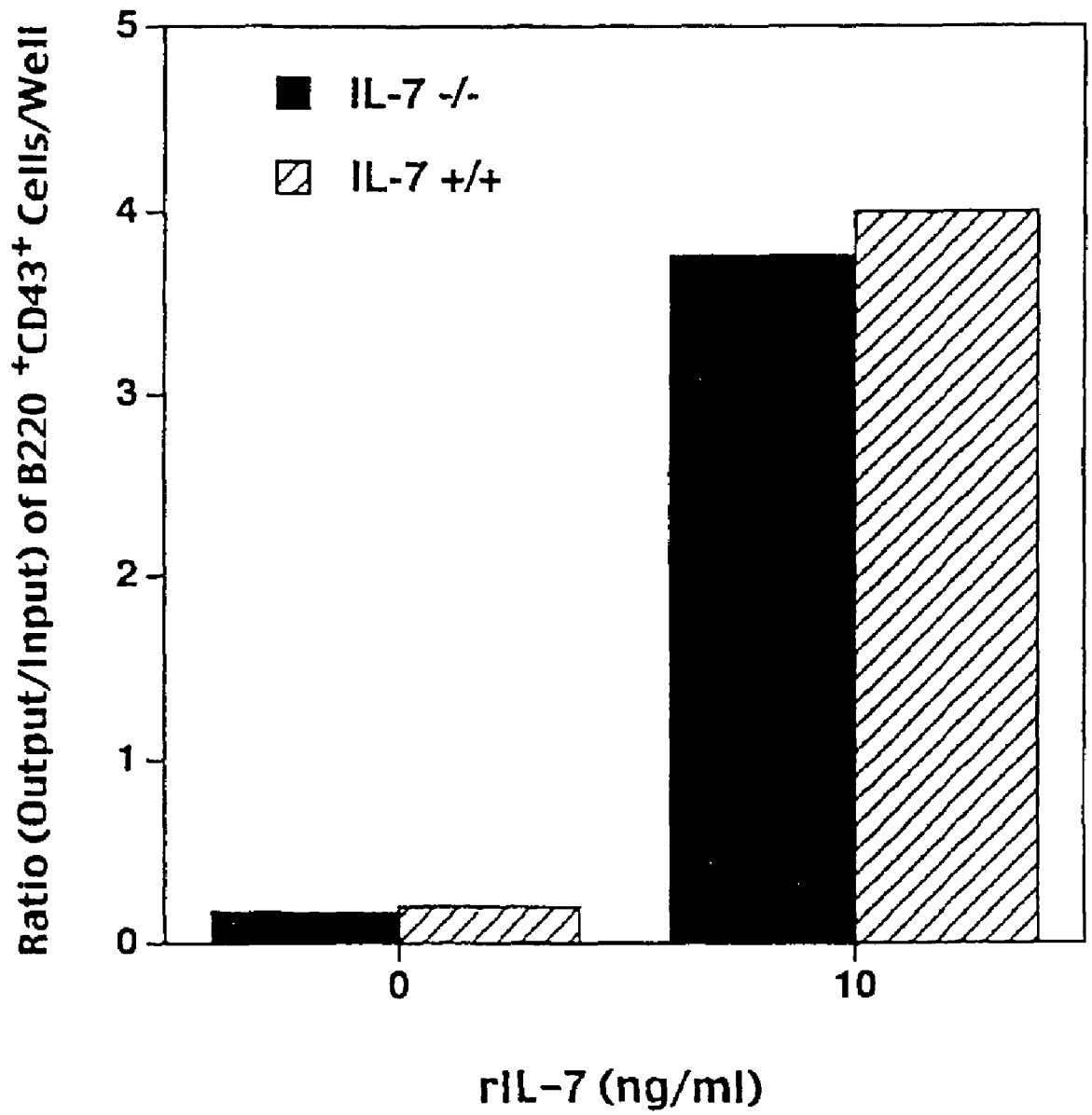
FIG. 26 is a bar graph demonstrating the ability of culture-generated B-lineage cells from IL-7 K/O mice to respond to rIL-7 alone (SEQ ID NO:8). $1\times10^5$ B-lineage cells from day 10 primary cultures containing +/+ stromal cells and 10 ng/ml rIL-7 (see FIG. 23) were transferred into secondary cultures containing medium only or medium plus 10 ng/ml rIL-7. Cells were harvested 4 days later and the numbers of B220+ CD42+ cells/well were determined. Results are expressed as the ratio of output to input numbers of cells/well.

Phenotypic analysis of the IL-7 K/O B-lineage cells generated in primary cultures containing IL-7-competent stromal cells showed that approximately 40% had matured to at least the pre-B cell stage (B220+CD43−) and that additional rIL-7 was not required, (FIG. 25A). Examination of the pre-pro-B/ pro-B (B220+CD43+) cell fraction from these cultures (FIG. 25B) revealed that the expression of IL-7R-alpha was up-regulated on about 45% of the IL-7 K/O cells. Furthermore, when the B220+ cells from these primary cultures were transferred to stromal cell-deficient secondary cultures, they continued to proliferate in response to rIL-7 alone (FIG. 26).

Up-regulation of IL-7R-alpha Expression on B220+ CD43+ Cells From IL-7 K/O Mice In Vitro. The growth to the pre-pro-B and pro-B cell stages was restricted by using the stromal-cell-dependent pro-B cell culture system, as optimized for mouse BM cells by the presence of both IL-7 (+/+) BM stromal cells and 10 μg/ml rIL-7. As in the pre-B-type cultures (FIG. 25B), up-regulated expression of IL-7R-alpha was observed on approximately 50% of the IL-7 K/O B220+ CD43+ cells generated in pro-B-type cultures.

Figure 27:
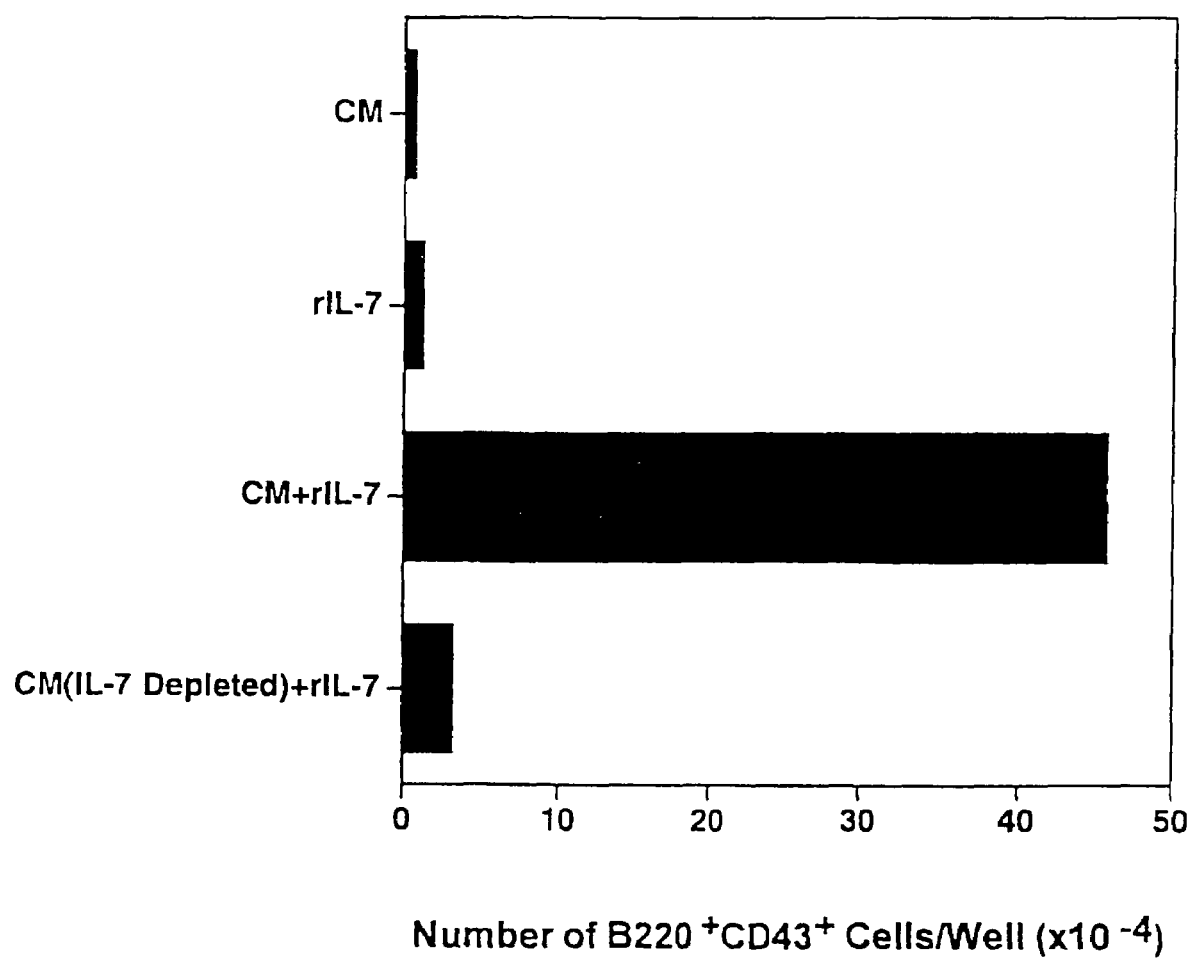
FIG. 27 is a bar graph illustrating that CM plus rIL-7 (SEQ ID NO:8) supports the proliferation of B220+CD43+ cells from IL-7 K/O mice in vitro. $1\times10^6$ BM cells from IL-7 K/O mice were incubated for 20 days in medium (RPMI 1640 supplemented with 20% FBS) containing CM from WT BM stromal cells, rIL-7 (10 ng/ml), or both. The CM was either depleted by adsorption with anti-IL-7 mAb or sham-depleted with an isotype control antibody. The cultures were re-fed (50% volume) twice weekly.
Figure 28:
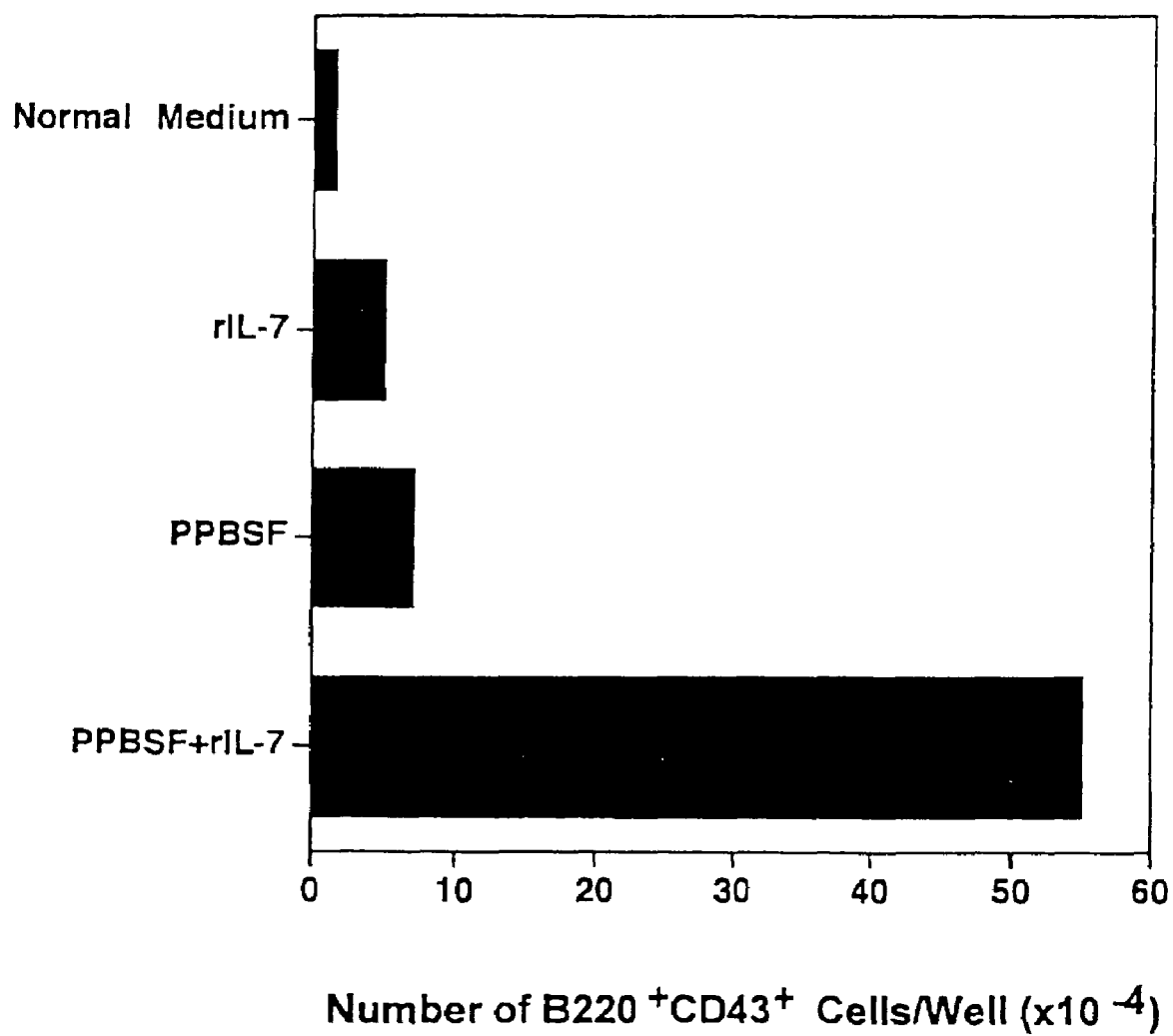
FIG. 28 is a bar graph demonstrating that purified PPBSF plus rIL-7 (SEQ ID NO:8) supports the proliferation of B220+CD43+ cells from IL-7 K/O mice in vitro. $1\times10^6$ BM cells from IL-7 K/O mice were incubated for 20 days with medium containing purified PPBSF (10 ng/ml), rIL-7 (10 ng/ml), or both.
Figure 29:
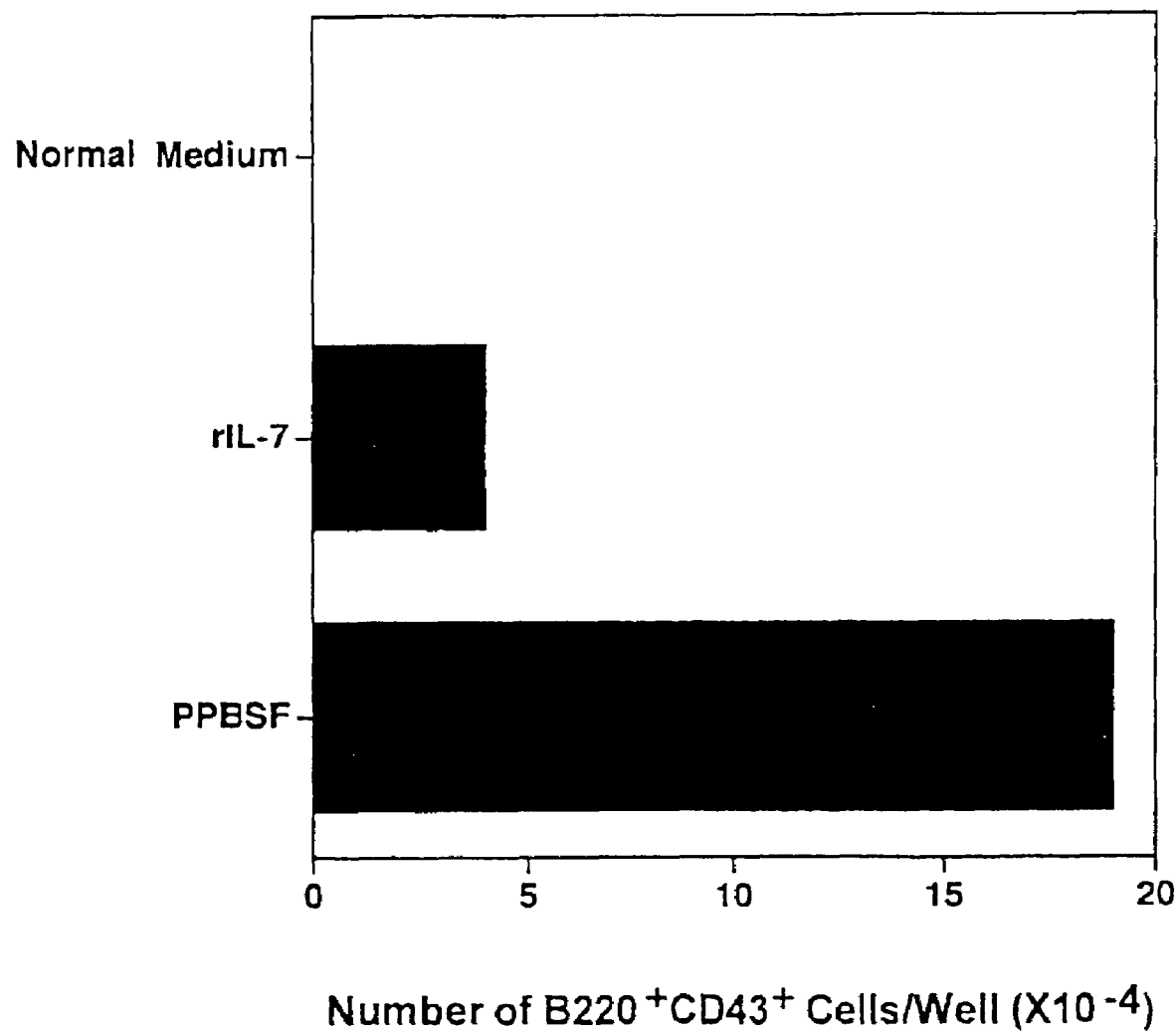
FIG. 29 is a bar graph illustrating the effect of pretreatment in vitro with purified PPBSF, enabling B220+CD43+ cells from IL-7 K/O mice to proliferate in response to rIL-7 (SEQ ID NO:8) alone. $1\times10^6$ BM cells from IL-7 K/O mice were incubated for 5 days with medium containing purified PPBSF (10 ng/ml), or rIL-7 (10 ng/ml). The cells from these primary cultures were transferred into secondary cultures and incubated for another 15 days in medium containing rIL-7 only (10 ng/ml).

Similar results were obtained when CM was substituted for the IL-7 (+/+) stromal cell layers in these cultures (FIG. 27). However, although supplementation with rIL-7 was still required to amplify cell growth, rIL-7 was not able to restore lymphostimulatory activity to CM that had been adsorbed with anti-IL-7 mAb. This observation suggests that the active factor in CM was the heterodimeric form of IL-7, i.e. PPBSF. This was confirmed by demonstrating that purified PPBSF plus rIL-7 (SEQ ID NO:7, 8) could stimulate the in vitro generation of B220+CD43+ cells (FIG. 28). Furthermore, as shown in FIG. 29, PPBSF and rIL-7 appeared to act sequentially. Thus, when BM cells from IL-7 K/O mice were cultured in primary cultures containing PPBSF only, the surviving cells were able to generate B220+CD43+ cells when transferred to secondary cultures containing rIL-7 only. In contrast, although initial exposure to rIL-7 alone maintained the viability of the B220+CD43+ cells from IL-7 K/O BM, it did not enable these cells to proliferate when restimulated with rIL-7.

EXAMPLE 11

Expression and Purification of a Single-chain IL-7 (SEQ ID NO:7, 8)/HGF-beta (SEQ ID NO:3, 4, 13, and 14) Protein. Because the supernatants from the expressed insect cells had the highest thymocyte stimulatory activities (data not shown), this system was chosen for purification and biologic studies of the scIL-7/HGF-beta protein. Inasmuch as the theoretical isoelectricpoint of the scIL-7/HGF-beta is approximately 8, it was reasoned that the protein should carry a positive charge at pH 7, thereby allowing it to flow through DEAE and to bind to CM sepharose resins. However, scIL-7/HGF-beta proteins were eluted from both the DEAE and CM columns. Of importance, the protein that was eluted from the CM column was biologically active. This form of scIL-7/HGF-beta was detected by the goat anti-IL-7 antibody from R&D Systems, but not by the rabbit anti-IL-7 antibody. In contrast, the scIL-7/HGF-beta protein that was eluted from the DEAE column was biologically inactive and was detected by the rabbit, but not the goat, anti-IL-7. Furthermore, only the inactive form of IL-7/HGF-beta reacted with the rabbit anti-HGF-beta antibody, whereas both the active and inactive forms reacted with the goat anti-HGF-beta. In addition, the active form of scIL-7/HGF-beta had a molecular mass of 50 to 55 kDa, compared with 45 to 50 kDa for the inactive form. Inasmuch as the inactive form neither inhibited nor synergized with the active form of scIL-7/HGF-beta (data not shown), only the properties of the active form are described.

EXAMPLE 12

Effect of scIL-7 (SEQ ID NO:7, 8)/HGF-beta (SEQ ID NO:3, 4, 13, and 14) on Early B-lineage Development In Vitro. The activity of the scIL-7/HGF-beta protein on early B lymphocyte development was studied using freshly harvested rat and mouse BM cells. Consistent with previous results, primary rat BM cell cultures generated pre-pro-B cells and pro-B cells in the presence of scIL-7/HGF-beta, whereas cultures containing rIL-7 generated pro-B and pre-B cells almost exclusively (FIG. 31).

Figure 31:
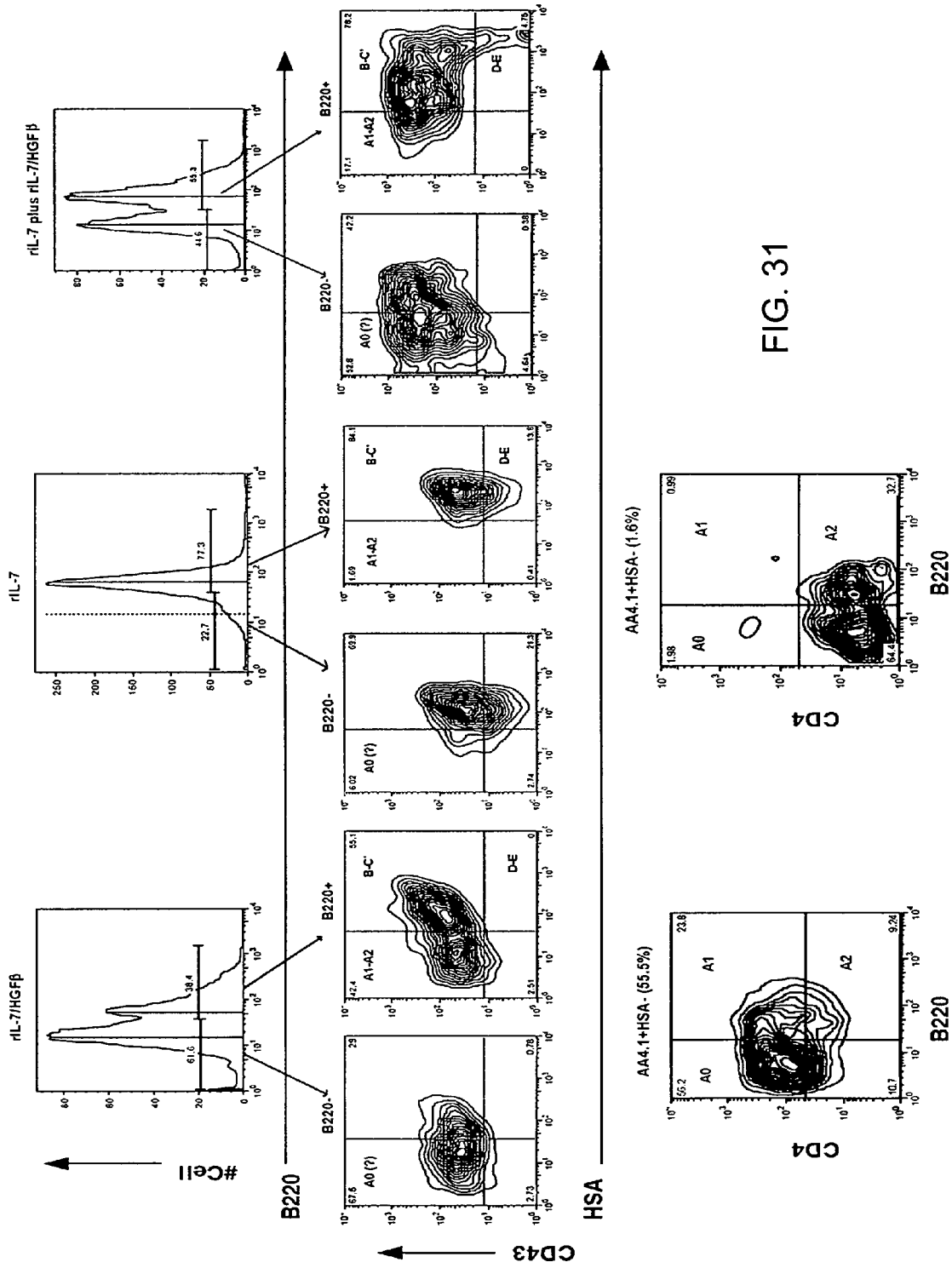
FIG. 31 Stimulation of mouse bone marrow (BM) cells by rIL-7 (SEQ ID NO:8) and/or scIL-7/HGF-beta in vitro. Freshly harvested BM cells from IL-7 (−/−) mice were cultured in RPMI-1640 containing 2-ME in the presence of 10 ng/ml rIL-7 or 30 ng/ml scIL-7/HGF-beta, or both. Nonadherent cells were harvested at day 17 and analyzed by flow immunocytometry. Top row shows representative histograms of B220+ and B220− cells in each culture. The vertical standards indicate the peaks (or theoretical peak; dashed line) of fluorescence intensity and are used to eliminate most of the overlap regions between the peaks. Middle row shows the contour plots for CD43 and HSA of the B220− and B220+ cells to the left and right of the peaks in the top row. The various fractions of developing B-lineage cells and their relative proportions in the B220− and B220+ cell subsets are indicated for each quadrant. Bottom row shows the relative proportion of fractions $A_0$ (CLPs), $A_1$ (early pre-pro-B cells) and $A_2$ (late pre-pro-B cells).
Figure 32:
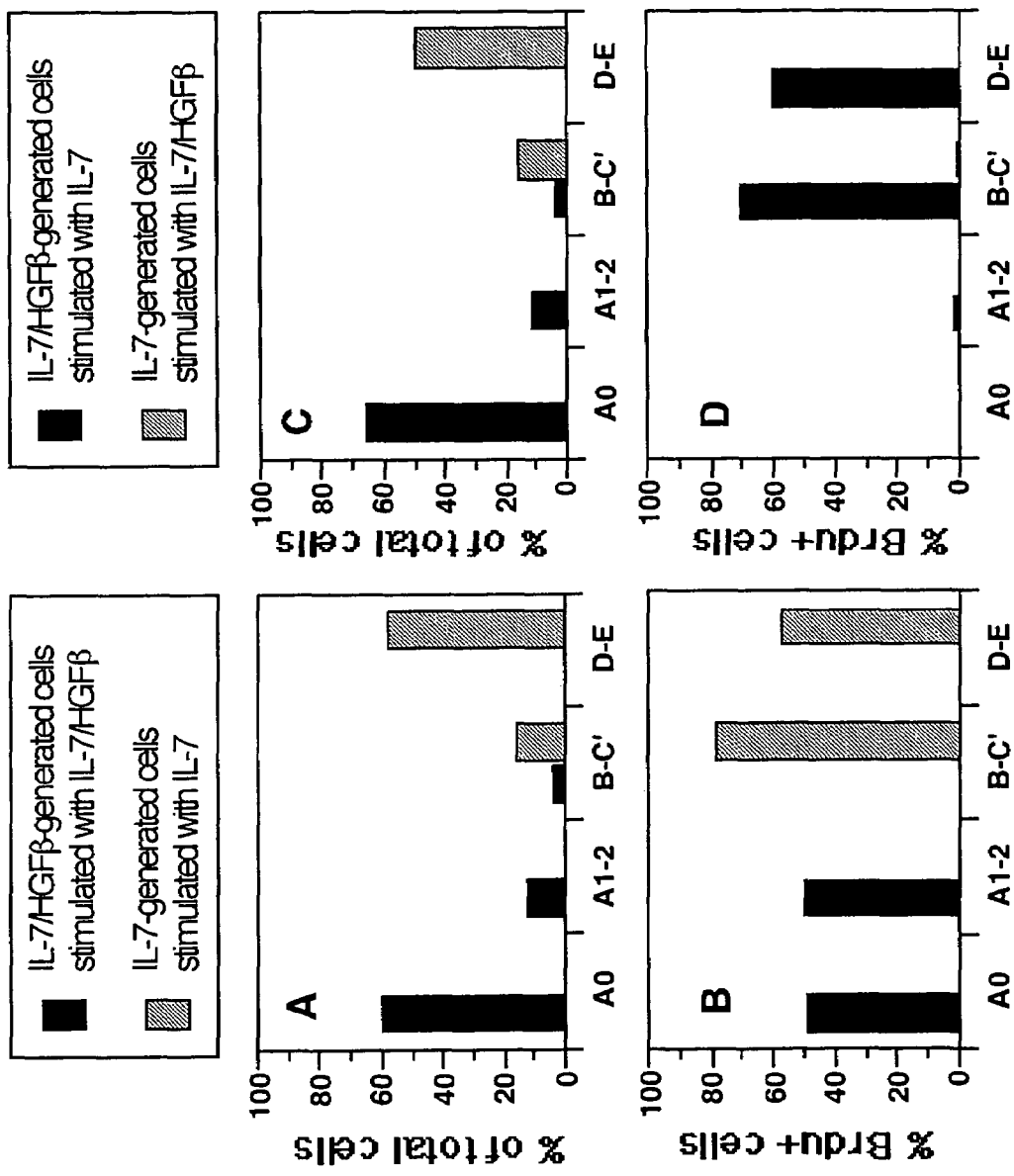
FIG. 32 Incorporation of BrdU by culture-generated BM lymphoid cells stimulated or cross-stimulated in vitro with rIL-7 (SEQ ID NO:8) or scIL-7/HGF-beta. BM cells from IL-7 (−/−) mice were cultured in the presence of rIL-7 (10 ng/ml) or scIL-7/HGF-beta (30 ng/ml) for 19 days. The cells were washed, cytokine-starved for 5 hours, stimulated with the homologous or heterologous cytokine for 3 hours, pulsed with BrdU, and stained with combinations of antibodies to B220, HAS, AA4.1, CD43, CD4, and BrdU. (A, C) Distribution early B-lineage subsets in each culture system. (B, D) Percentage of BrdU+ cells in each fraction of B-lineage cells. (A, B) ■ indicates scIL-7/HGF-beta-generated cells stimulated with scIL-7/HGF-beta; ■ indicates IL-7-generated cells stimulated with IL-7. (C, D) ■ indicates scIL-7/HGF-beta-generated cells stimulated with IL-7; ■ indicates IL-7-generated cells stimulated with scIL-7/HGF-beta. Means of duplicate samples are shown. Data are from 1 representative experiment of 2.

As shown in FIG. 31, mouse BM cells responded somewhat differently than did rat BM cells. Rather than containing B220$^+$ cells only, approximately 60% of the mouse lymphoid cells in these cultures were B220$^-$. Moreover, approximately two thirds of the B220$^-$ cells had a CD43$^+$ HSA$^-$ phenotype, suggesting that some might be CLPs. To substantiate this, the protocol of Hardy and colleagues was used to demonstrate that approximately 0% of the total cells in the scIL-7/HGF-beta treated cultures had the AA4.1$^+$ B220$^-$HSA$^-$ CD4$^{low}$ phenotype characteristic of CLPs (Fraction Ao), 15% were early pre-pro-B cells (Fr. A1), 5% were late pre-pro-B cells (Fr. A2), and 20% were pro-B cells (Fr. B-C1). In contrast, Fr. Ao and A1 cells were absent from cultures containing rIL-7, and only 0.5% were A2 cells. Instead, 65% were pro-B cells (Fr. B-C), and 10% were pre-B cells (Fr. D). Cultures containing equimolar amounts both of IL-7 and scIL-7/HGF-beta contained Fr. Ao through Fr. D cells. When converted into mean numbers of cells per well (Table 1), the results showed an average overall 16-fold increase in output over input numbers of early B-lineage precursors in the scIL-7/HGF-beta cultures, and a 27-fold increase in the rIL-7 cultures. However, the increases seen in the scIL-7/HGF-beta cultures were restricted to the CLP (31-fold), pre-pro-B (8-fold), and pro-B (10-fold) cell fractions, whereas those in the IL-7 cultures involved the pro-B (51-fold) and the pre-B (32-fold) cell fractions only. Furthermore, the results in FIGS. 32A and 32B show that scIL-7/HGF-beta selectively stimulated the proliferation of CLPs and pre-pro-B cells, and rIL-7 of pro-B cells and pre-B cells. Hence, the marked expansion of pro-B cells in the scIL-7/HGF-beta cultures appears to be due primarily to their differentiation from proliferating pro-B cells.

TABLE 1

Generation of B-Lineage Cells in IL-7$^{-/-}$ Bone Marrow Cell Cultures Number of Cells/Well (×10$^{-4}$).

| | scIL-7/HGFβ | | | | | rIL-7 | | | | |
|---|---|---|---|---|---|---|---|---|---|---|
| Cultured BM Cell | CLP | Pre-Pro-B | Pro-B | Pre-B | Total | CLP | Pre-pro-B | Pro-B | Pre-B | Total |
| Input (Day 1) | 2 | 5 | 4 | <1 | 9 | 2 | 5 | 4 | <1 | 9 |
| Output (Day 17) | 62 | 41 | 41 | <1 | 144 | 0 | 2 | 205 | 32 | 239 |
| Fold Increase | 31 | 8 | 10 | 0 | 16 | 0 | 0 | 51 | >32 | 27 |

EXAMPLE 13

Effect of scIL-7 (SEQ ID NO:7, 8)/HGF-beta (SEQ ID NO:3, 4, 13, and 14) on CFU-$S_{12}$. To determine if the scIL-7/HGF-beta supported the survival or proliferation of more primitive lymphohemopoietic precursors than CLPs, irradiated mice were injected intravenously with culture-generated cells, and the number of macroscopically visible spleen colonies was determined 12 days later. Cells ($1 \times 10^6$) from the scIL-7/HGF-beta cultures generated 30±4.2 CFU-$S_{12}$ above background (minimal estimate due to partial confluency), as compared with a mean of only 1 colony for the IL-7 cultures. Histologic examination of the colonies generated by the scIL-7/HGF-beta-cultured cells showed that many contained a mixture of erythroid, myeloid, and megakaryocytic elements. Furthermore, comparison with the CFU-$S_{12}$ activity in freshly harvested BM showed that, on a per-cell basis, the scIL-7/HGF-beta-stimulated cultures contained a normal frequency of CFU-$S_{12}$. However, as the total number of cells in these cultures approximated that in the original inoculum ($2 \times 10^6$), it was not possible to determine whether scIL-7/HGF-beta maintained prolonged survival (15 days) of CFU-$S_{12}$ or stimulated their (or their precursors') proliferation. Therefore, experiments were repeated using cultures to which c-kitL (50 ng/mL) and flt-3L (50 ng/mL) had been added. Within 7 days, both the scIL/HGF-beta and rIL-7 cultures contained approximately 5-fold more cells ($8.8 \times 10^6$ to $12.8 \times 10^6$) than were present in the original inoculum. Again, only the scIL-7/HGF-beta cultures contained significant CFU-$S_{12}$ activity above background (c-kitL plus flt-3L only). However, as the total CFU-$S_{12}$ activity per culture well exceeded the input activity by approximately 5-fold, it would appear the number of CFU-$S_{12}$ in the scIL-7/HGF-beta cultures had expanded by at least that amount.

EXAMPLE 14

Effect of scIL-7 (SEQ ID NO:7, 8)/HGF-beta (SEQ ID NO:3, 4, 13, and 14) on Early B-lineage Development In Vivo. To determine whether the culture-generated cells had functional lymphoid progenitor activity in vivo, $1 \times 10^6$ cells from cultures containing equimolar amounts of rIL-7 or scIL-7/HGF-beta were injected intravenously into sublethally irradiated CD45-congenic mice. The results in Tables 1 and 2 show that, at 3 weeks, the cells from the scIL-7/HGF-beta cultures generated 3- to 4-fold more splenic B-lineage cells than did those from the rIL-7 cultures, and the proportion of donor-origin B-lineage cells that had passed the pro-B cell stage greatly exceeded that in recipients of IL-7-cultured cells ($P<0.01$). Furthermore, the B-cell generative activity of $1 \times 10^6$ cells from the scIL-7/HGF-beta-containing cultures was equivalent quantitatively and qualitatively to that of a saturating dose ($20 \times 10^6$) of normal BM cells, even though the latter contains a heterogeneity of cell types that might serve as lymphoid progenitors.

TABLE 2

In Vivo Lymphoid Progenitor Activity of Culture-Generated BM Cells.

| In Vitro Treatment, Number of Cells Injected | Number of Donor-Origin B Cells, $\times 10^6$ | |
|---|---|---|
| | Bone Marrow | Spleen |
| rIL-7, $1 \times 10^6$ | 12.8 ± 2.0 | 2.3 ± 0.2 |
| scIL-7/HGF-beta, $1 \times 10^6$ | 11.6 ± 4.7 | 8.2 ± 1.2* |
| Normal BM cells, $20 \times 10^6$ | 13.5 ± 5.3 | 10.7 ± 0.9 |

TABLE 3

Subsets of Donor-Origin B Cells in BM.

| In Vitro treatment | % of B-lineage cells | |
|---|---|---|
| | Pre-pro-B and pro-B | Pre-B and immature B |
| rIL-7 | 85.3 ± 11.8 | 14.4 ± 11.3 |
| scIL-7/HGFβ | *62.5 ± 16.7 | *36.8 ± 17.8 |
| Normal BM cells | 61.4 ± 5.2 | 38.5 ± 5.2 |

*$p < .05$ between rIL-7 and scIL-7/HGFβ-treated cells.

EXAMPLE 15

Figure 33:
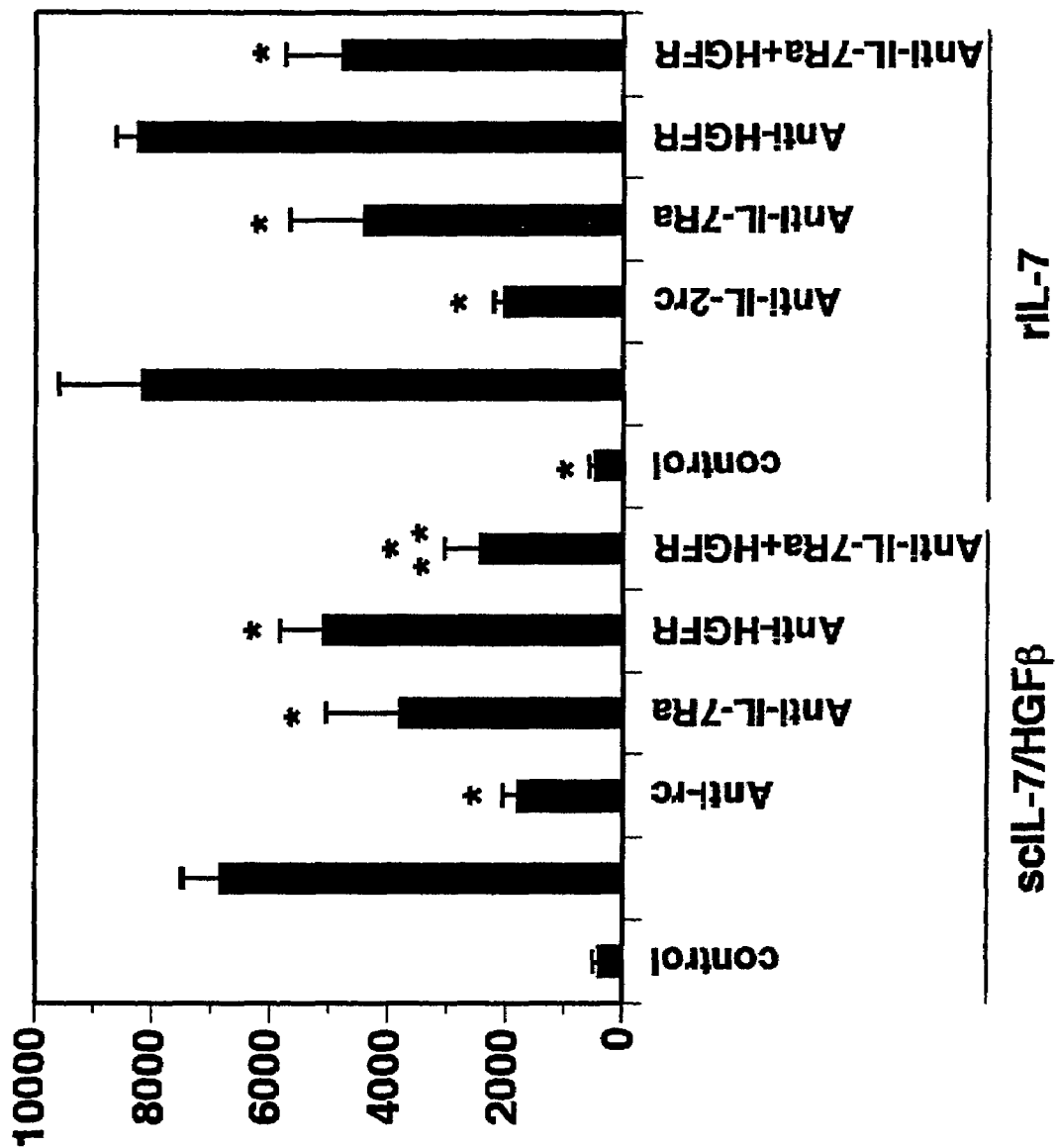
FIG. 33 Ability of antibodies to the IL-7 Receptor (R) and/or c-Met to inhibit the stimulation of mouse bone marrow cells by rIL-7 (SEQ ID NO:8) or scIL-7/HGF-beta. Culture-generated BM cells ($4\times10^5$ cells/well) from IL-7 (−/−) mice were incubated for 3 days in the presence of rIL-7 (10 ng/ml) or scIL-7/HGF-beta (30 ng/ml) to which antibodies against IL-7R-alpha, γc, and/or c-Met (10 μg/ml) were added. Incorporation of [methyl-3H] thymidine (mean counts per minute [CPM]±SD) was determined after a 12-hour pulse. *$P<0.05$ between antibody-treated and untreated values (similar results were obtained with isotype controls). **$P<0.05$ versus value for anti-IL-7R-alpha or anti-HGFR alone. One representative experiment of 4 is shown.

Identity of the Receptor Complex for scIL-7 (SEQ ID NO:7, 8)/HGF-beta (SEQ ID NO:3, 4, 13, and 14). Ordinarily, IL-7 binds to the alpha and gamma-c chains of the IL-7R whereas the alpha chain of mature HGF binds to the HGFR, c-Met. However, it is not known if the HGF-beta chain also binds to c-Met. Therefore, to gain some insight into the nature of the receptor(s) for the scIL-7/HGF-beta, antibodies specific for the IL-7R-alpha chain, the gamma-c chain or c-Met were added to cultures of mouse early B-lineage cells generated in the presence of rIL-7 or scIL-7/HGF-beta. As shown in FIG. 33, the ability of scIL-7/HGF-beta to stimulate the proliferation of BM lymphoid cells was partially, but significantly ($P<0.05$), inhibited by antibodies to c-Met as well as those to the IL-7R-alpha and gamma-c chains. Also, a mixture of anti-c-Met and anti-IL-7R-alpha antibodies showed greater inhibition than did either antibody alone. In contrast, only the antibodies to the IL-7R-alpha and gamma-c chains inhibited proliferation stimulated by rIL-7.

Figure 34:
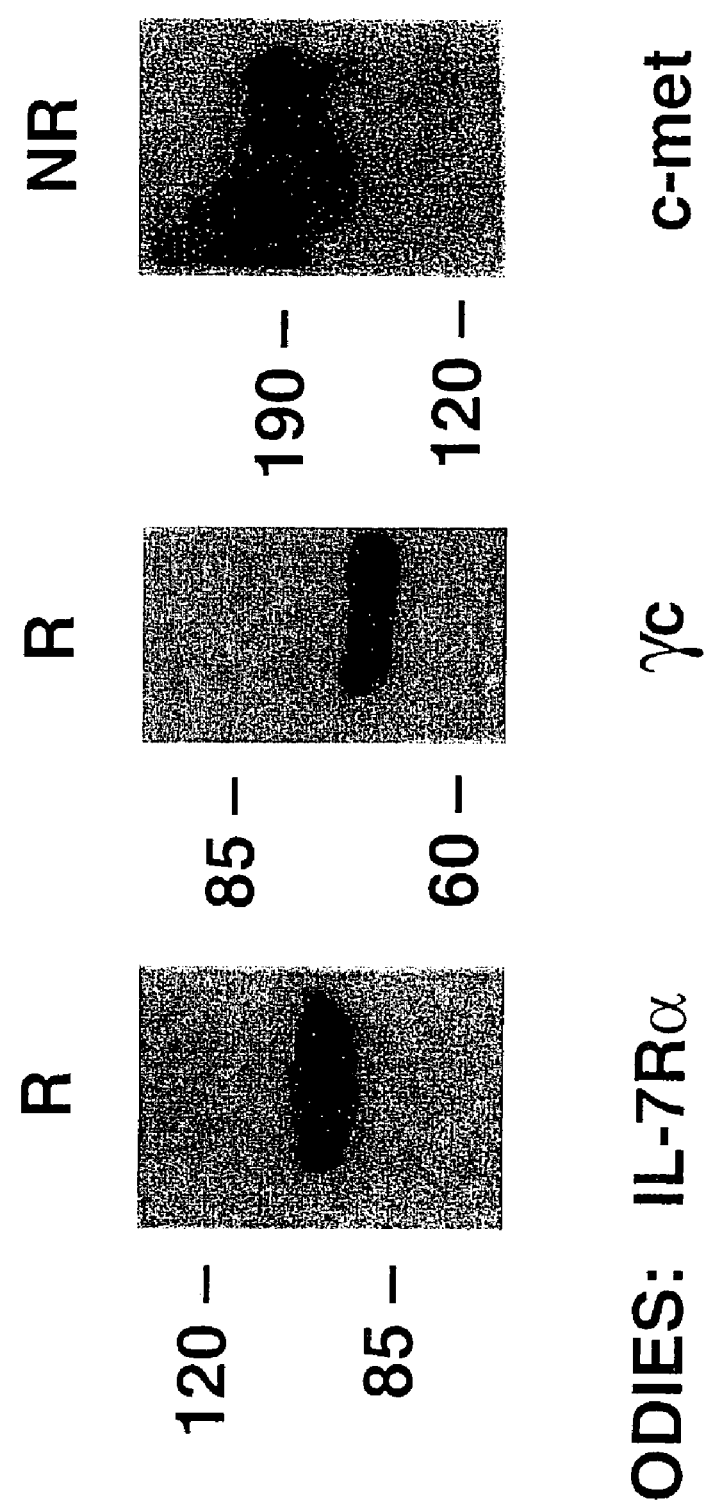
FIG. 34 Analysis of the purified IL-7/HGF-beta receptor proteins. The IL-7/HGF-beta receptor complex was isolated on a scIL-7/HGF-beta affinity gel from purified culture-generated CLP/pre-pro-B cells. The eluates were subjected to SDS-PAGE under reducing (R) or nonreducing (NR) conditions, and Western blotting was done with antibodies to IL-7R-alpha, γc, or c-Met.
Figure 35:
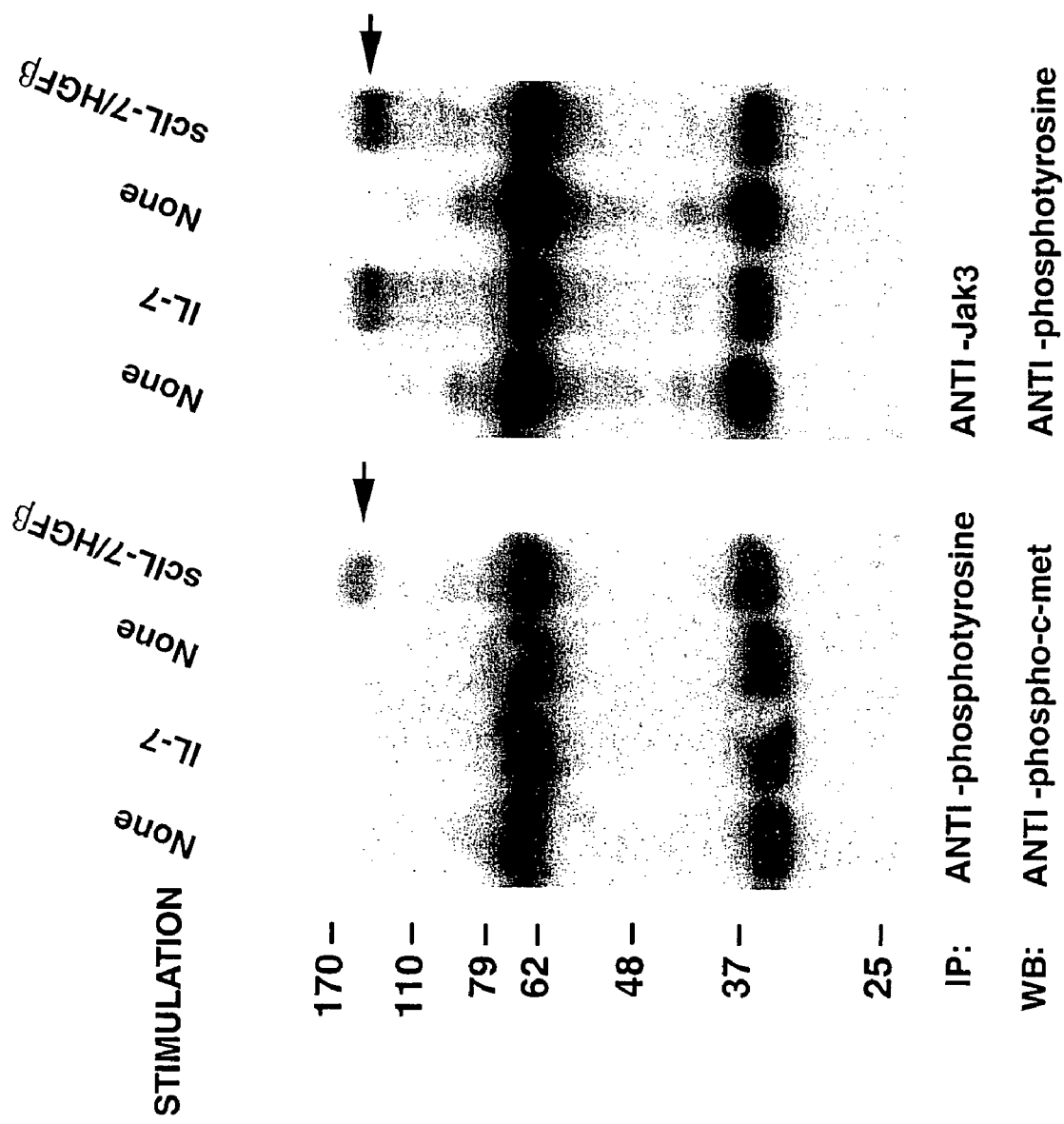
FIG. 35 Ability of rIL-7 (SEQ ID NO:8) or scIL-7/HGF-beta to activate Jak3 and/or c-Met in mouse B-lineage bone marrow cells. B-lineage cells generated in cultures of IL-7 (−/−) mouse BM cells supplemented with rIL-7 or scIL-7/HGF-beta were harvested, placed in cytokine-free medium for 5 hours, and then stimulated with the homologous cytokine for 10 or 30 minutes. The supernatants form lysed cells were immunoprecipitated with anti-Jak3 or antiphosphotyrosine antibody and subjected to SDS-PAGE and Western blotting using the indicated antibodies. Arrows indicate phosphor-c-Met or phosphor-Jak3. Phosphorylation of Jak3 was used as an indicator of IL-7R signaling, and positive Western Blotting with anti-c-Met phosphospecific antibody as an indicator of c-Met signaling. The figures indicates that both rIL-7 and scIL-7/HGF-beta signal through the IL-7R, but that only scIL-7/HGF-beta signals through c-Met as well.
Figure 36:
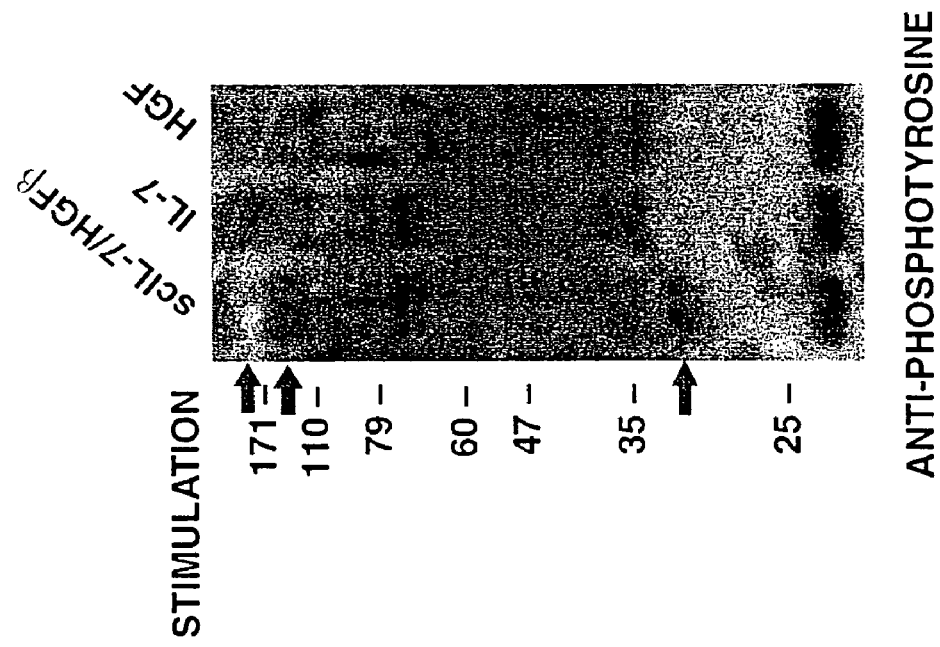
FIG. 36 Signal transduction via a phosphotyrosine pathway. To demonstrate that scIL-7/HGF-beta signals through a different pathway from IL-7 (SEQ ID NO:7, 8) or HGF alone (SEQ ID NO:5, 6) tyronsine phosphorylation of whole cell lysates was analyzed by Western Blot developed with anti-phosphotyrosine antibodies. The results indicate differences in phosphorylation profiles between the IL-7-stimulated and HGF-stimulated cells, and also the IL-7/HGF-beta stimulated cells. Most striking was the appearance of 2 novel bands of phosphorylated proteins of approximately 30 kDa and 140 kDa in the scIL-7/HGF-beta-stimulated cells and the absence of a 180 kDa band (see arrows). These results are consistent with following non-limiting hypothesis; that IL-7/HGF-beta induces "cross-talk" between the IL-7 and c-Met receptors, which in turn activates new signaling pathways and induces new biological functions than those induced by IL-7 and HGF alone.

Consistent with these blocking experiments, approximately 60% of the scIL-7/HGF-beta culture-generated CLPs and pre-pro-B cells expressed both c-Met and the IL-7R, whereas more than 80% at the rIL-7 culture-generated pro-B cells expressed the IL-7R only (data not shown). Furthermore, confocal microscopy revealed that the IL-7 and c-Met receptors existed as aggregates that had undergone patching and capping on cells stimulated with scIL-7/HGF-beta but not rIL-7 (data not shown). Of interest, similar IL-7R/c-Met complexes were observed on enriched pre-pro-B cell fractions from normal (noncultured) BM, suggesting that they may have been stimulated by endogenous IL-7/HGF-beta. In addition, cross stimulation studies (FIGS. 32C-D) revealed that rIL-7 did not stimulate the proliferation of CLPs or pre-pro-B cells from scIL-7/HGF-beta cultures, and that scIL-7/HGF-beta did not stimulate pro-B cells or pre-B cells from rIL-7 cultures. However, as noted previously for native IL-7/HGF-beta, scIL-7/HGF-beta was able to "prime" pre-pro-B/pro-B cells to respond to rIL-7 (FIG. 32D), presumably by up-regulating the IL-7R-alpha chain. Hence, in their aggregate, these results suggest that the scIL-7/HGF-beta hybrid cytokine binds coordinately to the IL-7 and HGF receptors on B-cell precursors, whereas rIL-7 binds to the IL-7R only. Direct evidence that both the IL-7R (alpha and gamma-c chains) and c-Met are major components of the receptor complex for IL-7/HGF-beta was provided on Western blots after purification of receptor proteins from culture-generated CLPs/pre-pro-B cells on a scIL-7/HGF-beta affinity gel (FIG. 34). In addition, demonstration that the binding of scIL-7/HGF-beta to early B-lineage cells initiates signal transduction through both the IL-7R and c-Met was provided by analysis of phosphorylation of Jak3 (which associates with the gamma-c chain of the IL-7R complex) and Western blotting with anti-c-Met phosphospecific antibody. Results in FIG. 35 show that both rIL-7 and scIL-7/HGF-beta transduce signals through the IL-7R, but that only scIL-7/HGF-beta signals through c-Met as well.

Exemplary Materials and Methods.

Animals. 129XB6F2 IL-7 (−/−) and IL-7 (−/−) mice (generously provided by Dr Richard Murray, DNAX Research Institute of Cellular and Molecular Biology, Palo Alto, Calif.) and Lewis strain rats were used as donors and/or recipients of BM lymphoid precursor cells and thymocytes.

Cytokines and antibodies. Recombinant IL-7 (SEQ ID NO:7, 8) and goat polyclonal antibodies (Abs) against mouse IL-7 (SEQ ID NO:8), IL-7R-alpha, gamma-c chain, and c-Met (R&D Systems, Minneapolis, Minn.); goat and rabbit polyclonal antibodies against human and mouse HGF-beta, rabbit anti-IL-7, and horseradish peroxidase (HRP)-linked anti-goat and anti-mouse immunoglobulin G (IgG) antibodies (Santa Cruz Biotechnology, Santa Cruz, Calif.); HRP anti-rabbit IgG antibody (Amersham Biosciences, Piscataway, N.J.); phycoerythrin (PE), biotin-conjugated, and unconjugated mouse monoclonal antibodies (mAbs) against rat HIS24 (CD45R-B220), HIS1 7 (CD43), HIS50 (HSA), and fluorescein isothiocyanate (FITC), PE, biotin, and allophycocyanin (APC)-conjugated anti-mouse B220, anti-HSA and anti-CD43 Abs (BD Biosciences, San Diego, Calif.); FITC and APC anti-IL-7R-alpha, APC anti-mouse CD4, and PE anti-AA4.1 (Bioscience, San Diego, Calif.); Alexa fluor 594-labeled anti-goat IgG (Molecular Probes, Eugene, Oreg.); anti-CD19, B220, and PE MicroBeads (Miltenyi Biotec, Auburn, Calif.); anti-Jak3 and phosphotyrosine (4G10) (Upstate Biotechnology, Lake Placid, N.Y.); and anti-phospho-c-Met (Biosource, Camarillo, Calif.).

Thymidine incorporation. Thymocytes or culture-generated BM lymphoid cells were seeded in triplicate into 96-well plates, and 0.074 MBq (2 µCi) [$^3$H] thymidine was added to each well 12 hours before completion of the 72-hour incubation period. Incorporation of [$^3$H] thymidine was determined by liquid scintillation spectroscopy.

BrdU incorporation. BrdU solution (10 µL of 1 mM; BD Biosciences) was added per milliliter of cultured BM cells. The treated cells were incubated at 37° C. for 45 minutes, and stained with fluorescent antibodies for cell-surface markers. After fixation and treatment with DNase, the cells were stained with APC-labeled anti-BrdU antibody and analyzed by flow cytometry.

Immunomagnetic cell separation. BM cells were stained with CD19 MicroBeads for 15 minutes at 4° C., washed, and then applied to a magnetic-activated cell sorter (MACS) magnetic column. The CD19$^-$ cells were reacted with anti-B220 MicroBeads, and the CD19$^-$B220$^+$ cells were isolated by immunomagnetic separation (IMS). Alternately, CD19$^-$ cells were stained with PE-anti-AA4.1 Ab and anti-PE MicroBeads, and the CD 19$^-$AA4.1$^+$ cells were collected.

Confocal microscopy. Cytospin preparations of culture-generated BM lymphoid cells or enriched pre-pro-B cells from fresh BM were fixed with 4% paraformaldehyde and stained with FITC-labeled rat anti-IL-7R-alpha Ab or FITC-labeled rat IgG2a (isotype control) and purified goat anti-c-Met or goat IgG (isotype control) developed with Alexa fluor 594-labeled anti-goat IgG. The cells were then observed under a Zeiss LSM510 Meta laser scanning confocal microscope equipped with a Plan-Apochromat 63×1.4 numeric aperture objective (Carl Zeiss, Thornwood, N.Y.). Images were processed using Photoshop 7.0 (Adobe Systems, Mountain View, Calif.).

Western blotting. Samples were mixed with 2×SDS sample buffer and subjected to sodium dodecyl sulfate-polyacrylamide gel electrophoresis (SDS-PAGE), and then transferred to Immobilon-P membranes (Millipore, Bedford, Mass.). After blocking with 5% blocking reagent, the membranes were incubated with primary antibodies, HRP-labeled secondary antibodies, and then developed with enhanced chemiluminescence (ECL; Amersham Biosciences).

Figure 30:
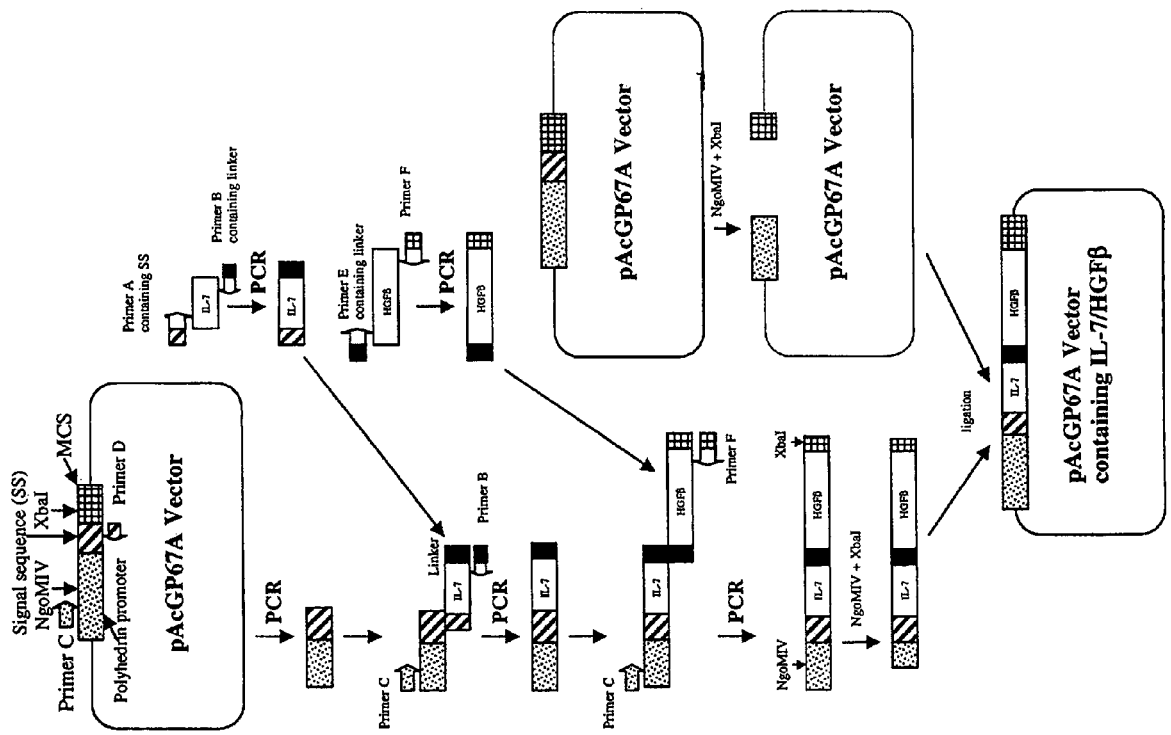
FIG. 30 Cloning strategy for ligation of the IL-7 (SEQ ID NO:10, 12), linker, and HGF-beta coding sequences (See SEQ ID NO:9, 10) into baculovirus transfer vector pAcGP67A. The gp67 secretion sequence, IL-7, linker and HGF-beta DNA are constructed by overlapping PCR as described herein.

Construction and expression of a single-chain murine IL-7 (SEQ ID NO:8)/HGF-beta (SEQ ID NO:3, 4) protein in baculovirus-insect cell expression system. The cDNA encoding murine IL-7 (SEQ ID NO:12) was generated from cultured thymus stromal cells of IL-7 (−/−) mice, and amplified with primers specifying the mature protein-coding region. Baculovirus transfer vector pAcGP67A (BD Biosciences) containing the gp67 secretion signal sequence was used for the expression and secretion of a scIL-7/HGF-beta protein in insect cells (FIG. 30). In order to insert IL-7 into the vector and to construct IL-7 and HGF-beta (See SEQ ID NO:11), DNA connected by a flexible linker encoding (Gly4Ser) IL-7 DNA was amplified with primers (Table 4) containing the 3' end of gp67 secretion signal sequence (primer A) and the linker sequence (primer B). The gp67 secretion signal sequence and a part of the polyhedrin promoter (containing the NgoMIV site) were amplified from the vector with primers C and D. The polymerase chain reaction (PCR) products of IL-7 and the signal sequence (SS-IL-7) were combined and subjected to an additional round of PCR with primers C and B. Because the 5' end of the IL-7 PCR product overlaps the 3' end of the signal sequence, the IL-7 DNA was seamlessly fused to the signal sequence after overlap extension PCR. The cDNA encoding murine HGF-beta was amplified from plasmid DNA with primers containing the linker (primer E), and stop codon and XbaI site (primer F). SS-IL-7 and HGF-beta DNA were combined and subjected to an overlap extension PCR by primers C and F. As the linker sequences in the 3' end of SS-IL-7 and the 5' end of HGF-beta overlap, an SS-IL-7 linker IL-7/HGF-beta DNA was constructed. The construct was digested with NgoMIV and XbaI, ligated into the Ngo-MIV/XbaI sites of the transfer vector, and transformed into *Escherichia coli* DH5-alpha cells. The plasmid DNA was purified and sequenced. Sf9 insect cells were cotransfected with the transfer vector and BaculoGold linearized baculovirus DNA (BD Biosciences) to construct a recombinant baculovirus containing the SS-IL-7 linker IL-7/HGF-beta DNA via homologous recombination. The recombinant baculovirus was plaque selected, and virus banks were generated according the instruction manual (BD Biosciences). Sf9 insect cells were then infected with the recombinant baculovirus to produce the scIL-7/HGF-beta protein. The highest protein expression level was achieved at a multiplicity of infection (MOI) of 2 in suspension culture (26° C. for 96 hours) using SF900II serum-free medium (SFM; Invitrogen, Carlsbad, Calif.) without protease inhibitor.

TABLE 4

Primers used for cloning of IL-7/HGFβ into expression vectors.

| Primers | Primer Sequence (5'-3') | Underlined sequences |
|---|---|---|
| A | GCGCATTCTGCCTTTGCGGAGTGCCACATTA AAGAC | NA |
| B | CGACCCACCACCGCCCGAGCCACCGCCTCCT ATACTGCCCTTCAAAAT | Linker |
| C | GGGATCGTCGGTTTTGTA | NA |

TABLE 4-continued

Primers used for cloning of IL-7/HGFβ into expression vectors.

| Primers | Primer Sequence (5'-3') | Underlined sequences |
|---------|------------------------|---------------------|
| D | CGCAAAGGCAGAATGCGC | NA |
| E | GGAGGCGGTGGCTCGGGCGGTGGTGGGTCGG TTGTAAATGGCATTCCA | Linker |
| F | TGCTCTAGACTATTACAACTTGTATGTCAA | Xba I site |
| G | CGCGGCGCGCCGAGTGCCACATTAAAGAC | Asc I site |
| H | CGCCTCGAGCTATTACAACTTGTATGTCAA | Xho I site |
| I | CGCCTCGAGAAAAGAGAGTGCCACATTAAAG AC | Xho I site |

Expression of the single-chain IL-7 (SEQ ID NO:7, 8)/HGF-beta (SEQ ID NO:3, 4, 13, and 14) protein in mammalian and yeast expression systems. The IL-7-linker-HGF-beta (IL-7/HGF-beta) DNA (See SEQ ID NO:9-12) was also subcloned into mammalian expression vector pSecTag2A containing signal IgK sequence (Invitrogen) with AscI/XhoI sites (primers G, H). The plasmid DNA was transfected into Chinese hamster ovary (CHO) cells. To express and secrete the single-chain IL-7/HGF-beta protein in a yeast expression system, a yeast expression vector was modified by insertion of a *Saccharomyces cerevisiae* (SC) alpha-factor secretion signal (cut with HindIII/XbaI) from pPIC6-alpha-A vector into HindIII/XbaI sites of YES2 (Invitrogen). IL-7/HGF-beta DNA was subcloned into the modified vector with XhoI/XbaI sites (primers I and F; Table 4). The vector containing the IL-7/HGF-beta DNA was transformed into competent INVSc1 cells with S.c. EasyComp Transformation Kit (Invitrogen) and the transformants were selected with SC-U selection plates. The INVSc1 cells were cultured in SC-U medium containing 2% glucose or raffinose and then induced by 2% galactose for another 4 to 22 hours.

Protein production and purification. The culture supernatant from the recombinant baculovirus infected Sf9 cells was concentrated by a Prep/scale-tangential flow filter (TFF) cartridge with 10 kDa molecular weight (MW) cut-off (Millipore, Bedford, Mass.) and diafiltered into washing buffer (30 mM $Na_2PO_4$, pH 7), The samples were then applied to serially linked columns of DEAE and CM sepharose (Amersham Biosciences). After washing, the linked columns were separated, and proteins were eluted from each by stepwise NaCl gradient from 25 mM to 300 mM in the washing buffer. The 200 to 300 mM CM eluates and the 37.5 to 100 mM DEAE eluates were pooled and loaded respectively on a Sephacryl S-200 column (Amersham Biosciences) pre-equilibrated with 30 mM $Na_2PO_4$ and 250 mM NaCl (pH 7). Fractions were collected and analyzed for IL-7/HGF-beta protein expression by Western blotting and thymocyte stimulating activity. Proteins were quantified by protein assay (Bio-Rad, Hercules, Calif.), using bovine serum albumin as a standard. Yields of up to 1 mg purified scIL-7/HGF-beta per liter of culture supernatant were obtained.

BM lymphoid cell culture and flow immunocytometric analysis. Rat and mouse femoral BM cells were collected by flushing with cold RPMI-1640, and the erythrocytes were lysed with 0.165 M $N_4Cl$. Nucleated cells ($2 \times 10^6$) in 2 mL RPMI-1640 containing 5% lot selected, defined fetal bovine serum (FBS) and $5 \times 10^{-5}$ M 2-mercaptoethanol (2-ME) were incubated in 35-mm diameter culture plate wells at 37° C. in 5% $CO_2$ in the presence of rIL-7 (SEQ ID NO:7, 8) and/or scIL-7 (SEQ ID NO:7, 8)/HGF-beta (SEQ ID NO:3, 4, 13, and 14). Fourteen to 19 days later, the nonadherent cells were harvested for phenotypic analysis. The cell samples were analyzed by CELL Quest on a FACScan or FACScalibur flow cytometer (all from Becton Dickinson Immunocytometry Systems, San Jose, Calif.).

Immunoprecipitation of phospho-Jak3 and c-Met. Culture-generated B-lineage cells were washed, cytokine-starved for 5 hours, and stimulated with either rIL-7 (20 ng/mL) or rIL-7/HGF-beta (60 ng/mL) for 10 to 30 minutes. The stimulated and unstimulated control cells were lysed in 25 mM Tris-HCL (pH 8), 150 mM NaCl, 1% Triton, 0.5% Igepal, and 1 mM sodium orthovanadate plus protease inhibitors. The supernatants were immunoprecipitated with antibodies against Jak3 or phosphotyrosine and protein G-agarose bead slurry. Pellets were resuspended in SDS sample buffer and subjected to Western blotting using antibodies against phosphotyrosine or phospho-c-Met.

Purification of the IL-7/HGF-beta receptor. scIL-7/HGF-beta (1 mg) was coupled to 0.2 mL cyanogen bromide (CNBr)-activated sepharose 4B according to the manufacturer's instructions. Purified CD19⁻ AA4.1⁺ culture-generated cells ($10^8$; CLPs and pre-pro-B cells) were added to 2 mL lysis buffer (10 mM Tris-HCl buffer [pH 7.2], 150 mM NaCl, and protease inhibitor cocktail in the presence of 1% Triton X-100), and the supernatant was added to a scIL-7/HGF-beta affinity gel and gently rocked overnight at 4° C. as described. After extensive washing with the lysis buffer (10 mM Tris-HCl buffer [pH 7.2] containing 0.15 M NaCl, 0.1% Triton X-100, and the protease inhibitor cocktail), the IL-7/HGF-beta receptor was eluted in a stepwise fashion with 0.1 M glycine-HCL buffer (pH 3.3), 0.1 M glycine-HCl buffer (pH 2.0), and then 0.1 M sodium citrate buffer (pH 2.0) each containing 0.2 M NaCl, 0.1% Triton X-100, and the protease inhibitor cocktail. The eluates were immediately neutralized with 2 M Tris base and subjected to SDS-PAGE and Western blotting.

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety.

What is claimed is:

1. A chimeric polypeptide comprising: an IL-7 polypeptide; and a hepatocyte growth factor-beta chain (HGFβ) polypeptide, wherein the IL-7 and HGFβ polypeptides are joined covalently to form a single contiguous polypeptide chain, and wherein the chimeric polypeptide is capable of inducing the proliferation and differentiation of pre-pro-B-cells.

2. The chimeric polypeptide of claim 1, wherein the chimeric polypeptide comprises a heterologous polypeptide.

3. The chimeric polypeptide of claim 1, wherein the single contiguous polypeptide chain further comprises a linker comprising an amino acid sequence disposed between the IL-7 and HGFβ polypeptides.

4. The chimeric polypeptide of claim 1, wherein the chimeric polypeptide comprises a polypeptide having at least 95% sequence identity with SEQ ID NO: 7.

5. The chimeric polypeptide of claim 1, wherein the chimeric polypeptide comprises a polypeptide having at least 95% sequence identity with SEQ ID NO: 14.

6. The chimeric polypeptide of claim 3, wherein the linker comprises an amino acid sequence having from 1 to 50 amino acids.

7. The chimeric polypeptide of claim 1, further comprising: an amino acid linker, wherein the IL-7 polypeptide is a polypeptide having at least 95% sequence identity with the amino acid sequence set forth in SEQ ID NO: 7; and the hepatocyte growth factor-beta chain (HGF j3) polypeptide is a polypeptide having at least 95% sequence identity with the amino acid sequence set forth in SEQ ID NO: 14, and wherein the linker, the IL-7 polypeptide, and HGFβ polypeptide are joined within a contiguous polypeptide chain.

8. The chimeric polypeptide of claim 7, wherein the linker comprises from 5 to 50 amino acids.

9. The chimeric polypeptide of claim 8, wherein the linker comprises from 5 to 20 amino acids.

10. The chimeric polypeptide of claim 8, wherein the linker further comprises an amino acid consensus sequence for at least one of phosphorylation, acetylation, methylation, protease cleavage, isomerization, ubiquitination, protein binding, or a combination thereof.

11. The chimeric polypeptide of claim 9, wherein the linker comprises the amino acid sequence as set forth in SEQ ID NO.:15.

12. A method of inducing the proliferation and differentiation of a hematopoietic progenitor cell, comprising administering an effective amount of the chimeric polypeptide of claim 1, in combination with at least one pharmaceutically acceptable excipients[s], to an undifferentiated pre-pro-B-cell.

* * * * *

UNITED STATES PATENT AND TRADEMARK OFFICE
CERTIFICATE OF CORRECTION

| | | |
|---|---|---|
| PATENT NO. | : 7,578,998 B2 | Page 1 of 1 |
| APPLICATION NO. | : 11/601059 | |
| DATED | : August 25, 2009 | |
| INVENTOR(S) | : Irving Goldschneider and Laijun Lai | |

It is certified that error appears in the above-identified patent and that said Letters Patent is hereby corrected as shown below:

In the specification:

Remove at Column 1, line 21 -- The U.S. Government has certain rights in this invention pursuant to Grant No. R01-AI32752, awarded by the national Institutes of Health (NIH). --

Insert at Column 1, line 21

-- This invention was made with government support under Grant No. AI032752 awarded by the National Institutes of Health (NIH). The government has certain rights in the invention. --

Signed and Sealed this

Thirteenth Day of September, 2011

David J. Kappos
*Director of the United States Patent and Trademark Office*

SEQUENCE LISTING

<160> NUMBER OF SEQ ID NOS: 14

<210> SEQ ID NO 1
<211> LENGTH: 18

-continued

```
<212> TYPE: DNA
<213> ORGANISM: Mus musculus
<220> FEATURE:
<221> NAME/KEY: HGF Primer 5' flanking region
<222> LOCATION: (1)..(18)

<400> SEQUENCE: 1
cagtctgctc gaactgca                                                 18

<210> SEQ ID NO 2
<211> LENGTH: 18
<212> TYPE: DNA
<213> ORGANISM: Mus musculus
<220> FEATURE:
<221> NAME/KEY: HGF primer
<222> LOCATION: (1)..(18)

<400> SEQUENCE: 2
tggcctcttc tatggcta                                                 18

<210> SEQ ID NO 3
<211> LENGTH: 17
<212> TYPE: PRT
<213> ORGANISM: Mus musculus
<220> FEATURE:
<221> NAME/KEY: PEPTIDE
<222> LOCATION: (1)..(17)

<400> SEQUENCE: 3

Val Val Asn Gly Ile Pro Thr Gln Thr Asn Ile Gly Trp Met Val Ser
1               5                   10                  15

Leu

<210> SEQ ID NO 4
<211> LENGTH: 17
<212> TYPE: PRT
<213> ORGANISM: Mus musculus
<220> FEATURE:
<221> NAME/KEY: Mouse HGF-Beta chain
<222> LOCATION: (1)..(17)

<400> SEQUENCE: 4

Val Val Asn Gly Ile Pro Thr Gln Thr Thr Val Gly Trp Met Val Ser
1               5                   10                  15

Leu

<210> SEQ ID NO 5
<211> LENGTH: 728
<212> TYPE: PRT
<213> ORGANISM: Homo sapiens
<220> FEATURE:
<221> NAME/KEY: human HGF protein
<222> LOCATION: (1)..(728)
<223> OTHER INFORMATION: ACCESSION   BAA14348

<400> SEQUENCE: 5

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60
```

-continued

```
Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
```

```
                    485                 490                 495
Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
                515                 520                 525

Val Leu Thr Ala Arg Gln Cys Phe Pro Ser Arg Asp Leu Lys Asp Tyr
            530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 6
<211> LENGTH: 728
<212> TYPE: PRT
<213> ORGANISM: Mus musculus
<220> FEATURE:
<221> NAME/KEY: Mouse HGF Protein
<222> LOCATION: (1)..(728)
<223> OTHER INFORMATION: ACCESSION   NP_034557 XP_131908

<400> SEQUENCE: 6

Met Met Trp Gly Thr Lys Leu Leu Pro Val Leu Leu Leu Gln His Val
1               5                   10                  15

Leu Leu His Leu Leu Leu Leu His Val Ala Ile Pro Tyr Ala Glu Gly
            20                  25                  30

Gln Lys Lys Arg Arg Asn Thr Leu His Glu Phe Lys Lys Ser Ala Lys
        35                  40                  45

Thr Thr Leu Thr Lys Glu Asp Pro Leu Leu Lys Ile Lys Thr Lys Lys
    50                  55                  60

Val Asn Ser Ala Asp Glu Cys Ala Asn Arg Cys Ile Arg Asn Arg Gly
65                  70                  75                  80

Phe Thr Phe Thr Cys Lys Ala Phe Val Phe Asp Lys Ser Arg Lys Arg
                85                  90                  95

Cys Tyr Trp Tyr Pro Phe Asn Ser Met Ser Ser Gly Val Lys Lys Gly
            100                 105                 110
```

```
Phe Gly His Glu Phe Asp Leu Tyr Glu Asn Lys Asp Tyr Ile Arg Asn
            115                 120                 125

Cys Ile Ile Gly Lys Gly Gly Ser Tyr Lys Gly Thr Val Ser Ile Thr
            130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Pro Trp Cys Phe Thr
            180                 185                 190

Ser Asn Pro Glu Val Arg Tyr Glu Val Cys Asp Ile Pro Gln Cys Ser
            195                 200                 205

Glu Val Glu Cys Met Thr Cys Asn Gly Glu Ser Tyr Arg Gly Pro Met
            210                 215                 220

Asp His Thr Glu Ser Gly Lys Thr Cys Gln Arg Trp Asp Gln Gln Thr
225                 230                 235                 240

Pro His Arg His Lys Phe Leu Pro Glu Arg Tyr Pro Asp Lys Gly Phe
                245                 250                 255

Asp Asp Asn Tyr Cys Arg Asn Pro Asp Gly Lys Pro Arg Pro Trp Cys
            260                 265                 270

Tyr Thr Leu Asp Pro Asp Thr Trp Glu Tyr Cys Ala Ile Lys Thr
            275                 280                 285

Cys Ala His Ser Ala Val Asn Glu Thr Asp Val Pro Met Glu Thr Thr
            290                 295                 300

Glu Cys Ile Gln Gly Gln Gly Glu Gly Tyr Arg Gly Thr Ser Asn Thr
305                 310                 315                 320

Ile Trp Asn Gly Ile Pro Cys Gln Arg Trp Asp Ser Gln Tyr Pro His
                325                 330                 335

Lys His Asp Ile Thr Pro Glu Asn Phe Lys Cys Lys Asp Leu Arg Glu
            340                 345                 350

Asn Tyr Cys Arg Asn Pro Asp Gly Ala Glu Ser Pro Trp Cys Phe Thr
            355                 360                 365

Thr Asp Pro Asn Ile Arg Val Gly Tyr Cys Ser Gln Ile Pro Lys Cys
370                 375                 380

Asp Val Ser Ser Gly Gln Asp Cys Tyr Arg Gly Asn Gly Lys Asn Tyr
385                 390                 395                 400

Met Gly Asn Leu Ser Lys Thr Arg Ser Gly Leu Thr Cys Ser Met Trp
                405                 410                 415

Asp Lys Asn Met Glu Asp Leu His Arg His Ile Phe Trp Glu Pro Asp
            420                 425                 430

Ala Ser Lys Leu Asn Lys Asn Tyr Cys Arg Asn Pro Asp Asp Ala
            435                 440                 445

His Gly Pro Trp Cys Tyr Thr Gly Asn Pro Leu Ile Pro Trp Asp Tyr
            450                 455                 460

Cys Pro Ile Ser Arg Cys Glu Gly Asp Thr Thr Pro Thr Ile Val Asn
465                 470                 475                 480

Leu Asp His Pro Val Ile Ser Cys Ala Lys Thr Lys Gln Leu Arg Val
                485                 490                 495

Val Asn Gly Ile Pro Thr Gln Thr Thr Val Gly Trp Met Val Ser Leu
            500                 505                 510

Lys Tyr Arg Asn Lys His Ile Cys Gly Gly Ser Leu Ile Lys Glu Ser
            515                 520                 525
```

-continued

Trp Val Ile Thr Ala Arg Gln Cys Phe Pro Ala Arg Asn Lys Asp Leu
    530                 535                 540

Lys Asp Tyr Glu Ala Trp Leu Gly Ile His Asp Val His Glu Arg Gly
545                 550                 555                 560

Glu Glu Lys Arg Lys Gln Ile Leu Asn Ile Ser Gln Leu Val Tyr Gly
                565                 570                 575

Pro Glu Gly Ser Asp Leu Val Leu Leu Lys Leu Ala Arg Pro Ala Ile
            580                 585                 590

Leu Asp Asn Phe Val Ser Thr Ile Asp Leu Pro Ser Tyr Gly Cys Thr
        595                 600                 605

Ile Pro Glu Lys Thr Thr Cys Ser Ile Tyr Gly Trp Gly Tyr Thr Gly
    610                 615                 620

Leu Ile Asn Ala Asp Gly Leu Leu Arg Val Ala His Leu Tyr Ile Met
625                 630                 635                 640

Gly Asn Glu Lys Cys Ser Gln His His Gln Gly Lys Val Thr Leu Asn
                645                 650                 655

Glu Ser Glu Leu Cys Ala Gly Ala Glu Lys Ile Gly Ser Gly Pro Cys
            660                 665                 670

Glu Gly Asp Tyr Gly Gly Pro Leu Ile Cys Glu Gln His Lys Met Arg
        675                 680                 685

Met Val Leu Gly Val Ile Val Pro Gly Arg Gly Cys Ala Ile Pro Asn
    690                 695                 700

Arg Pro Val Ile Phe Val Arg Val Ala Tyr Tyr Ala Lys Trp Ile His
705                 710                 715                 720

Lys Val Ile Leu Thr Tyr Lys Leu
                725

<210> SEQ ID NO 7
<211> LENGTH: 177
<212> TYPE: PRT
<213> ORGANISM: Homo sapiens
<220> FEATURE:
<221> NAME/KEY: Human IL-7 Protein
<222> LOCATION: (1)..(177)
<223> OTHER INFORMATION: ACCESSION   NP_000871

<400> SEQUENCE: 7

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu

```
                145                 150                 155                 160
Gln Glu Ile Lys Thr Cys Trp Asn Lys Ile Leu Met Gly Thr Lys Glu
                165                 170                 175

His

<210> SEQ ID NO 8
<211> LENGTH: 154
<212> TYPE: PRT
<213> ORGANISM: Mus musculus
<220> FEATURE:
<221> NAME/KEY: Mouse IL-7 Protein
<222> LOCATION: (1)..(154)
<223> OTHER INFORMATION: ACCESSION   NP_032397

<400> SEQUENCE: 8

Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
                20                  25                  30

Glu Gly Lys Ala Tyr Glu Ser Val Leu Met Ile Ser Ile Asp Glu Leu
            35                  40                  45

Asp Lys Met Thr Gly Thr Asp Ser Asn Cys Pro Asn Asn Glu Pro Asn
        50                  55                  60

Phe Phe Arg Lys His Val Cys Asp Asp Thr Lys Glu Ala Ala Phe Leu
65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
                100                 105                 110

Leu Val Asn Cys Thr Ser Lys Glu Glu Lys Asn Val Lys Glu Gln Lys
            115                 120                 125

Lys Asn Asp Ala Cys Phe Leu Lys Arg Leu Leu Arg Glu Ile Lys Thr
        130                 135                 140

Cys Trp Asn Lys Ile Leu Lys Gly Ser Ile
145                 150

<210> SEQ ID NO 9
<211> LENGTH: 2187
<212> TYPE: DNA
<213> ORGANISM: Homo sapiens
<220> FEATURE:
<221> NAME/KEY: Human HGF cDNA
<222> LOCATION: (1)..(2187)
<223> OTHER INFORMATION: ACCESSION   NM_000601

<400> SEQUENCE: 9
atgtgggtga ccaaactcct gccagccctg ctgctgcagc atgtcctcct gcatctcctc     60
ctgctcccca tcgccatccc ctatgcagag ggacaaagga aagaagaaa tacaattcat    120 gaattcaaaa aatcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgttttttgat aaagcaagaa acaatgcct ctggttcccc    300 ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta gagtggcat caaatgtcag ccctggagtt ccatgatacc acacgaacac    480
agctttttgc cttcgagcta tcggggtaaa gacctacagg aaaactactg tcgaaatcct    540
```

-continued

```
cgaggggaag aaggggga cc ctggtgtttc acaagcaatc cagaggtacg ctacgaagtc    600
tgtgacattc ctcagtgttc agaagttgaa tgcatgacct gcaatgggga gagttatcga    660
ggtctcatgg atcatacaga atcaggcaag atttgtcagc gctgggatca tcagacacca    720
caccggcaca aattcttgcc tgaaagatat cccgacaagg ctttgatga taattattgc    780 cgcaatcccg atggccagcc gaggccatgt tgctatactc ttgaccctca cacccgctgg    840
gagtactgtg caattaaaac atgcgctgac aatactatga atgacactga tgttcctttg    900
gaaacaactg aatgcatcca aggtcaagga aaggctaca ggggcactgt caataccatt    960
tggaatggaa ttccatgtca cgttgggat tctcagtatc ctcacgagca tgacatgact    1020
cctgaaaatt tcaagtgcaa ggacctacga gaaaattact gccgaaatcc agatgggtct    1080
gaatcaccct ggtgttttac cactgatcca aacatccgag ttggctactg ctcccaaatt    1140
ccaaactgtg atatgtcaca tggacaagat tgttatcgtg gaatggcaa aaattatatg    1200 ggcaacttat cccaaacaag atctggacta acatgttcaa tgtgggacaa gaacatggaa    1260
gacttacatc gtcatatctt ctgggaacca gatgcaagta agctgaatga gaattactgc    1320
cgaaatccag atgatgatgc tcatggaccc tggtgctaca cgggaaatcc actcattcct    1380
tgggattatt gccctattc tcgttgtgaa ggtgatacca cacctacaat agtcaattta    1440
gaccatcccg taatatcttg tgccaaaacg aaacaattgc gagttgtaaa tgggattcca    1500
acacgaacaa acataggatg gatggttagt ttgagataca gaaataaaca tatctgcgga    1560
ggatcattga taaaggagag ttgggttctt actgcacgac agtgtttccc ttctcgagac    1620
ttgaaagatt atgaagcttg gcttggaatt catgatgtcc acggaagagg agatgagaaa    1680
tgcaaacagg ttctcaatgt ttcccagctg gtatatggcc ctgaaggatc agatctggtt    1740
ttaatgaagc ttgccaggcc tgctgtcctg gatgattttg ttagtacgat tgatttacct    1800
aattatggat gcacaattcc tgaaaagacc agttgcagtg tttatggctg gggctacact    1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtggcccact tgtttgtgag    2040
caacataaaa tgagaatggt tcttggtgtc attgttcctg gtcgtggatg tgccattcca    2100
aatcgtcctg gtattttgt ccgagtagca tattatgcaa aatggataca caaattatt    2160 ttaacatata aggtaccaca gtcatag                                        2187
```

<210> SEQ ID NO 10
<211> LENGTH: 534
<212> TYPE: DNA
<213> ORGANISM: Homo sapiens
<220> FEATURE:
<221> NAME/KEY: Human IL-7 cDNA
<222> LOCATION: (1)..(534)
<223> OTHER INFORMATION: ACCESSION  NM_000880

<400> SEQUENCE: 10

```
atgttccatg tttcttttag gtatatcttt ggacttcctc ccctgatcct tgttctgttg     60
ccagtagcat catctgattg tgatattgaa ggtaaagatg gcaaacaata tgagagtgtt    120
ctaatggtca gcatcgatca attattggac agcatgaaag aaattggtag caattgcctg    180
aataatgaat ttaaccttttt taaaagacat atctgtgatg ctaataagga aggtatgttt    240
ttattccgtg ctgctcgcaa gttgaggcaa tttcttaaaa tgaatagcac tggtgatttt    300
gatctccact tattaaaagt ttcagaaggc acaacaatac tgttgaactg cactggccag    360
```

| gttaaaggaa gaaaaccagc tgccctgggt gaagcccaac caacaaagag tttggaagaa | 420 |
| aataaatctt taaaggaaca gaaaaaactg aatgacttgt gtttcctaaa gagactatta | 480 |
| caagagataa aaacttgttg gaataaaatt ttgatgggca ctaaagaaca ctga | 534 |

```
<210> SEQ ID NO 11
<211> LENGTH: 2190
<212> TYPE: DNA
<213> ORGANISM: Mus musculus
<220> FEATURE:
<221> NAME/KEY: Mouse HGF cDNA
<222> LOCATION: (1)..(2190)
<223> OTHER INFORMATION: ACCESSION   NM_010427 XM_131908

<400> SEQUENCE: 11
```

| agcatgatgt gggggaccaa acttctgccg gtcctgttgc tgcagcatgt cctcctgcac | 60 |
| ctcctcctgc ttcatgtcgc catccctat gcagaaggac agaagaaaag aagaaataca | 120 |
| cttcatgaat ttaaaaagtc agcaaaaact actcttacca aggaagaccc attactgaag | 180 |
| attaaaacca aaaagtgaa ctctgcagat gagtgtgcca acaggtgtat caggaacagg | 240 |
| ggctttacgt tcacttgcaa ggccttcgtt tttgataagt caagaaaacg atgctactgg | 300 |
| tatccttca atagtatgtc aagtggagtg aaaaagggt ttggccatga atttgacctc | 360 |
| tatgaaaaca aagactatat tagaaactgc atcattggta aaggaggcag ctataaaggg | 420 |
| acggtatcca tcactaagag tggcatcaaa tgccagcctt ggaattccat gatcccccat | 480 |
| gaacacagct ttttgccttc gagctatcgc ggtaaagacc tacaggaaaa ctactgtcga | 540 |
| aatcctcgag gggaagaagg gggaccctgg tgtttcacaa gcaatccaga ggtacgctac | 600 |
| gaagtctgtg acattcctca gtgttcagaa gttgaatgca tgacctgcaa tggtgaaagc | 660 |
| tacagaggtc ccatggatca cacagaatca ggcaagactt gtcagcgctg ggaccagcag | 720 |
| acaccacacc ggcacaagtt cttgccagaa agatatcccg acaagggctt tgatgataat | 780 |
| tattgccgca atcctgatgg caagccgagg ccatggtgct acactcttga ccctgacacc | 840 |
| acttgggagt attgtgcaat taaaacgtgc gctcacagtg ctgtgaatga gactgatgtc | 900 |
| cctatggaaa caactgaatg cattcaaggc caaggagaag gttacagggg aaccagcaat | 960 |
| accatttgga tggaattcc ctgtcagcgt tgggattcgc agtaccctca caagcatgat | 1020 |
| atcactcccg agaacttcaa atgcaaggac cttagagaaa attattgccg caatccagat | 1080 |
| ggggctgaat caccatggtg ttttaccact gaccccaaca tccgagttgg ctactgctct | 1140 |
| cagattccca gtgtgacgt gtcaagtgga caagattgtt atcgtggcaa tgggaaaaat | 1200 |
| tacatgggca acttatccaa aacaaggtct ggacttacat gttccatgtg gacaagaat | 1260 |
| atggaggatt tacaccgtca tatcttctgg gagccagatg ctagcaaatt gaataagaat | 1320 |
| tactgccgga atcctgatga tgatgcccat ggacctggt gctacacggg gaatcctctt | 1380 |
| attccttggg attattgccc tatttcccgt tgtgaaggag atactacacc tacaattgtc | 1440 |
| aatttggacc atcctgtaat atcctgtgcc aaaacaaaac aactgcgggt tgtaaatggc | 1500 |
| attccaacac aaacaacagt agggtggatg gttagtttga aatacagaaa taaacatatc | 1560 |
| tgtggaggat cattgataaa ggaaagttgg gttattactg caagcaatg ttttccagcc | 1620 |
| agaaacaaag acttgaaaga ctatgaagct tggcttggca tccacgatgt tcatgagaga | 1680 |
| ggcgaggaga agcgcaagca gatcttaaac atttcccagc tggtctatgg tcctgaaggc | 1740 |
| tcagacttgg ttttactgaa gcttgctcga cctgcaatcc tggataactt tgtcagtaca | 1800 |

-continued

```
attgatttac ctagttatgg ttgtacaatc cctgaaaaga ccacttgcag tatttacggc    1860
tggggctaca ctggattgat caacgcggat ggtttattac gagtagctca tctgtatatt    1920
atggggaatg agaaatgcag tcagcaccat caaggcaagg tgactttgaa tgagtctgag    1980
ttatgtgctg gggctgaaaa gattggatca ggaccatgtg agggagatta tggtggccca    2040
ctcatttgtg aacaacacaa aatgagaatg gttcttggtg tcattgttcc tggtcgtgga    2100
tgtgccatcc caaatcgtcc tgttattttt gttcgagtag catattatgc aaaatggata    2160
cacaaagtaa ttttgacata caagttgtaa                                     2190
```

<210> SEQ ID NO 12
<211> LENGTH: 465
<212> TYPE: DNA
<213> ORGANISM: Mus musculus
<220> FEATURE:
<221> NAME/KEY: Mouse IL-7 cDNA
<222> LOCATION: (1)..(465)
<223> OTHER INFORMATION: ACCESSION  NM_008371

<400> SEQUENCE: 12

```
atgttccatg tttctttttag atatatctttt ggaattcctc cactgatcct tgttctgctg     60
cctgtcacat catctgagtg ccacattaaa gacaaagaag gtaaagcata tgagagtgta    120
ctgatgatca gcatcgatga attggacaaa atgacaggaa ctgatagtaa ttgcccgaat    180
aatgaaccaa acttttttag aaaacatgta tgtgatgata caaaggaagc tgcttttcta    240
aatcgtgctg ctcgcaagtt gaagcaattt cttaaaatga atatcagtga agaattcaat    300
gtccacttac taacagtatc acaaggcaca caaacactgg tgaactgcac aagtaaggaa    360
gaaaaaaacg taaaggaaca gaaaaagaat gatgcatgtt tcctaaagag actactgaga    420
gaaataaaaa cttgttggaa taaaattttg aagggcagta tataa                   465
```

<210> SEQ ID NO 13
<211> LENGTH: 17
<212> TYPE: PRT
<213> ORGANISM: Homo sapiens
<220> FEATURE:
<221> NAME/KEY: Human HGF beta-chain peptide
<222> LOCATION: (1)..(17)

<400> SEQUENCE: 13

Val Val Asn Gly Ile Pro Thr Arg Thr Asn Ile Gly Trp Met Val Ser
1               5                   10                  15

Leu

<210> SEQ ID NO 14
<211> LENGTH: 234
<212> TYPE: PRT
<213> ORGANISM: Homo sapiens
<220> FEATURE:
<221> NAME/KEY: Human HGF-beta chain entire sequence
<222> LOCATION: (1)..(234)
<223> OTHER INFORMATION: Corresponds to amino acids 495 to 728 of HGF

<400> SEQUENCE: 14

Val Val Asn Gly Ile Pro Thr Arg Thr Asn Ile Gly Trp Met Val Ser
1               5                   10                  15

Leu Arg Tyr Arg Asn Lys His Ile Cys Gly Gly Ser Leu Ile Lys Glu
            20                  25                  30

Ser Trp Val Leu Thr Ala Arg Gln Cys Phe Pro Ser Arg Asp Leu Lys
        35                  40                  45

-continued

```
Asp Tyr Glu Ala Trp Leu Gly Ile His Asp Val His Gly Arg Gly Asp
    50                  55                  60

Glu Lys Cys Lys Gln Val Leu Asn Val Ser Gln Leu Val Tyr Gly Pro
65                  70                  75                  80

Glu Gly Ser Asp Leu Val Leu Met Lys Leu Ala Arg Pro Ala Val Leu
            85                  90                  95

Asp Asp Phe Val Ser Thr Ile Asp Leu Pro Asn Tyr Gly Cys Thr Ile
            100                 105                 110

Pro Glu Lys Thr Ser Cys Ser Val Tyr Gly Trp Gly Tyr Thr Gly Leu
        115                 120                 125

Ile Asn Tyr Asp Gly Leu Leu Arg Val Ala His Leu Tyr Ile Met Gly
        130                 135                 140

Asn Glu Lys Cys Ser Gln His His Arg Gly Lys Val Thr Leu Asn Glu
145                 150                 155                 160

Ser Glu Ile Cys Ala Gly Ala Glu Lys Ile Gly Ser Gly Pro Cys Glu
            165                 170                 175

Gly Asp Tyr Gly Gly Pro Leu Val Cys Glu Gln His Lys Met Arg Met
            180                 185                 190

Val Leu Gly Val Ile Val Pro Gly Arg Gly Cys Ala Ile Pro Asn Arg
        195                 200                 205

Pro Gly Ile Phe Val Arg Val Ala Tyr Tyr Ala Lys Trp Ile His Lys
        210                 215                 220

Ile Ile Leu Thr Tyr Lys Val Pro Gln Ser
225                 230
```